US012708535B2

(12) United States Patent
Bly et al.

(10) Patent No.: US 12,708,535 B2
(45) Date of Patent: Aug. 18, 2026

(54) SYSTEMS, DEVICES, AND METHODS FOR THE ACCURATE DEPLOYMENT AND IMAGING OF AN IMPLANT IN THE PROSTATIC URETHRA

(71) Applicant: ZENFLOW, INC., San Francisco, CA (US)

(72) Inventors: Austin Michael Bly, San Clemente, CA (US); Cesar Abalos Ico, San Francisco, CA (US); Shreya Mehta, San Francisco, CA (US); William Martin Belef, San Jose, CA (US); Samuel Allen Scaglione, San Jose, CA (US); Marcel Song Sicotte, San Francisco, CA (US); Khoi Le, San Jose, CA (US)

(73) Assignee: ZENFLOW, INC., San Francisco, CA (US)

(*) Notice: Subject to any disclaimer, the term of this patent is extended or adjusted under 35 U.S.C. 154(b) by 322 days.

(21) Appl. No.: 18/392,316

(22) Filed: Dec. 21, 2023

(65) Prior Publication Data

US 2024/0341984 A1 Oct. 17, 2024

Related U.S. Application Data

(63) Continuation of application No. 16/951,256, filed on Nov. 18, 2020, now Pat. No. 11,890,213.

(Continued)

(51) Int. Cl.

*A61F 2/95* (2013.01)
*A61F 2/966* (2013.01)

(Continued)

(52) U.S. Cl.

CPC .............. *A61F 2/9517* (2020.05); *A61F 2/95* (2013.01); *A61F 2/966* (2013.01); *A61B 2017/00292* (2013.01); *A61F 2002/047* (2013.01)

(58) Field of Classification Search

CPC .......... A61F 2/9517; A61F 2/95; A61F 2/966; A61F 2/89; A61F 2002/9534; A61F 2002/047; A61B 1/307; A61B 1/00135

See application file for complete search history.

(56) References Cited

U.S. PATENT DOCUMENTS 3,657,744 A 4/1972 Ersek
5,041,126 A 8/1991 Gianturco (Continued)

FOREIGN PATENT DOCUMENTS

CN 202891882 U 4/2013
CN 103815859 A 5/2014

(Continued)

OTHER PUBLICATIONS

JP, 2022-528612 Office Action, May 27, 2025.

(Continued)

*Primary Examiner* — Dianne Dornbusch
(74) *Attorney, Agent, or Firm* — ONE LLP

(57) ABSTRACT

Systems, devices, and methods are provided for the delivery of an implant into the prostatic urethra. Embodiments of delivery systems can include a delivery device for insertion into the patient and a proximal control device for use in controlling release of the implant from the delivery device.

9 Claims, 47 Drawing Sheets

Related U.S. Application Data

(60) Provisional application No. 62/937,625, filed on Nov. 19, 2019.

(51) Int. Cl.
*A61B 17/00* (2006.01)
*A61F 2/04* (2013.01)

(56) References Cited

U.S. PATENT DOCUMENTS 5,160,341 A 11/1992 Brenneman et al.
5,246,445 A 9/1993 Yachia
5,261,916 A 11/1993 Engelson
5,269,802 A 12/1993 Garber
5,282,472 A 2/1994 Companion et al.
5,372,600 A 12/1994 Beyar et al.
5,413,601 A 5/1995 Keshelava
5,433,723 A 7/1995 Lindenberg et al.
5,466,242 A 11/1995 Mori
5,490,860 A 2/1996 Middle et al.
5,507,767 A 4/1996 Maeda et al.
5,514,176 A 5/1996 Bosley
5,514,178 A 5/1996 Torchio
5,531,718 A 7/1996 Sachse
5,540,701 A 7/1996 Sharkey et al.
5,540,713 A 7/1996 Schnepp Pesch et al.
5,545,210 A 8/1996 Hess et al.
5,554,181 A 9/1996 Das
5,556,413 A 9/1996 Lam
5,556,414 A 9/1996 Turi
5,562,641 A 10/1996 Flomenblit et al.
5,603,722 A 2/1997 Phan et al.
5,607,445 A 3/1997 Summers
5,609,629 A 3/1997 Fearnot et al.
5,634,946 A 6/1997 Slepian
5,658,311 A 8/1997 Baden
5,662,713 A 9/1997 Andersen et al.
5,667,486 A 9/1997 Mikulich et al.
5,667,522 A 9/1997 Flomenblit et al.
5,674,241 A 10/1997 Bley et al.
5,674,242 A 10/1997 Phan et al.
5,681,274 A 10/1997 Perkins et al.
5,685,824 A 11/1997 Takei
5,725,549 A 3/1998 Lam
5,749,915 A 5/1998 Slepian
5,749,918 A 5/1998 Hogendijk et al.
5,772,668 A 6/1998 Summers et al.
5,782,838 A 7/1998 Beyar et al.
5,797,952 A 8/1998 Klein
5,824,040 A 10/1998 Cox et al.
5,824,049 A 10/1998 Ragheb et al.
5,830,179 A 11/1998 Mikus et al.
5,830,228 A 11/1998 Knapp et al.
5,843,168 A 12/1998 Dang
5,861,035 A 1/1999 Griffith
5,865,815 A 2/1999 Tihon
5,873,904 A 2/1999 Ragheb et al.
5,876,434 A 3/1999 Flomenblit et al.
5,876,445 A 3/1999 Andersen et al.
5,899,934 A 5/1999 Amundson et al.
5,907,893 A 6/1999 Zadno Azizi et al.
5,928,217 A 7/1999 Mikus et al.
5,929,901 A 7/1999 Adair et al.
5,938,585 A 8/1999 Donofrio
5,954,766 A 9/1999 Zadno Azizi et al.
5,964,771 A 10/1999 Beyar et al.
5,968,070 A 10/1999 Bley et al.
5,972,027 A 10/1999 Johnson
5,980,554 A 11/1999 Lenker et al.
6,013,854 A 1/2000 Moriuchi
6,019,779 A 2/2000 Thorud et al.
6,022,312 A * 2/2000 Chaussy ............... A61F 2/0022 604/246
6,033,413 A 3/2000 Mikus et al.
6,036,702 A 3/2000 Bachinski et al.
6,053,943 A 4/2000 Edwin et al.
6,059,808 A 5/2000 Boussignac et al.
6,086,528 A 7/2000 Adair
6,090,115 A 7/2000 Beyar et al.
6,090,134 A 7/2000 Tu et al.
6,096,070 A 8/2000 Ragheb et al.
6,136,023 A 10/2000 Boyle
6,139,536 A 10/2000 Mikus et al.
6,165,194 A 12/2000 Denardo
6,174,305 B1 1/2001 Mikus et al.
6,190,394 B1 2/2001 Lind et al.
6,197,051 B1 3/2001 Zhong
6,203,552 B1 3/2001 Bagley et al.
6,211,904 B1 4/2001 Adair et al.
6,238,430 B1 5/2001 Klumb et al.
6,248,122 B1 6/2001 Klumb et al.
6,253,443 B1 7/2001 Johnson
6,258,115 B1 7/2001 Dubrul
6,258,118 B1 7/2001 Baum et al.
6,283,991 B1 9/2001 Cox et al.
6,305,436 B1 10/2001 Andersen et al.
6,306,141 B1 10/2001 Jervis
6,310,642 B1 10/2001 Adair et al.
6,315,791 B1 11/2001 Gingras et al.
6,327,772 B1 12/2001 Zadno Azizi et al.
6,332,892 B1 12/2001 Desmond et al.
6,371,953 B1 4/2002 Beyar et al.
6,375,458 B1 4/2002 Moorleghem et al.
6,379,379 B1 4/2002 Wang
6,395,021 B1 5/2002 Hart et al.
6,409,750 B1 6/2002 Hyodoh et al.
6,413,269 B1 7/2002 Bui et al.
6,413,273 B1 7/2002 Baum et al.
6,416,545 B1 7/2002 Mikus et al.
6,488,700 B2 12/2002 Klumb et al.
6,497,724 B1 12/2002 Stevens et al.
6,506,211 B1 1/2003 Skubitz et al.
6,514,285 B1 2/2003 Pinchasik
6,530,951 B1 3/2003 Bates et al.
6,562,064 B1 5/2003 deBeer
6,572,648 B1 6/2003 Klumb et al.
6,585,753 B2 7/2003 Eder et al.
6,602,281 B1 8/2003 Klein
6,605,107 B1 8/2003 Klein
6,616,653 B2 9/2003 Beyar et al.
6,629,981 B2 10/2003 Bui et al.
6,632,243 B1 10/2003 Zadno Azizi et al.
6,641,605 B1 11/2003 Stergiopulos
6,645,237 B2 11/2003 Klumb et al.
6,652,575 B2 11/2003 Wang
6,660,032 B2 12/2003 Klumb et al.
6,699,279 B2 3/2004 Stevens et al.
6,702,829 B2 3/2004 Bachinski et al.
6,702,846 B2 3/2004 Mikus et al.
6,706,408 B2 3/2004 Jelle
6,733,536 B1 5/2004 Gellman
6,746,489 B2 6/2004 Dua et al.
6,755,854 B2 6/2004 Gillick et al.
6,764,519 B2 7/2004 Whitmore
6,770,101 B2 8/2004 Desmond et al.
6,774,278 B1 8/2004 Ragheb et al.
6,790,223 B2 9/2004 Reever
6,792,979 B2 9/2004 Konya et al.
6,805,704 B1 10/2004 Hoyns
6,830,588 B2 12/2004 Furukawa et al.
6,887,215 B2 5/2005 McWeeney
6,887,270 B2 5/2005 Miller et al.
6,921,414 B2 7/2005 Klumb et al.
6,926,734 B1 8/2005 Klein
6,939,372 B2 9/2005 Dong
6,941,950 B2 9/2005 Wilson et al.
6,949,125 B2 9/2005 Robertson
6,974,473 B2 12/2005 Barclay et al.
6,982,740 B2 1/2006 Adair et al.
6,982,742 B2 1/2006 Adair et al.
6,997,952 B2 2/2006 Furukawa et al.
7,004,965 B2 2/2006 Gross
7,011,094 B2 3/2006 Rapacki et al.
7,018,401 B1 3/2006 Hyodoh et al.

(56) References Cited

U.S. PATENT DOCUMENTS

| | | | |
|---|---|---|---|
| 7,029,495 | B2 | 4/2006 | Stinson |
| 7,033,385 | B2 | 4/2006 | Eder et al. |
| 7,033,387 | B2 | 4/2006 | Zadno Azizi et al. |
| 7,044,981 | B2 | 5/2006 | Liu et al. |
| 7,048,014 | B2 | 5/2006 | Hyodoh et al. |
| 7,063,720 | B2 | 6/2006 | Iki et al. |
| 7,066,952 | B2 | 6/2006 | Igaki |
| 7,094,248 | B2 | 8/2006 | Bachinski et al. |
| 7,112,226 | B2 | 9/2006 | Gellman |
| 7,118,600 | B2 | 10/2006 | Dua et al. |
| 7,169,175 | B2 | 1/2007 | Cottone et al. |
| 7,192,440 | B2 | 3/2007 | Andreas et al. |
| 7,211,095 | B2 | 5/2007 | Bachinski et al. |
| 7,214,229 | B2 | 5/2007 | Mitchell et al. |
| 7,226,473 | B2 | 6/2007 | Brar et al. |
| 7,276,077 | B2 | 10/2007 | Azizi et al. |
| 7,294,146 | B2 | 11/2007 | Chew et al. |
| 7,309,352 | B2 | 12/2007 | Eder et al. |
| 7,316,663 | B2 | 1/2008 | Whitmore |
| 7,326,240 | B1 | 2/2008 | Caro et al. |
| 7,331,988 | B2 | 2/2008 | Igaki |
| 7,331,991 | B2 | 2/2008 | Kheradvar et al. |
| 7,335,226 | B2 | 2/2008 | Igaki |
| 7,347,868 | B2 | 3/2008 | Burnett et al. |
| 7,374,564 | B2 | 5/2008 | Brown |
| 7,410,665 | B2 | 8/2008 | Ragheb et al. |
| 7,468,052 | B2 | 12/2008 | Brar et al. |
| 7,470,247 | B2 | 12/2008 | Aliski et al. |
| 7,491,229 | B2 | 2/2009 | Eder et al. |
| 7,507,218 | B2 | 3/2009 | Aliski et al. |
| 7,507,247 | B2 | 3/2009 | Huxel et al. |
| 7,582,108 | B2 | 9/2009 | Hierlemann et al. |
| 7,611,533 | B2 | 11/2009 | Bates et al. |
| 7,632,297 | B2 | 12/2009 | Gross |
| 7,632,299 | B2 | 12/2009 | Weber |
| 7,682,381 | B2 | 3/2010 | Rakos et al. |
| 7,794,494 | B2 | 9/2010 | Sahatjian et al. |
| 7,799,070 | B2 | 9/2010 | Bates et al. |
| 7,828,715 | B2 | 11/2010 | Haverfield |
| 7,842,098 | B2 | 11/2010 | Rioux et al. |
| 7,846,202 | B2 | 12/2010 | Bates et al. |
| 7,850,705 | B2 | 12/2010 | Bachinski et al. |
| 7,862,605 | B2 | 1/2011 | Ragheb et al. |
| 7,862,607 | B2 | 1/2011 | McDermott et al. |
| 7,867,275 | B2 | 1/2011 | Bates et al. |
| 7,871,367 | B2 | 1/2011 | Anderson et al. |
| 7,878,972 | B2 | 2/2011 | D'Amelio et al. |
| 7,882,841 | B2 | 2/2011 | Aljuri et al. |
| 7,896,914 | B2 | 3/2011 | Bates et al. |
| 7,922,650 | B2 | 4/2011 | McWeeney et al. |
| 7,942,917 | B2 | 5/2011 | Nowak |
| 7,955,372 | B2 | 6/2011 | Butterwick et al. |
| 7,963,990 | B2 | 6/2011 | Johnson |
| 7,993,391 | B2 | 8/2011 | Stinson |
| 7,998,187 | B2 | 8/2011 | Hartley et al. |
| 8,007,540 | B2 | 8/2011 | Robertson |
| 8,007,702 | B2 | 8/2011 | Gellman |
| 8,016,742 | B2 | 9/2011 | Whalen et al. |
| 8,016,880 | B2 | 9/2011 | Cook et al. |
| 8,021,384 | B2 | 9/2011 | Weiss et al. |
| 8,029,557 | B2 | 10/2011 | Sobrino-Serrano et al. |
| 8,043,359 | B2 | 10/2011 | Edin |
| 8,052,670 | B2 | 11/2011 | Sachdeva et al. |
| 8,066,759 | B2 | 11/2011 | Weber et al. |
| 8,070,795 | B2 | 12/2011 | Hashimoto et al. |
| 8,070,824 | B2 | 12/2011 | Burnett et al. |
| 8,088,170 | B2 | 1/2012 | Whitmore |
| 8,092,864 | B2 | 1/2012 | Isch et al. |
| 8,101,275 | B2 | 1/2012 | Schüssler et al. |
| 8,105,666 | B2 | 1/2012 | Finley |
| 8,109,990 | B2 | 2/2012 | Paul et al. |
| 8,137,687 | B2 | 3/2012 | Chen et al. |
| 8,145,321 | B2 | 3/2012 | Gross |
| 8,158,187 | B2 | 4/2012 | Chen et al. |
| 8,160,678 | B2 | 4/2012 | Cropper et al. |
| 8,182,459 | B2 | 5/2012 | Dann et al. |
| 8,197,529 | B2 | 6/2012 | Cully et al. |
| 8,206,436 | B2 | 6/2012 | Mangiardi et al. |
| 8,221,505 | B2 | 7/2012 | Skerven |
| 8,226,704 | B2 | 7/2012 | Caro et al. |
| 8,236,043 | B2 | 8/2012 | Caro et al. |
| 8,241,548 | B2 | 8/2012 | Gellman |
| 8,257,433 | B2 | 9/2012 | Bates et al. |
| 8,282,678 | B2 | 10/2012 | Yachia et al. |
| 8,287,589 | B2 | 10/2012 | Otto et al. |
| 8,287,602 | B2 | 10/2012 | Daignault et al. |
| 8,308,629 | B2 | 11/2012 | Watschke et al. |
| 8,328,865 | B2 | 12/2012 | Bales et al. |
| 8,333,799 | B2 | 12/2012 | Bales et al. |
| 8,343,207 | B2 | 1/2013 | Rakos et al. |
| 8,371,998 | B2 | 2/2013 | Haverfield |
| 8,372,138 | B2 | 2/2013 | Jordan |
| 8,388,676 | B2 | 3/2013 | Stinson |
| 8,409,270 | B2 | 4/2013 | Clerc et al. |
| 8,414,635 | B2 | 4/2013 | Hyodoh et al. |
| 8,419,786 | B2 | 4/2013 | Cottone et al. |
| 8,463,005 | B2 | 6/2013 | Erbel et al. |
| 8,465,453 | B2 | 6/2013 | Sandhu et al. |
| 8,465,551 | B1 | 6/2013 | Wijay et al. |
| 8,475,516 | B2 | 7/2013 | Paul et al. |
| 8,485,965 | B2 * | 7/2013 | Ito ........................ A61B 1/0055 600/113 |
| 8,487,284 | B2 | 7/2013 | Tateshima et al. |
| 8,500,793 | B2 | 8/2013 | Zipse et al. |
| 8,500,821 | B2 | 8/2013 | Sobrino-Serrano et al. |
| 8,512,219 | B2 | 8/2013 | Ferren et al. |
| 8,523,936 | B2 | 9/2013 | Schmid et al. |
| 8,556,956 | B2 | 10/2013 | Cully et al. |
| 8,568,643 | B2 | 10/2013 | Gellman |
| 8,579,988 | B2 | 11/2013 | Burnett et al. |
| 8,585,730 | B2 | 11/2013 | Eaton et al. |
| 8,585,731 | B2 | 11/2013 | Abbate et al. |
| 8,591,569 | B2 | 11/2013 | Shin et al. |
| 8,608,639 | B2 | 12/2013 | Bartning et al. |
| 8,609,123 | B2 | 12/2013 | Hossainy et al. |
| 8,647,379 | B2 | 2/2014 | McDermott et al. |
| 8,652,197 | B2 | 2/2014 | Paul et al. |
| 8,672,996 | B2 | 3/2014 | Nelson et al. |
| 8,673,020 | B2 | 3/2014 | Sobrino-Serrano et al. |
| 8,674,035 | B2 | 3/2014 | Padsalgikar |
| 8,678,046 | B2 | 3/2014 | Melder et al. |
| 8,690,817 | B2 | 4/2014 | Assaf et al. |
| 8,691,264 | B2 | 4/2014 | Li et al. |
| 8,696,735 | B2 | 4/2014 | Caro et al. |
| 8,696,736 | B2 | 4/2014 | Yachia et al. |
| 8,702,788 | B2 | 4/2014 | Kheradvar et al. |
| 8,708,953 | B2 | 4/2014 | Salahieh et al. |
| 8,715,337 | B2 | 5/2014 | Chuter |
| 8,764,847 | B2 | 7/2014 | Knapp |
| 8,784,465 | B2 | 7/2014 | Sahatjian et al. |
| 8,784,473 | B2 | 7/2014 | Tupil et al. |
| 8,784,476 | B2 | 7/2014 | Caro et al. |
| 8,801,593 | B2 | 8/2014 | Haverfield |
| 8,801,770 | B2 | 8/2014 | Takayuki et al. |
| 8,808,354 | B2 | 8/2014 | Caro et al. |
| 8,834,338 | B2 | 9/2014 | Srivastava et al. |
| 8,834,492 | B2 | 9/2014 | McLean et al. |
| 8,845,599 | B2 | 9/2014 | Teague et al. |
| 8,852,265 | B2 | 10/2014 | Clerc et al. |
| 8,876,880 | B2 | 11/2014 | Hyodoh et al. |
| 8,920,513 | B2 | 12/2014 | Rickner |
| 8,928,746 | B1 | 1/2015 | Stevrin et al. |
| 8,936,634 | B2 | 1/2015 | Irwin et al. |
| 9,149,176 | B2 | 10/2015 | Greenberg et al. |
| 9,186,052 | B1 | 11/2015 | Adair et al. |
| 9,358,076 | B2 | 6/2016 | Moll et al. |
| 2001/0010007 | A1 | 7/2001 | Bachinski et al. |
| 2001/0010015 | A1 | 7/2001 | Hijlkema |
| 2001/0018611 | A1 | 8/2001 | Solem et al. |
| 2001/0029660 | A1 | 10/2001 | Johnson |
| 2002/0007206 | A1 | 1/2002 | Bui et al. |
| 2002/0007222 | A1 | 1/2002 | Desai |
| 2002/0035391 | A1 | 3/2002 | Mikus et al. |
| 2002/0077693 | A1 | 6/2002 | Barclay et al. |

(56) References Cited

U.S. PATENT DOCUMENTS

2002/0077696 A1 6/2002 Zadno Azizi et al.
2002/0082679 A1 6/2002 Sirhan et al.
2002/0082682 A1 6/2002 Barclay et al.
2002/0095209 A1 7/2002 Azizi et al.
2002/0120327 A1 8/2002 Cox et al.
2002/0123789 A1 9/2002 Francis et al.
2002/0143390 A1 10/2002 Ishii
2002/0151967 A1 10/2002 Mikus et al.
2002/0161114 A1 10/2002 Gunatillake et al.
2002/0173809 A1 11/2002 Fleischman et al.
2002/0173810 A1 11/2002 Bachinski et al.
2003/0028244 A1 2/2003 Bates et al.
2003/0040772 A1 2/2003 Hyodoh et al.
2003/0055313 A1 3/2003 Anderson et al.
2003/0069647 A1 4/2003 Desmond, III et al.
2003/0074052 A1 4/2003 Besselink
2003/0105515 A1 6/2003 Skubitz et al.
2003/0135268 A1 7/2003 Desai
2003/0153971 A1 8/2003 Chandrasekaran
2003/0153972 A1 8/2003 Helmus
2003/0195609 A1 10/2003 Berenstein et al.
2003/0229364 A1 12/2003 Seiba
2004/0054377 A1 3/2004 Foster et al.
2004/0078088 A1 4/2004 Gellman
2004/0087886 A1 5/2004 Gellman
2004/0087997 A1 5/2004 Brenneman
2004/0088043 A1 5/2004 Klein
2004/0092892 A1 5/2004 Kagan et al.
2004/0098119 A1 5/2004 Wang
2004/0106975 A1 6/2004 Solovay et al.
2004/0153142 A1 8/2004 Klumb et al.
2004/0167635 A1 8/2004 Yachia et al.
2004/0171747 A1 9/2004 Zhong
2004/0199262 A1 10/2004 Dua et al.
2004/0236414 A1 11/2004 Brar et al.
2004/0249441 A1 12/2004 Miller et al.
2005/0010275 A1 1/2005 Sahatjian et al.
2005/0021131 A1 1/2005 Venkatraman et al.
2005/0025752 A1 2/2005 Kutryk et al.
2005/0033314 A1 2/2005 Sakurai et al.
2005/0033399 A1 2/2005 Richter
2005/0038455 A1 2/2005 Bates et al.
2005/0049673 A1 3/2005 Andreas et al.
2005/0049681 A1 3/2005 Greenhalgh et al.
2005/0075721 A1 4/2005 Klein
2005/0096750 A1 5/2005 Kagan et al.
2005/0131515 A1 6/2005 Cully et al.
2005/0131525 A1 6/2005 Hartley
2005/0145253 A1 7/2005 Wilson et al.
2005/0163821 A1 7/2005 Sung et al.
2005/0166925 A1 8/2005 Wilson et al.
2005/0171599 A1 8/2005 White
2005/0182477 A1 8/2005 White
2005/0187428 A1 8/2005 Rinman
2005/0187510 A1 8/2005 McWeeney
2005/0187609 A1 8/2005 Brar et al.
2005/0222677 A1 10/2005 Bates et al.
2005/0228417 A1 10/2005 Teitelbaum et al.
2005/0240141 A1 10/2005 Aliski et al.
2005/0240278 A1 10/2005 Aliski et al.
2006/0004436 A1 1/2006 Amarant et al.
2006/0030753 A1 2/2006 Boutillette et al.
2006/0058869 A1 3/2006 Olson et al.
2006/0076023 A1 4/2006 Rapacki et al.
2006/0095058 A1* 5/2006 Sivan .................... A61B 17/08 606/174
2006/0136033 A1 6/2006 Hermann et al.
2006/0136034 A1 6/2006 Modesitt et al.
2006/0136035 A1 6/2006 Hermann et al.
2006/0142794 A1 6/2006 Lendlein et al.
2006/0167538 A1 7/2006 Rucker
2006/0211984 A1 9/2006 Blank et al.
2006/0235504 A1 10/2006 Gonzales
2006/0246210 A1 11/2006 Iki et al.
2006/0253190 A1 11/2006 Kuo
2007/0005125 A1 1/2007 Berenstein et al.
2007/0005148 A1 1/2007 Barofsky et al.
2007/0014773 A1 1/2007 Matheny et al.
2007/0014871 A1 1/2007 Matheny
2007/0014873 A1 1/2007 Matheny
2007/0027285 A1 2/2007 Gunatillake et al.
2007/0043433 A1 2/2007 Chandrasekaran
2007/0050018 A1 3/2007 Wainwright
2007/0053952 A1 3/2007 Chen et al.
2007/0112411 A1 5/2007 Obermiller et al.
2007/0141100 A1 6/2007 Sung et al.
2007/0141107 A1 6/2007 Kutryk et al.
2007/0150045 A1 6/2007 Ferrera
2007/0173924 A1 7/2007 Gelbart et al.
2007/0213805 A1 9/2007 Schaeffer et al.
2007/0219616 A1 9/2007 Modesitt et al.
2007/0250148 A1 10/2007 Perry et al.
2007/0293932 A1 12/2007 Zilla et al.
2008/0009662 A1 1/2008 Bartning et al.
2008/0009814 A1 1/2008 Bartning et al.
2008/0015633 A1 1/2008 Abbott et al.
2008/0033230 A1 2/2008 Bartning et al.
2008/0039921 A1 2/2008 Wallsten et al.
2008/0039931 A1 2/2008 Jelle et al.
2008/0045881 A1 2/2008 Teitelbaum et al.
2008/0050418 A1 2/2008 Ranade et al.
2008/0077174 A1 3/2008 Mische
2008/0082121 A1 4/2008 Chu
2008/0086214 A1 4/2008 Hardin et al.
2008/0103412 A1 5/2008 Chin
2008/0103440 A1 5/2008 Ferren et al.
2008/0109067 A1 5/2008 Caro et al.
2008/0132988 A1 6/2008 Jordan
2008/0145396 A1 6/2008 Bates et al.
2008/0145399 A1 6/2008 Bates et al.
2008/0183278 A1 7/2008 Atanasoska et al.
2008/0183299 A1 7/2008 Monga et al.
2008/0195189 A1 8/2008 Asgari
2008/0195196 A1 8/2008 Asgari
2008/0200976 A1 8/2008 Asgari
2008/0208083 A1 8/2008 Lin et al.
2008/0208321 A1 8/2008 Venkatraman et al.
2008/0220040 A1 9/2008 Cheng et al.
2008/0220048 A1 9/2008 Chen et al.
2008/0241899 A1 10/2008 Rhee et al.
2008/0249552 A1 10/2008 Eliachar et al.
2008/0275550 A1 11/2008 Kheradvar et al.
2009/0018486 A1 1/2009 Goren et al.
2009/0030363 A1 1/2009 Gellman
2009/0030370 A1 1/2009 Nishtala et al.
2009/0035350 A1 2/2009 Stankus et al.
2009/0048537 A1 2/2009 Lydon et al.
2009/0081271 A1 3/2009 Clarke et al.
2009/0118817 A1 5/2009 Sandhu et al.
2009/0149947 A1 6/2009 Frohwitter
2009/0163934 A1 6/2009 Raschdorf et al.
2009/0177288 A1 7/2009 Wallsten
2009/0182206 A1 7/2009 Najafi et al.
2009/0192588 A1 7/2009 Shin et al.
2009/0192592 A1 7/2009 Asgari
2009/0198179 A1 8/2009 Abbate et al.
2009/0204200 A1 8/2009 Bales et al.
2009/0210045 A1 8/2009 Sørensen et al.
2009/0248141 A1 10/2009 Shandas et al.
2009/0281635 A1 11/2009 Li et al.
2009/0287193 A1 11/2009 Desai et al.
2009/0326637 A1 12/2009 Hashimoto et al.
2010/0042203 A1 2/2010 Cottone et al.
2010/0076574 A1 3/2010 Gellman
2010/0082093 A1 4/2010 Weber
2010/0092535 A1 4/2010 Cook et al.
2010/0094327 A1 4/2010 Milsom et al.
2010/0100170 A1 4/2010 Tan et al.
2010/0121461 A1 5/2010 Sobrino-Serrano et al.
2010/0122698 A1 5/2010 Shaffer et al.
2010/0130815 A1* 5/2010 Gross ........................ A61F 2/92 600/30
2010/0145433 A1 6/2010 Anukhin et al.
2010/0174364 A1 7/2010 Hoffman et al.

(56) References Cited

U.S. PATENT DOCUMENTS

| | | | |
|---|---|---|---|
| 2010/0204775 | A1 | 8/2010 | Edwin |
| 2010/0286760 | A1 | 11/2010 | Beach et al. |
| 2010/0331954 | A1 | 12/2010 | Sahatjian et al. |
| 2011/0040366 | A1 | 2/2011 | Goetz et al. |
| 2011/0046723 | A1 | 2/2011 | Bates et al. |
| 2011/0071613 | A1 | 3/2011 | Wood et al. |
| 2011/0077676 | A1 | 3/2011 | Sivan et al. |
| 2011/0093007 | A1 | 4/2011 | Abbott et al. |
| 2011/0118820 | A1 | 5/2011 | Sandhu et al. |
| 2011/0125251 | A1 | 5/2011 | Cottone et al. |
| 2011/0130834 | A1 | 6/2011 | Wilson et al. |
| 2011/0160836 | A1 | 6/2011 | Behan |
| 2011/0172763 | A1 | 7/2011 | Ndondo-Lay |
| 2011/0190662 | A1 | 8/2011 | McWeeney |
| 2011/0218387 | A1 | 9/2011 | Lamson et al. |
| 2011/0251482 | A1 | 10/2011 | Kellerman et al. |
| 2011/0264116 | A1 | 10/2011 | Kocur et al. |
| 2011/0295353 | A1 | 12/2011 | Harris et al. |
| 2012/0010645 | A1 | 1/2012 | Feld |
| 2012/0059486 | A1 | 3/2012 | Sobrino-Serrano et al. |
| 2012/0083820 | A1 | 4/2012 | Carman et al. |
| 2012/0143306 | A1 | 6/2012 | Cully et al. |
| 2012/0150275 | A1 | 6/2012 | Shaw-Klein |
| 2012/0158155 | A1 | 6/2012 | Shin |
| 2012/0165928 | A1 | 6/2012 | Nitzan et al. |
| 2012/0172970 | A1 | 7/2012 | Cottone et al. |
| 2012/0191175 | A1 | 7/2012 | Costa et al. |
| 2012/0191177 | A1 | 7/2012 | Costa et al. |
| 2012/0226341 | A1 | 9/2012 | Schreck et al. |
| 2012/0232459 | A1 | 9/2012 | Dann et al. |
| 2012/0238803 | A1 | 9/2012 | Lund |
| 2012/0253451 | A1 | 10/2012 | Sahatjian et al. |
| 2012/0283811 | A1 | 11/2012 | Neilan |
| 2012/0316656 | A1 | 12/2012 | Deal et al. |
| 2013/0030521 | A1 | 1/2013 | Nitzan et al. |
| 2013/0041208 | A1 | 2/2013 | Anderson et al. |
| 2013/0060238 | A1 | 3/2013 | Lavelle |
| 2013/0079586 | A1 | 3/2013 | Knipfer |
| 2013/0090719 | A1 | 4/2013 | Bales et al. |
| 2013/0090721 | A1 | 4/2013 | Bales et al. |
| 2013/0116768 | A1 | 5/2013 | Rakos et al. |
| 2013/0123934 | A1 | 5/2013 | Azar |
| 2013/0131778 | A1 | 5/2013 | Igaki et al. |
| 2013/0131780 | A1 | 5/2013 | Armstrong et al. |
| 2013/0144372 | A1 | 6/2013 | Wood et al. |
| 2013/0150951 | A1 | 6/2013 | Jordan |
| 2013/0158675 | A1 | 6/2013 | Hutchins et al. |
| 2013/0165742 | A1 | 6/2013 | Bartning et al. |
| 2013/0172673 | A1 | 7/2013 | Kennedy et al. |
| 2013/0173016 | A1 | 7/2013 | Devereux |
| 2013/0184809 | A1 | 7/2013 | Stinson |
| 2013/0204347 | A1 | 8/2013 | Armstrong et al. |
| 2013/0226282 | A1 | 8/2013 | Ahn et al. |
| 2013/0237907 | A1 | 9/2013 | Bacher et al. |
| 2013/0253662 | A1 | 9/2013 | Lamson et al. |
| 2013/0267772 | A1 | 10/2013 | Catanese, III et al. |
| 2013/0345786 | A1 | 12/2013 | Behan |
| 2014/0004503 | A1 | 1/2014 | Cima et al. |
| 2014/0010858 | A1 | 1/2014 | Stankus et al. |
| 2014/0012192 | A1 | 1/2014 | Bar-On et al. |
| 2014/0025158 | A1 | 1/2014 | Liddy et al. |
| 2014/0058496 | A1 | 2/2014 | Tranquillo et al. |
| 2014/0067042 | A1 | 3/2014 | Schmid et al. |
| 2014/0074238 | A1 | 3/2014 | Abbate et al. |
| 2014/0079755 | A1 | 3/2014 | Eaton et al. |
| 2014/0107062 | A1 | 4/2014 | Shenoy |
| 2014/0107765 | A1 | 4/2014 | Cottone et al. |
| 2014/0114389 | A1 | 4/2014 | Hyodoh et al. |
| 2014/0114432 | A1 | 4/2014 | Shalon |
| 2014/0114434 | A1 | 4/2014 | Cottone et al. |
| 2014/0121585 | A1 | 5/2014 | Baker et al. |
| 2014/0142721 | A1 | 5/2014 | Robertson et al. |
| 2014/0148896 | A1 | 5/2014 | McDermott et al. |
| 2014/0155987 | A1 | 6/2014 | Paul et al. |
| 2014/0172065 | A1 | 6/2014 | Lavelle et al. |
| 2014/0172118 | A1 | 6/2014 | Pendleton et al. |
| 2014/0188029 | A1 | 7/2014 | Assaf et al. |
| 2014/0188249 | A1 | 7/2014 | Pendleton et al. |
| 2014/0200677 | A1 | 7/2014 | Sobrino-Serrano et al. |
| 2014/0214175 | A1 | 7/2014 | Barron et al. |
| 2014/0277564 | A1 | 9/2014 | Windheuser et al. |
| 2014/0288627 | A1 | 9/2014 | Ouellette et al. |
| 2014/0288630 | A1 | 9/2014 | Gerdts et al. |
| 2014/0288636 | A1 | 9/2014 | Headley et al. |
| 2014/0288637 | A1 | 9/2014 | Clerc et al. |
| 2014/0316512 | A1 | 10/2014 | Takayuki et al. |
| 2014/0324144 | A1 | 10/2014 | Ye et al. |
| 2014/0330364 | A1 | 11/2014 | Tupil et al. |
| 2014/0343243 | A1 | 11/2014 | Padsalgikar |
| 2014/0350343 | A1 | 11/2014 | Kim |
| 2015/0018602 | A1 | 1/2015 | Presthus et al. |
| 2015/0025652 | A1 | 1/2015 | McLean et al. |
| 2015/0039078 | A1 | 2/2015 | Bales et al. |
| 2015/0257908 | A1 | 9/2015 | Chao et al. |
| 2016/0015509 | A1 | 1/2016 | McDonough |
| 2016/0213230 | A1 | 7/2016 | Adair et al. |
| 2017/0000598 | A1 | 1/2017 | Bachar |
| 2017/0042678 | A1 | 2/2017 | Ganesan et al. |
| 2017/0135830 | A1 | 5/2017 | Harkin et al. |
| 2017/0172677 | A1 | 6/2017 | Kernbaum et al. |
| 2017/0172678 | A1 | 6/2017 | Dewaele et al. |
| 2018/0140419 | A1 | 5/2018 | Kerr et al. |
| 2018/0318114 | A1 | 11/2018 | Huang et al. |
| 2019/0038443 | A1 | 2/2019 | Sicotte et al. |
| 2019/0117423 | A1 | 4/2019 | Chao et al. |
| 2019/0307548 | A1 | 10/2019 | Sicotte et al. |
| 2020/0038213 | A1 | 2/2020 | Bly et al. |
| 2020/0323618 | A1 | 10/2020 | Bly et al. |

FOREIGN PATENT DOCUMENTS

| | | | |
|---|---|---|---|
| CN | 204192562 | U | 3/2015 |
| CN | 104161493 | B | 4/2016 |
| CN | 104545772 | B | 8/2016 |
| DE | 103 57 742 | A1 | 3/2005 |
| EP | 2 839 872 | A1 | 2/2015 |
| WO | WO 98/22159 | A2 | 5/1998 |
| WO | WO 02/032321 | A1 | 4/2002 |
| WO | WO 2005/016185 | A1 | 2/2005 |
| WO | WO 2010/140080 | A2 | 12/2010 |
| WO | WO 2014/019321 | A1 | 2/2014 |
| WO | WO 2016/143457 | A1 | 9/2016 |
| WO | WO 2017/184887 | A1 | 10/2017 |
| WO | WO 2019/222481 | A1 | 11/2019 |

OTHER PUBLICATIONS

EP, 17879206.5 Supplementary Search Report, Jun. 8, 2020.

EP, 2089107.4 Extended Search Report, Nov. 23, 2023.

WO, PCT/US2019/032637 ISR and Written Opinion, Sep. 5, 2019.

WO, PCT/US2020/060989 ISR and Written Opinion, Mar. 25, 2021.

* cited by examiner

SYSTEMS, DEVICES, AND METHODS FOR THE ACCURATE DEPLOYMENT AND IMAGING OF AN IMPLANT IN THE PROSTATIC URETHRA

CROSS-REFERENCE TO RELATED APPLICATIONS

This application is a continuation of U.S. patent application Ser. No. 16/951,256, filed Nov. 18, 2020, now issued as U.S. Pat. No. 11,890,213, which claims priority to, and the benefit of, U.S. Provisional Application No. 62/937,625, filed Nov. 19, 2019, both of which are hereby expressly incorporated by reference in their entireties for all purposes.

STATEMENT OF GOVERNMENT SPONSOR RESEARCH

This invention was made with government support under NIH SBIR Phase II R44DK124094 awarded by the National Institutes of Health. The government has certain rights in the invention.

FIELD

The subject matter described herein relates to systems, devices, and methods for delivery or deployment of an implant into the prostatic urethra, more specifically, delivery in an atraumatic and minimally-invasive manner through the tortuous bends of the male urethra.

BACKGROUND

There are numerous clinical reasons for placement of an implant into the prostatic urethra, such as for treatment of urinary retention associated with benign prostatic hyperplasia (BPH), blockages from prostate cancer, bladder cancer, urinary tract injury, prostatitis, bladder sphincter dyssynergia, benign or malignant urethral stricture, and other conditions for which treatment is desired. Due to the naturally complex and tortuous anatomical geometry, patient-to-patient geometric and tissue variability, and anatomical restrictions associated with those conditions, accurate and consistent placement of an implant into the prostatic urethral lumen has proven challenging. Furthermore, complex challenges are presented in the design and/or fabrication of systems with sufficient flexibility to deliver such an implant in a minimally-invasive manner. For these and other reasons, needs exist for improved systems, devices, and methods of implant delivery to the prostatic urethra.

SUMMARY

Provided herein are a number of example embodiments of delivery systems for delivering or deploying implants within the prostatic urethra or other parts of the body, and methods related thereto. Embodiments of the delivery system can include a delivery device insertable into the prostatic urethra and a proximal control device coupled with the delivery device and configured to control deployment of one or more implants from the delivery device. In some embodiments, the delivery device can include multiple tubular components each having various functions described in more detail herein. Embodiments of the delivery system have imaging capabilities. Multiple embodiments of implants for use with the delivery systems are also described, as are various implanted placements of those implants.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The subject matter presented herein is described in the context of delivery or deployment of one or more implants within the prostatic urethra. The purpose for deployment of the implant(s) in the prostatic urethra can vary. The embodiments described herein are particularly suited for treatment of BPH, but they are not limited to such. Other conditions for which these embodiments can be used include, but are not limited to, treatment of blockages from prostate cancer, bladder cancer, urinary tract injury, prostatitis, bladder sphincter dyssynergia, and/or benign or malignant urethral stricture. Further, these embodiments can have applicability for deployment of one or more implants in other locations of the urinary tract or in the bladder, as well as other biological lumens, cavities, or spaces, such as the human vasculature, cardiac system, pulmonary system, or gastro-intestinal tract, including locations within the heart, stomach, intestines, liver, spleen, pancreas, and kidney.

Figure 1A:
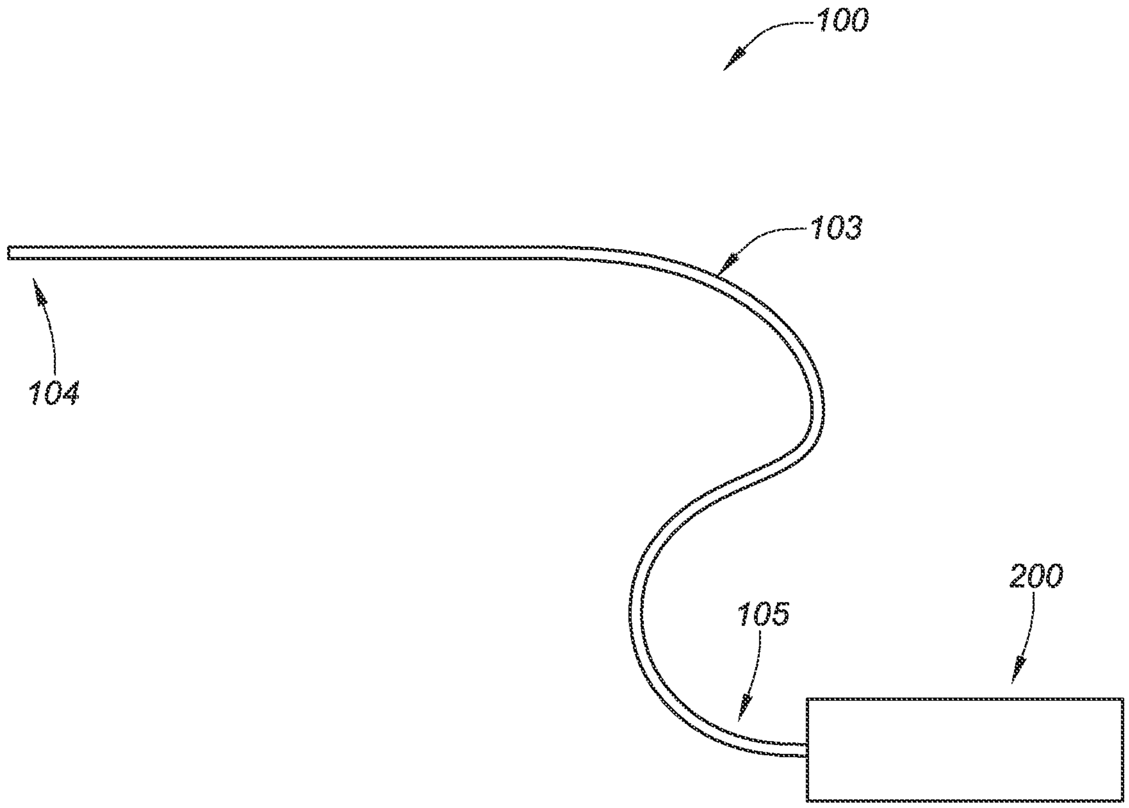
FIG. 1A is a block diagram depicting an example embodiment of a delivery system.

FIG. 1A is a block diagram depicting an example embodiment of delivery system 100 having an elongate delivery device 103 coupled with a proximal control device 200. A distal end region 104 is adapted to be inserted into the patient's urethra (or other lumen or body cavity of the patient) through the urethral orifice. Distal end region 104 preferably has an atraumatic configuration (e.g., relatively soft and rounded) to minimize irritation or trauma to the patient. Elongate delivery device 103 carries or houses one or more implants 102 (not shown) to be delivered or deployed within or adjacent to the prostatic urethra. A proximal end region 105 of delivery device 103 is coupled with proximal control device 200, which remains outside of the patient's body and is configured to be used by the physician or other healthcare professional to control the delivery of one or more implants 102.

Example Embodiments of Delivery Devices and Related Methods

Figure 1B:
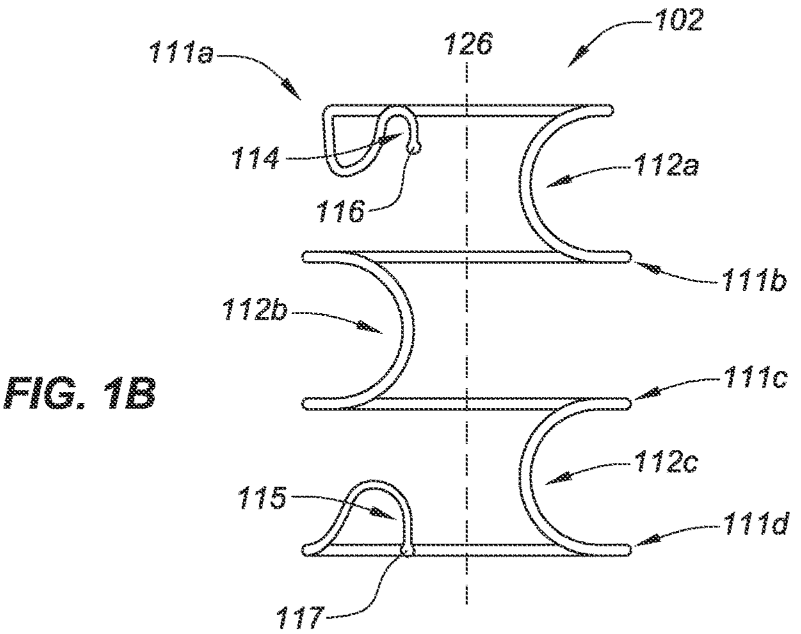
FIGS. 1B, 1C, and 1D are side, end, and perspective views, respectively, depicting an example embodiment of an implant.
Figure 1C:
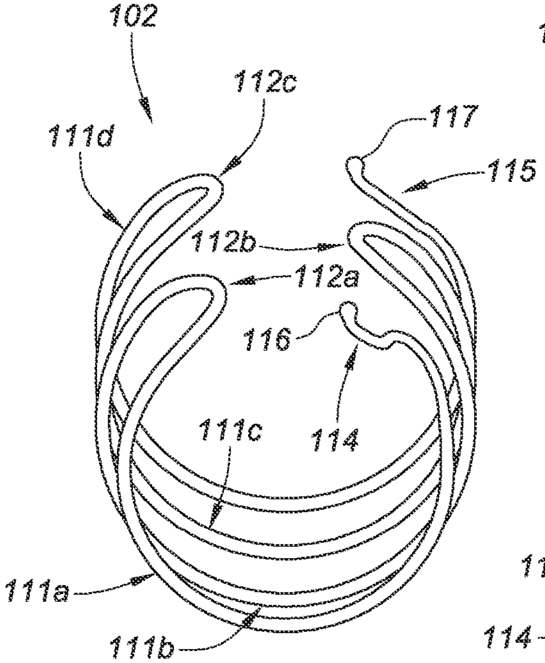
Figure 1D:
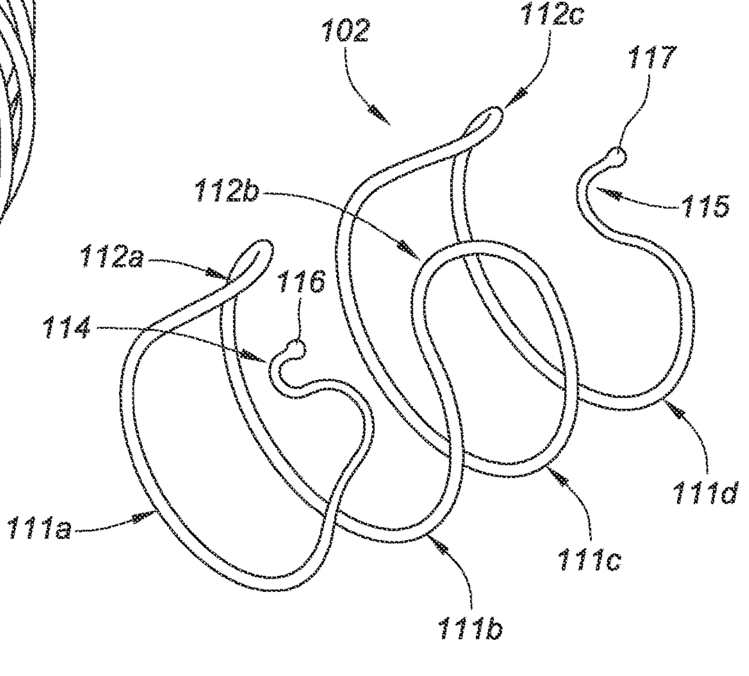

FIGS. 1B, 1C, and 1D are side, end, and perspective views, respectively, depicting an example embodiment of implant 102 in an at-rest configuration. Implantable device 102 is biased towards the at-rest configuration depicted here and is deformable between the at-rest configuration and a relatively more elongate housed (or delivery) configuration (e.g., see FIG. 3A) for housing implant 102 within delivery device 103. The housed configuration can be a straight or lineated state with minimal curvature. The at-rest configuration has a relatively greater lateral width, and a relatively shorter longitudinal length than the housed configuration. Upon exiting an open end of delivery device 103, implant 102 is free to transition its shape back towards that of the at-rest configuration although restraints imparted by the patient's urethral wall may prevent implant 102 from fully reaching the at-rest configuration. Because implant 102 is biased towards the at-rest configuration, implant 102 is configured to automatically expand when freed from the restraint of delivery device 103, and can be referred to as "self-expanding." The shape of implant 102 in its deployed state within, e.g., the patient's urethra, can be referred to as the deployed configuration, and will often be a shape that is deformed from the at-rest configuration by the surrounding tissue, although the deployed configuration can be the same as the at-rest configuration.

Implant 102 can be configured in numerous different ways, including any and all of those implant configurations described in U.S. Patent Publ. No. 2015/0257908 and/or Int'l Publ. No. WO 2017/184887, both of which are incorporated by reference herein for all purposes.

Implant 102 can be formed from one or more discrete bodies (e.g., wires, ribbons, tubular members) of varying geometries. Referring to the embodiment of FIGS. 1B-1D, implant 102 has a main body formed of only one single wire member set in a predetermined shape. Implant 102 can have two or more ring-shaped structures 111 (in this embodiment there are four: 111*a*, 111*b*, 111*c*, and 111*d*) with one or more interconnections 112 extending between each pair of adjacent ring-shaped structures 111 (in this embodiment there is one interconnection between each adjacent pair, for a total of three: 112*a*, 112*b*, and 112*c*). Each interconnection 112 extends from one ring-shaped structure 111 to an immediately adjacent ring-shaped structure 111. Each interconnection 112 can have a relatively straight shape (not shown) or a curved (e.g., semi-circular or semi-elliptical) shape as shown in FIGS. 1B-1D.

Ring-shaped structures 111 are configured to maintain the urethra in a fully or partially open state when expanded from the housed configuration. Device 100 can be manufactured in various sizes as desired, such that the width (e.g., diameter) of each ring-shaped structure 111 is slightly larger than the width of the urethra, and the length of each interconnection 112 determines the spacing between ring-shaped structures 111. Ring-shaped structures 111 can have the same or different widths. For example, in the embodiment depicted here, ring-shaped structure 111*a* has a relatively smaller width than structures 111*b*-111*d*, which have the same width. This can accommodate prostatic urethras that converge to a smaller geometry before the bladder neck.

Each ring-shaped structure 111 can be located or lie in a single plane, and in some embodiments that single plane can be oriented with a normal axis perpendicular to a central axis 124 of implant 102 (as depicted in FIG. 1B). In other embodiments, ring-shaped structures 111 can be located in multiple planes. Ring-shaped structures 111 can extend around central axis 126 to form a complete circle (e.g., a 360 degree revolution) or can form less than a complete circle (e.g., less than 360 degrees) as shown here. Although not limited to such, in many embodiments ring-shaped structures 111 extend between 270 and 360 degrees.

As can be seen from FIGS. 1B-1D, the geometry of implant 102 can have a cylindrical or substantially cylindrical outline shape with a circular or elliptical cross-section. In other embodiments, implant 102 can have a prismatic or substantially prismatic shape with triangular or substantially triangular cross-section, or otherwise.

Implant 102 can also include a distal engagement member 114 and a proximal engagement member 115 that are each configured to engage with elements of delivery device 103. Engagement with delivery device 103 can serve one or more purposes such as allowing control of the release of implant 102, allowing movement of the ends of implant 102 relative to each other, and/or allowing retrieval of implant 102 after deployment, e.g., in an instance where the physician desires to recapture implant 102 and redeploy implant 102 in a different position. In this embodiment, distal engagement member 114 is a wire-like extension from ring-shaped structure 111*a* that has a curved (e.g., S-like) shape for positioning an atraumatic end 116 (e.g., rounded, spherical, ballized) in a location suitable for engagement with delivery device 103 and thereby allow control of the distal end region of implant 102. Likewise, proximal engagement member 115 has a curved shape for positioning another atraumatic end 117 in a location suitable for engagement with delivery device 103 and thereby allow control of the proximal end region of implant 102. In other embodiments, distal engagement member 114 and proximal engagement member 115 can be configured such that the atraumatic ends 116 and 117 point in different directions. For example, atraumatic ends 116 and 117 can be pointing distally instead of proximally. In another embodiment, atraumatic ends 116 and 117 can be pointing in opposite directions (e.g., atraumatic end 116 can be pointing distally and atraumatic end 117 can be pointing proximally, and vice versa). In other embodiments, distal engagement member 114 and proximal engagement member 115 can be omitted, and delivery device 103 can couple with implant 102 at one or more other distal and/or proximal locations, such as on a ring-shaped structure 111 or interconnect 112. Moreover, an extension having an atraumatic end (similar to distal engagement member 114 and proximal engagement member 115) can be attached in the middle of implant 102 in order to provide an additional structure to control placement of the middle portion of the implant.

Figure 2A:
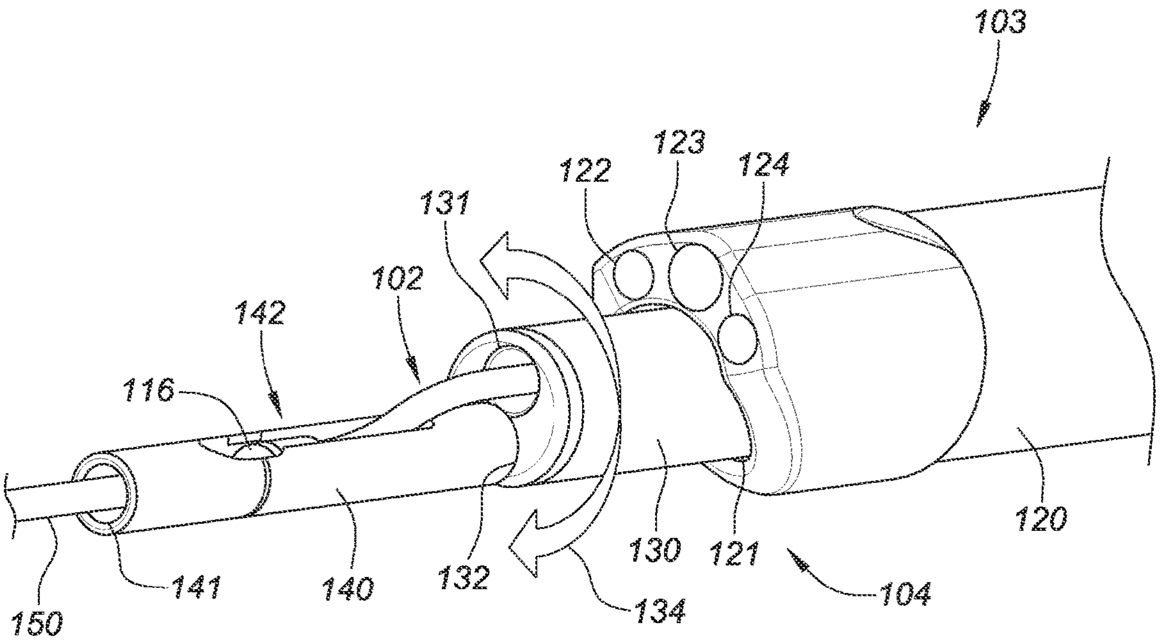
FIGS. 2A-2B are perspective views depicting example embodiments of a delivery system in different stages of deployment of an implant.

Delivery device 103 can include one or more elongate flexible members (e.g., 120, 130, 140, and 150 as described below), each having one or more inner lumens. Alternatively, one or more elongate flexible members of delivery device 103 can be a solid or a non-hollow member with no inner lumen. FIG. 2A is a perspective view depicting an example embodiment of distal end region 104 of a delivery device 103. In this embodiment, delivery device 103 includes a first elongate tubular member 120, a second elongate tubular member 130, a third elongate tubular member 140, and a fourth elongate tubular member 150. Delivery device 103 can vary and in other embodiments can include more or less tubular members.

In this embodiment, first elongate tubular member 120 is the outermost tubular member and is flexible yet provides support for members contained therein. First tubular member 120 is referred to herein as outer shaft 120 and can have one or more inner lumens. In this embodiment, outer shaft 120 includes a first inner lumen 121 housing second elongate tubular member 130, which is referred to herein as inner shaft 130. Outer shaft 120 and inner shaft 130 are each controllable independent of the other. Inner shaft 130 can slide distally and proximally within lumen 121 and is shown here partially extending from an open distal terminus of outer shaft 120.

In this embodiment, outer shaft 120 includes three additional lumens 122, 123, and 124. An illumination device (not shown) and an imaging device (not shown) can be housed in two of lumens 122-124 (e.g., lumens 122 and 123). The imaging device can utilize any desired type of imaging modality, such as optical or ultrasound imaging. In one example embodiment the imaging device utilizes a forward (distal) looking CMOS imager. The illumination device can be configured to provide adequate illumination for optical imaging, and in one embodiment includes one or more light emitting diodes (LEDs). In embodiments where illumination is not required, such as for ultrasound imaging, the illumination device and its respective lumen can be omitted or the lumen could be used for an alternative purpose, e.g., as an irrigation or flushing channel. The illumination device and/or the imaging device can each be fixedly secured at the distal terminuses of lumens 122 and 123, or each can be slidable within lumens 122 and 123 to allow advancement further distally from outer shaft 120 and/or retraction into outer shaft 120. In one example embodiment, the illumination device and the imaging device are mounted together and only a single lumen 122 or 123 is present for that purpose. The remaining lumen (e.g., lumen 124) can be configured as an irrigation or flush port from which fluid such as saline can be introduced to the urethra to flush the region and provide adequate fluid through which implant 102 and the surrounding prostatic urethra wall can be imaged. In one embodiment, the outer shaft may contain two separate lumens for fluid management. One lumen may be used for irrigation and the other lumen may be used for flushing.

Outer shaft 120 has a proximal end (not shown) coupled with proximal control device 200. Delivery device 103 can be configured to be steerable to navigate tortuous anatomy. Steerability can be unidirectional (e.g., using a single pull wire) or multidirectional (e.g., using two or more pull wires arranged at different radial locations about device 103) depending on the needs of the application. In some embodiments, the structures (e.g., pull wires) for steerability extend from distal end region 104 of delivery device 103 (e.g., where the distal ends of the pull wires are secured to a plate or other structure within distal end region 104) to proximal control device 200, where they can be manipulated by the user to steer delivery device 103. The steering structures can be located in one or more lumens of outer shaft 120, or can be coupled to or embedded within a sidewall of outer shaft 120. Delivery device 103 can be biased to deflect in a particular lateral direction (e.g., bend) such that device 103 automatically deflects in that manner and forces imparted to steer delivery device 103 are in opposition to this biased deflection. Other mechanisms for steering delivery device 103 can also be used. The steering mechanism may also be locked or adjusted during deployment of implant 102 to control the position of implant 102 within the anatomy (e.g., steering anteriorly during deployment may help place implant 102 in a more desirable anterior position).

Inner shaft 130 can include one or more inner lumens for housing one or more implants 102 and/or other components. In this embodiment, inner shaft 130 includes a first lumen 131 in which one or more implants 102 can be housed, and a second lumen 132 in which third elongate tubular member 140 can be housed. In this embodiment, third elongate tubular member 140 is configured to releasably couple with the distal end region of implant 102 and is referred to as a distal control member or tether 140. Distal control member 140 can be slidably advanced and/or retracted with respect to inner shaft 130. Distal control member 140 can include an inner lumen 141 that houses fourth elongate tubular member 150, which is shown here extending from an open distal terminus of distal control member 140. Fourth elongate tubular member 150 is configured to anchor delivery device 103 with respect to the patient's anatomy, e.g., to keep components of delivery device 103 stationary with respect to the anatomy during deployment of implant 102, and is referred to as anchor delivery member 150.

In the configuration depicted in FIG. 2A, anchor delivery member 150 is extended from lumen 141 of distal control member 140, and distal control member 140 along with inner shaft 130 are shown extended from lumen 121 of outer shaft 120. When delivery device 130 is advanced through the urethra, anchor delivery member 150 is preferably housed entirely within distal control member 140, and distal control member 140 along with inner shaft 130 are retracted from the positions shown in FIG. 2A such that they reside within lumen 121 of outer shaft 120 and do not extend from the open distal terminus of lumen 120. In other words, in some embodiments the open distal terminus of outer shaft 120 forms the distalmost structure of device 103 upon initial advancement through the urethra. This facilitates steering of delivery device 103 by outer shaft 120. The physician can advance distal end region 104 of delivery device 103 to be in proximity with the desired implantation site, or entirely into the patient's bladder. Anchor delivery member 150 can be exposed from the open distal terminus of distal control member 140, either by distally advancing anchor delivery member 150 further into the bladder, or if already present within the bladder, then by proximally retracting the other components of delivery device 103. At this point the anchor from anchor delivery member 150 can be deployed in the bladder.

Figure 2B:
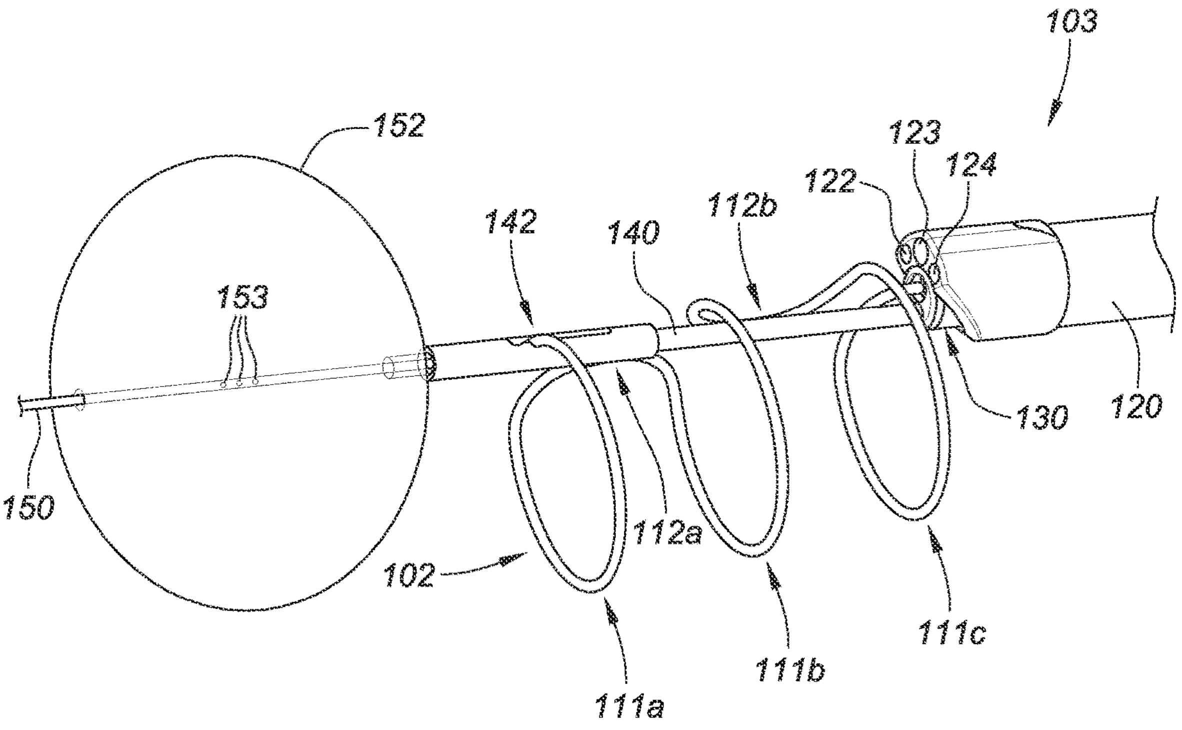

FIG. 2B is a perspective view depicting distal end region 104 of delivery device 103 with the various components deployed. In this embodiment, anchor delivery member 150 includes an anchor 152 in the form of an inflatable member or balloon.

Other embodiments of anchors 152 are described in International Application No. PCT/US19/32637, filed May 16, 2019, which is hereby incorporated by reference in its entirety for all purposes. Anchor 152 expands (or otherwise transitions) to a size greater than that of the bladder neck such that anchor 152 resists proximal retraction (e.g., a relatively light tension). In embodiments where anchor 152 is a balloon, that balloon can be an elastic or inelastic and inflatable with an inflation medium (e.g., air or liquid such as saline) introduced into balloon 152 through one or more inflation ports 153. Here three inflation ports 153 are located on the shaft of anchor delivery member 150 and communicate with an inflation lumen that extends proximally back to proximal control device 200, which can include a port for inflation with a syringe. Upon deployment of anchor 152, the physician can proximally retract delivery system 100 until anchor 152 is in contact with the bladder neck and/or wall (if not already).

The physician can use the imaging device of outer shaft 120 to move delivery device 103 proximally away from anchor 152 until the physician is in the desired position within the urethra to begin deployment of implant 102. A retainer 142 on distal control member 140 is releasably coupled with distal engagement member 114 of implant 102. The physician can position retainer 142 in a location along the length of the urethra where the physician desires the distal end of implant 102 to deploy. This can involve moving distal control member 140 and inner shaft 130, together, proximally and/or distally with respect to anchor delivery member 150. In another embodiment, the position of retainer 142 is fixed with respect to anchor 152 such that the longitudinal position of implant 102 within the anatomy is set by the system independently of any manipulation by the physician. The coupling of distal engagement member 114 with retainer 142 also permits the physician to manipulate the radial orientation of implant 102 by rotating distal control member 140 and inner shaft 130 together. Active or passive shaping of distal control member 140 may allow for a more desirable placement of implant 102. For example, member 140 may have a curvature that places the implant in a more anterior anatomical position. This curvature may be inherently set in member 150 or actively applied by the physician though a separate entity such as a control wire. Once in the desired location and orientation, the physician can proximally retract inner shaft 130 with respect to distal control member 140 to initiate deployment of implant 102.

Distal engagement member 114 is held in place with respect to distal control member 140 by retainer 142, and proximal retraction of inner shaft 130 with respect to distal control member 140 causes ring-shaped structures 111 to begin to deploy in sequence (111*a*, then 111*b*, then 111*c*, then 111*d* (not shown)). Distal control member 140 can remain stationary or be moved longitudinally with respect to the urethra during deployment. In some embodiments, distal control member 140 is steerable to allow for angulation of implant 102 to accommodate relatively tortuous anatomy. The steerability of distal control member 140 can also accomplish relatively anterior placement of the implant relative to the bladder neck, which potentially contributes to improved flow results. For example, see distal control member 140 as shown in FIGS. 2C-2G and FIGS. 10C and 10D. Mechanisms for accomplishing steerability are discussed elsewhere herein and can likewise be applied to distal control member 140. In these or other embodiments, distal control member 140 can be significantly flexible to passively accommodate tortuous anatomy. In some embodiments, distal control member 140 has a predefined curve to assist in navigation.

To assist in deployment, inner shaft 130 can rotate clockwise and counterclockwise (as depicted by arrow 134) about distal control member 140. Referring back to FIGS. 1B-1C, implant 102 has a non-constant direction of winding that, when viewed as commencing at distal engagement member 114, proceeds clockwise along ring-shaped structure 111*a*, then reverses along interconnect 112*a* to a counterclockwise direction for ring-shaped structure 111*b*, then reverses along interconnect 112*b* to a clockwise direction for ring-shaped structure 111*c*, and then reverses along interconnect 112*c* to a counterclockwise direction for ring-shaped structure 111*d*, until ending at proximal engagement member 115. Depending on the direction of winding of the portion of implant 102 about to exit the open distal terminus of lumen 131, the transition of implant 102 towards the at-rest configuration can impart a torque on shaft 130 if shaft 130 is not actively rotated as implant 102 is deployed. That torque can cause shaft 130 to passively rotate (without user intervention) either clockwise or counterclockwise accordingly. In certain embodiments described elsewhere herein, shaft 130 is actively rotated during deployment. Rotation of inner shaft 130 with respect to distal control member 140 thus allows delivery device 103 to rotate and follow the direction of winding of implant 102. In some embodiments, all ring-shaped structures 111 are wound in the same direction, clockwise or counterclockwise (e.g., as in the case of a fully spiral or helical implant), or do not have a set direction of winding.

In this or other embodiments, the distal end region of inner shaft 130 is configured to be relatively more flexible than the more proximal portion of inner shaft 130, which can permit avoidance of excessive motion of the rest of device 103 during deployment, resulting in better visualization and less tissue contact by device 103. Such a configuration can also reduce the stress imparted on implant 102 by device 103 during delivery. For example, the portion of inner shaft 130 extending from outer shaft 120 during deployment can be relatively more flexible than the portion of inner shaft 130 that remains within outer shaft 120, thus allowing inner shaft 130 to flex more readily as implant 102 exits inner lumen 131. This in turn can stabilize delivery device 103 and allow the physician to obtain stable images of the appointment process.

Figure 4A:
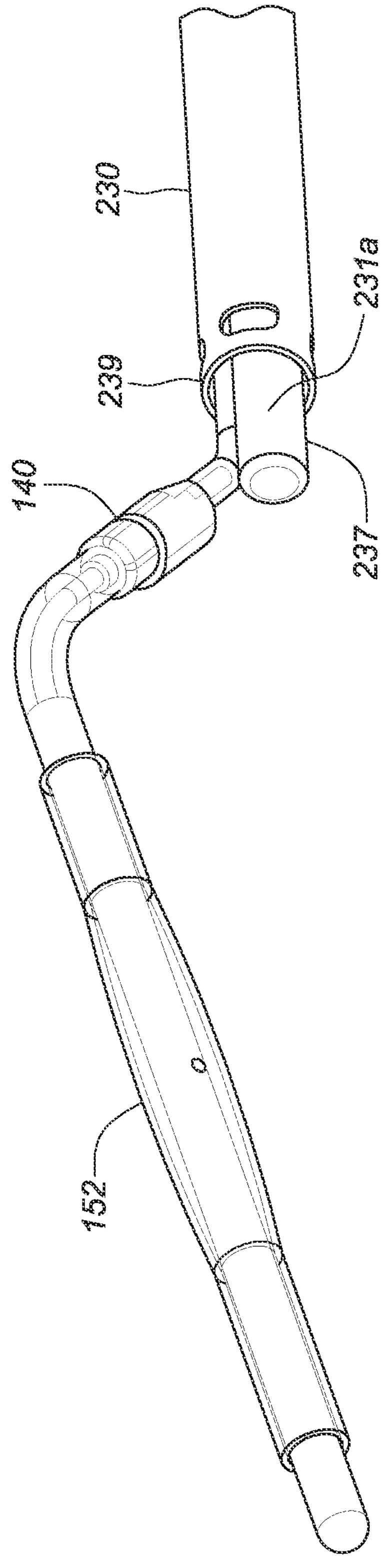
FIG. 4A-4C are perspective views depicting an example embodiment of an inner shaft.
Figure 4B:
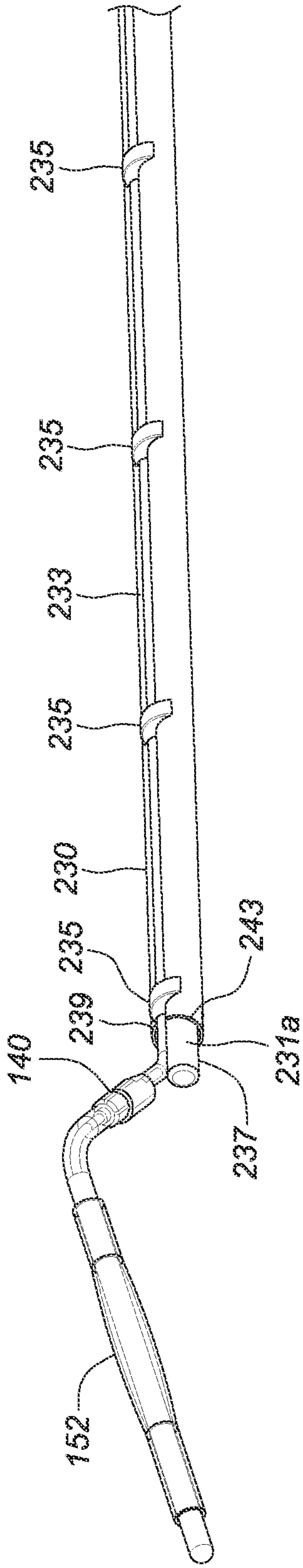
Figure 4C:
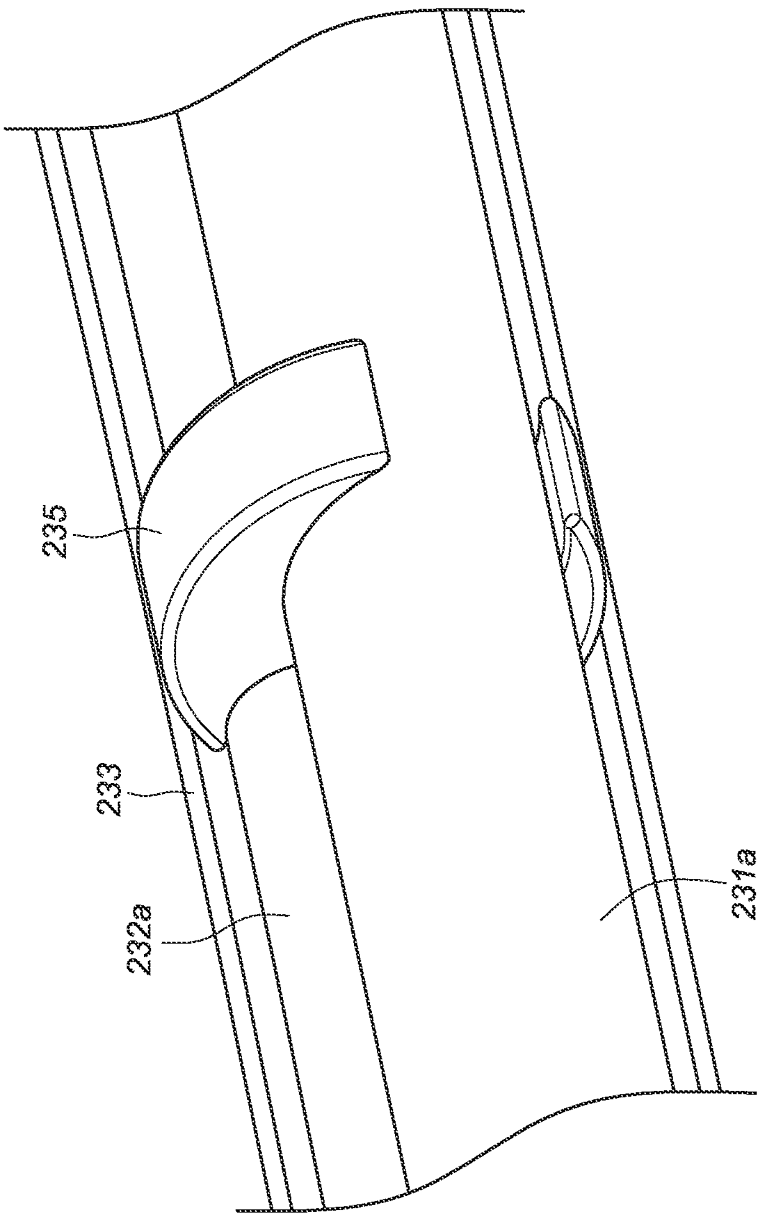
Figure 4D:
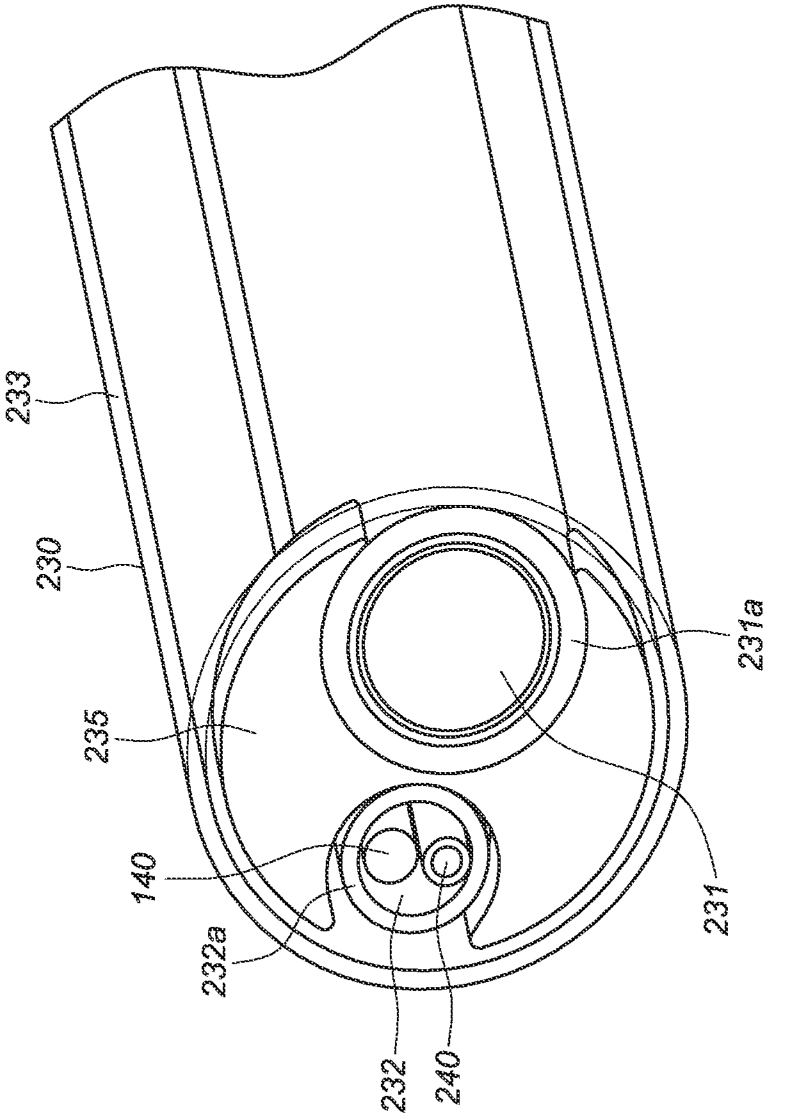
FIG. 4D-4E are cross-sectional views depicting an example embodiment of an inner shaft.
Figure 4E:
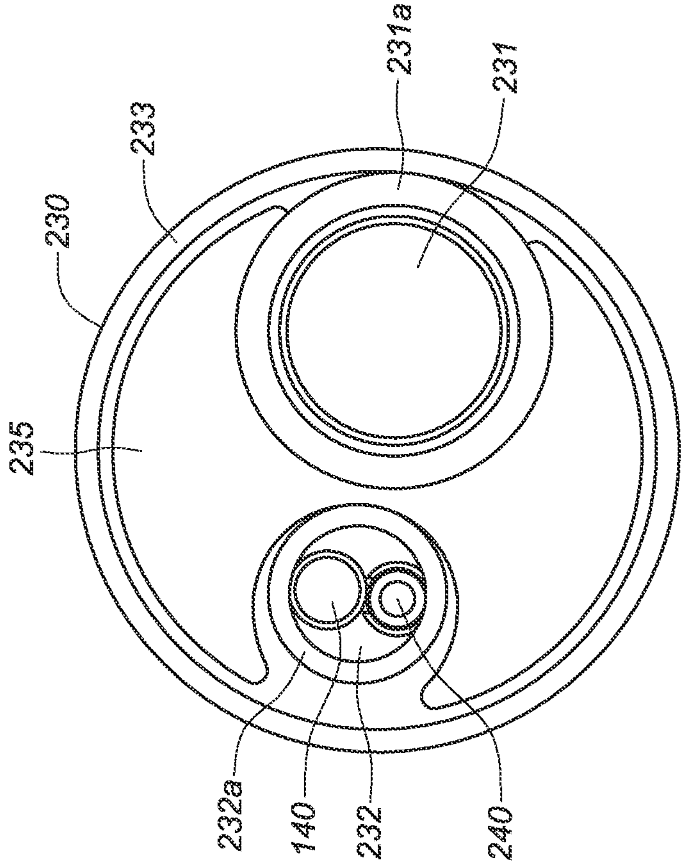

In an alternative embodiment, as seen in FIGS. 4A-4E, inner shaft 230 can include an outer torqueing tube 233 (FIGS. 4B-4E), one or more lumens for housing one or more implants 102 and/or other components, and one or more torqueing supports 235. In this embodiment, inner shaft 230 includes a first elongate tubular member 231*a* having a first lumen 231 in which one or more implants 102 can be housed. First elongate tubular member 231*a* also has a second elongate tubular member 232*a* (or tether) having a second lumen 232 in which a third elongate tubular member 140 and a fourth elongate tubular member 240, which could act as an inflation lumen, can be housed. In an alternative embodiment, the second elongate tubular member 232*a* (or tether) can be used for release/actuation and the inflation lumen can be concentric with the tether. As seen in FIGS. 4D and 4E, the first 231*a* and second 232*a* elongate tubular members can sit side-by-side and be held in place by the torqueing supports 235. The torqueing supports 235 can be small plates spaced within the outer torqueing tube 233 from a proximal to a distal end of outer torqueing tube 233. For example, the torqueing supports 235 may be placed about 3 to about 6 inches apart, alternatively about 2 to about 5 inches apart, alternatively about 1 to about 4 inches apart. The torqueing supports 235 can be bonded or otherwise fixed in place relative to the outer torqueing tube 233 to ensure that axial and angular position of the outer torqueing tube 233 can be maintained by the user. The first elongate tubular member 231*a* can be fixed to the torqueing supports 235 to ensure that the first elongate tubular member 231*a* moves with the outer torqueing tube 233. The second elongate tubular member 232*a* may not be fixed to the torqueing supports 235 so that the second elongate tubular member 232*a* can move axially and rotationally relative to the support plate and outer torqueing tube 233.

As seen in FIG. 4B, the flexible tip 243 may be created by fixing the first elongate tubular member or implant delivery tube 231*a* such that its distal end 237 extends beyond the distal tip 239 of the outer torqueing tube 233 by between about 0 cm and 1.5 cm, alternatively between about 0 cm and 1.0 cm, and alternatively between about 0.2 and 1.0 cm.

The components of the inner shaft may be made from appropriate materials. The first elongate tubular member or implant delivery tube 231*a* may be a braided tubular assembly with a lubricious liner. It may be made from a laser cut hypotube with a lubricious liner, a single polymer extrusion, or other appropriate material. The outer torqueing tube 233 may be made from a laser cut hypotube, a braided construction, a polymer extrusion, or other appropriate material. The torqueing supports 235 may be laser-cut metal plates, molded plastic components, extruded materials, or other appropriate material.

FIG. 2B depicts implant 102 after three ring-shaped structures 111*a*, 111*b*, and 111*c* have been deployed. Proximal retraction of shaft 130 continues until the entirety of implant 102, or at least all of ring-shaped structures 111, have exited lumen 131. If the physician is satisfied with the deployed position of implant 102 and the deployed shape of implant 102, then implant 102 can be released from delivery device 103. A control wire 146 (not shown in FIG. 2B) extends within the length of control member 140, either in the same lumen as anchor delivery member 150 or in a different lumen, and is coupled to retainer 142. Control wire 146 can be routed into member 140 through an opening 148.

Release of the distal end of implant 102 can be accomplished by releasing retainer 142. Retainer 142 can be a cylindrical structure or other sleeve that linearly or rotationally actuates over a cavity or recess in which a portion of implant 102 is housed. In the embodiment of FIG. 2B, retainer 142 includes an opening or slot that allows distal engagement member 114 to pass therethrough. Retainer 142 can rotate with respect to the cavity or recess in which distal engagement member 114 (not shown) is housed until the opening or slot is positioned over member 114, at which point member 114 is free to release from distal control member 130. Rotation of retainer 142 can be accomplished by rotation of a rotatable shaft, rod or other member coupled with retainer 142 (and accessible at proximal control device 200). Alternative embodiments of retainers can be found in FIGS. 2C-2F of International Application No. PCT/US19/32637, filed May 16, 2019, which was previously incorporated by reference in its entirety for all purposes.

Figure 2C:
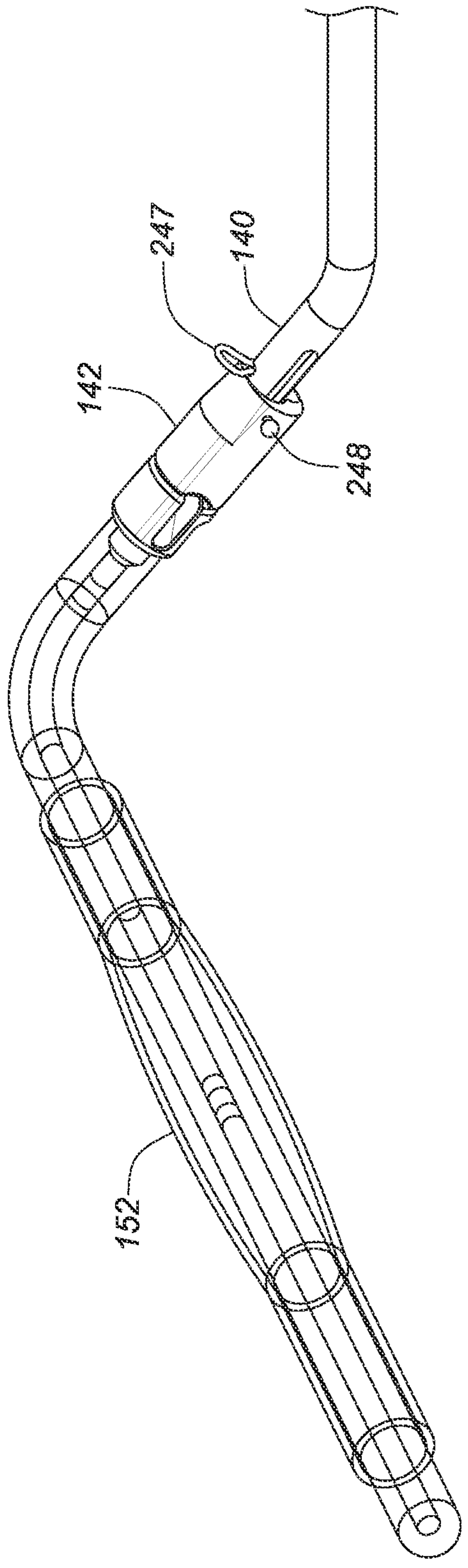
FIGS. 2C-2G are perspective views depicting an example of a release mechanism.
Figure 2D:
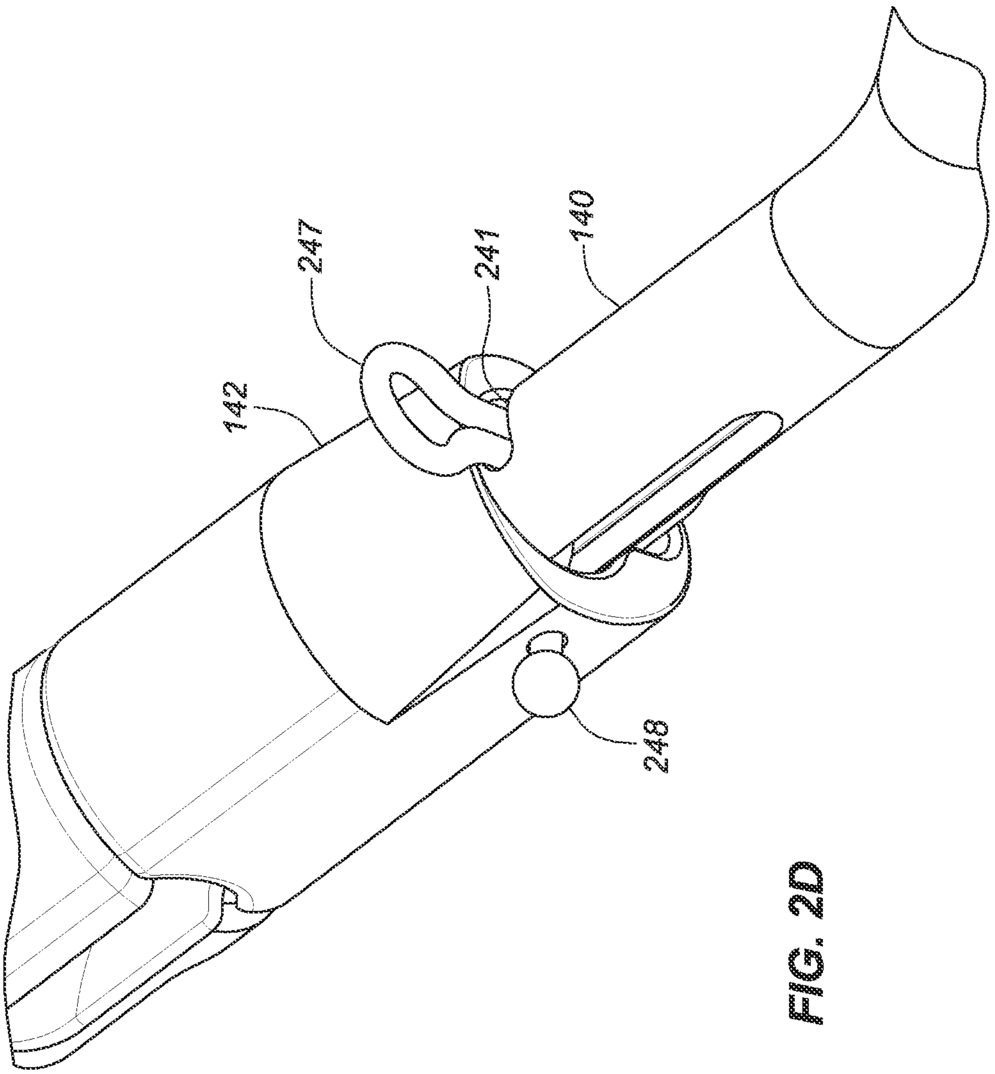
Figure 2E:
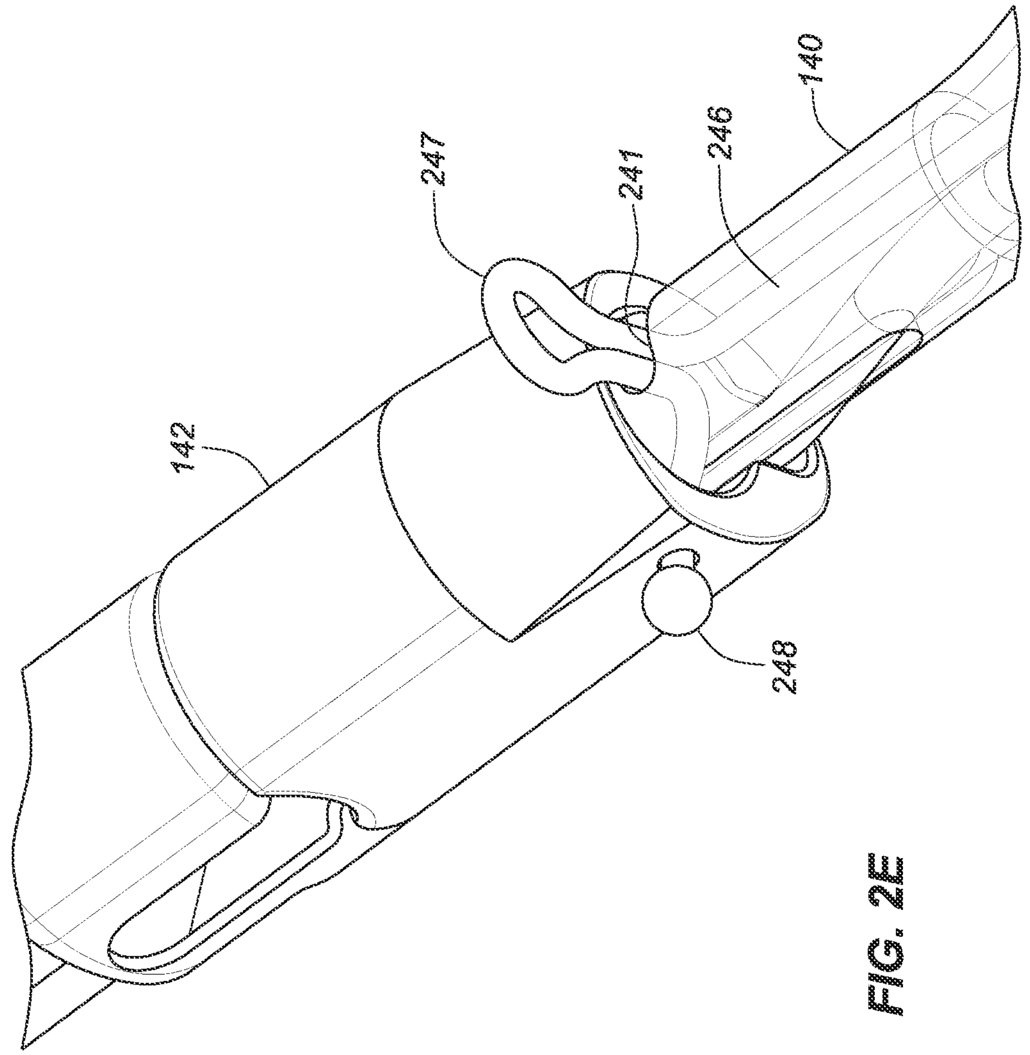

FIGS. 2C-2G are perspective views depicting another example embodiment of system 100 with an alternative retainer 142 that can be fixed in position with a tether lock. As in other embodiments, retainer 142 slides distally and/or proximally with respect to distal control member 140. Distal engagement member 114 of implant 102 can be received within a corresponding recess 143 (FIG. 2G) of distal control member 140. Retainer 142 can slide over distal engagement member 114 while received within this recess 143 until retainer 142 abuts a portion of member 140, which has opening 241 located near its distal end. A control wire 246 extends within the length of control member 140, either in the same lumen as anchor delivery member 150 or in a different lumen, and attaches or couples to retainer 142 at its distal end 248. As seen in FIG. 2E, control wire 246 passes out of and back into opening 241 in distal control member 140, such that control member 246 forms a loop 247 that protrudes from the opening and extends along an axis perpendicular to a longitudinal axis of the distal control member and a longitudinal axis of retainer 142. Loop 247, which is located adjacent to and proximal of retainer 142, prevents retainer 142 from moving in a proximal direction over distal control member 140.

Figure 2F:
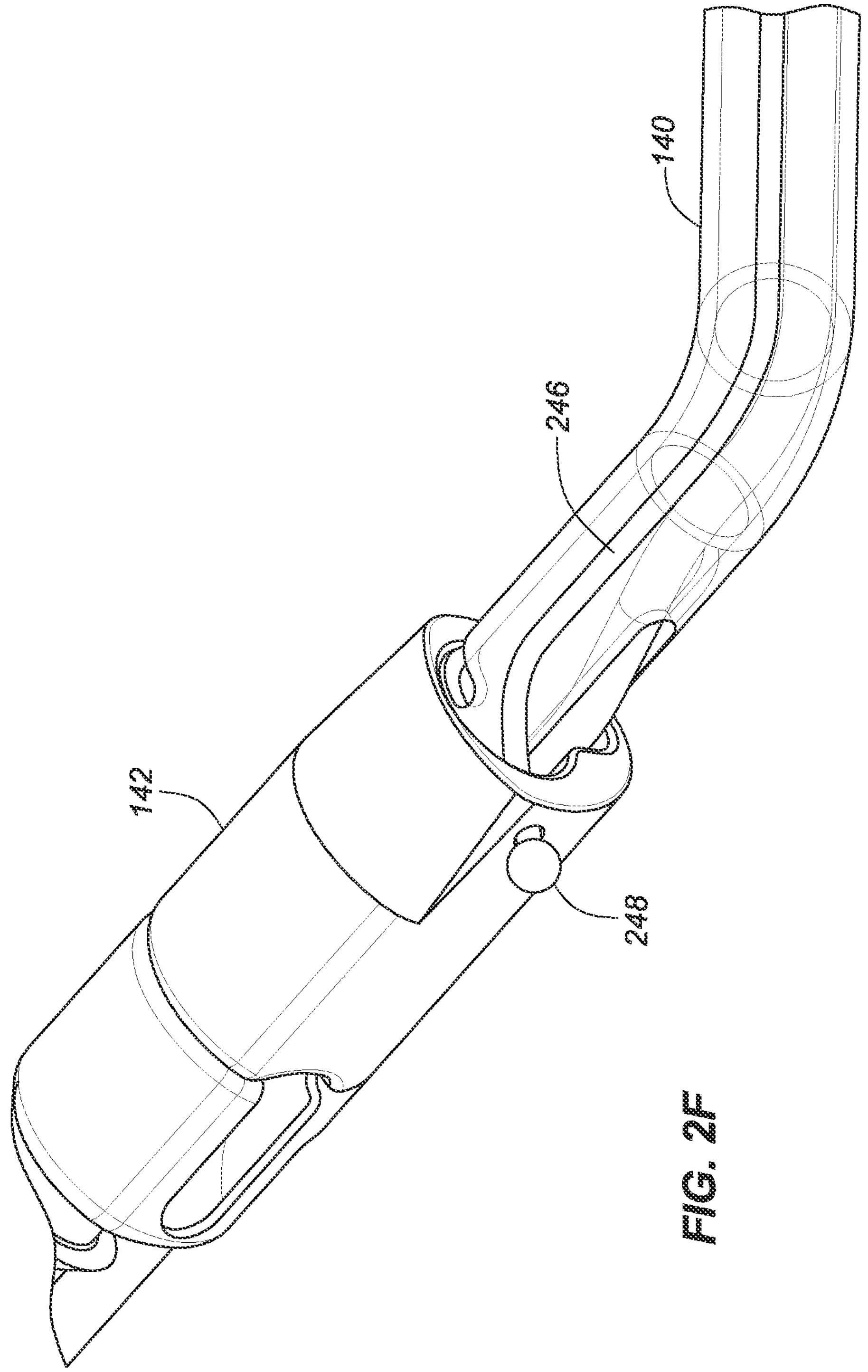
Figure 2G:
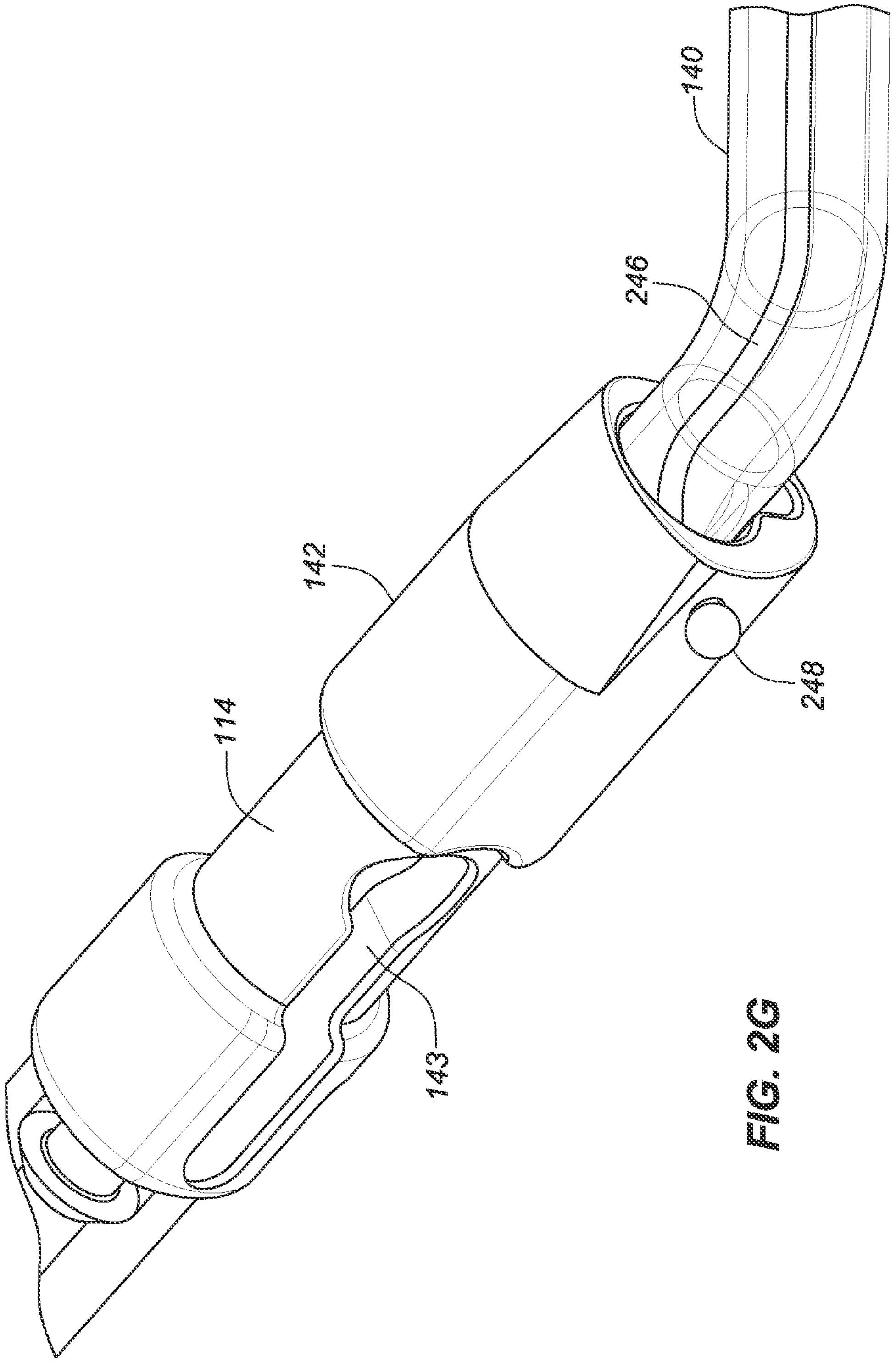

Upon satisfactory deployment of implant 102 within the urethra, e.g., in the state of FIG. 2C, control wire 246 can be tensioned by pulling control wire 246 in a proximal direction (away from the implant 102). As seen in FIG. 2F, the tension pulls loop 247 into the lumen of distal control member 140, thereby removing the obstruction preventing retainer 142 from sliding proximally. After the loop is withdrawn into the lumen of distal control member 140, as seen in FIG. 2G, retainer 140 is proximally retracted by further pulling control wire 246 proximally to expose engagement member 114 and permit its release from member 140.

Control member 146, 246 may be made from nitinol, Kevlar, stainless steel, suture, liquid crystal polymers (LCP) or any other tensionable material.

Figure 2H:
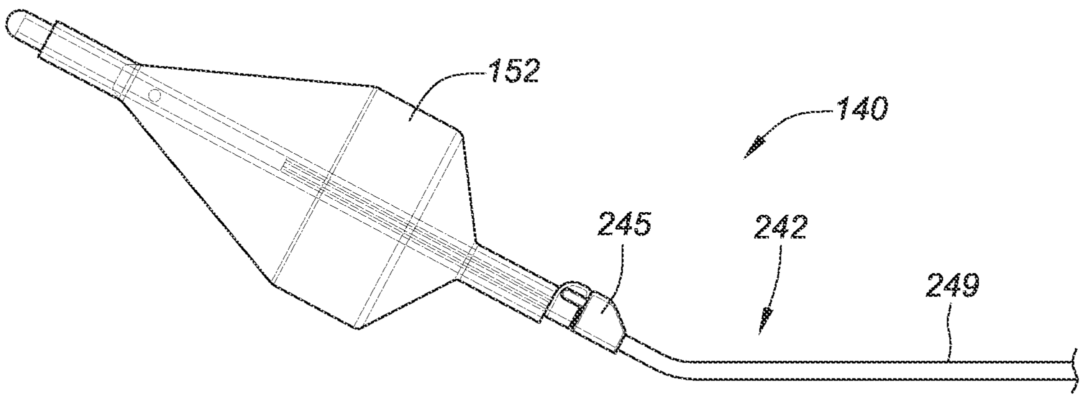
FIGS. 2H-2J are views depicting an alternative example of a release mechanism.
Figure 2I:
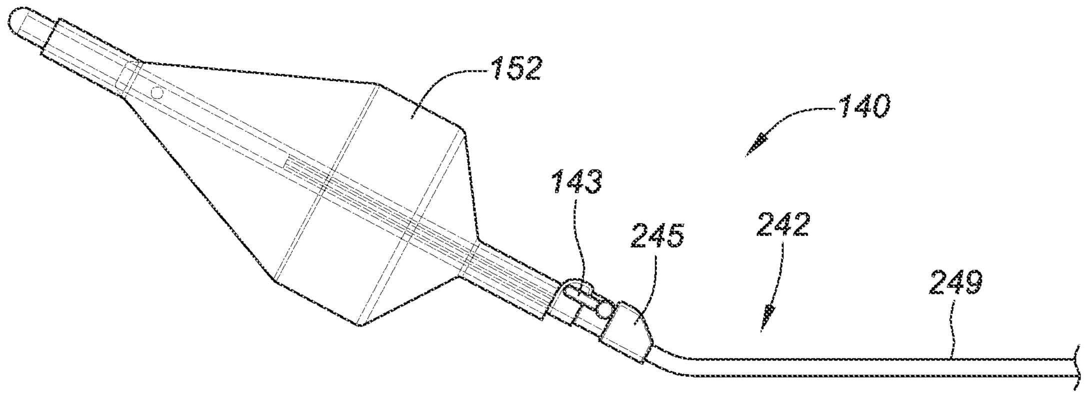
Figure 2J:
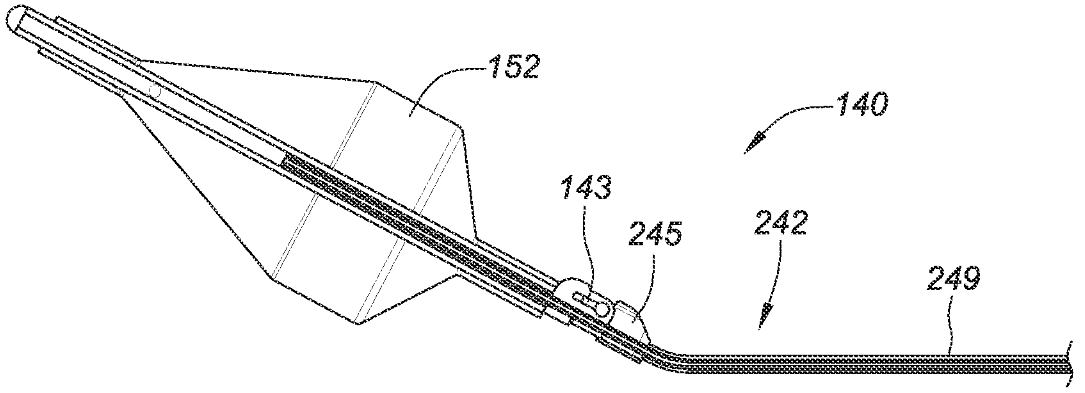

FIGS. 2H-2J illustrate another example embodiment of system 100 with an alternative retainer 242 that can be fixed in position. As with other embodiments described, retainer 242 can be a cylindrical structure or other sleeve that linearly or rotationally actuates over a cavity or recess in which a portion of implant 102 is housed. Retainer 242 includes cover 245 that is coupled to an outer tube 249 that extends to the control device 200. In the embodiment of FIGS. 2H-2J, retainer 242 includes an opening or slot (not shown) that allows distal engagement member 114 to pass therethrough. FIG. 2H shows cover 245 closed over the recess 143 that is adapted to hold distal engagement member 114. Retainer 242 can be withdrawn proximally with respect to the cavity or recess in which distal engagement member 114 is housed until the opening or slot is positioned over member 114, at which point member 114 is free to release from distal control member 130. As seen in FIG. 2I, cover 245 has been withdrawn by actuating outer tube 249 proximally. Withdrawal of cover 245 of retainer 242 can be accomplished by withdrawing outer tube 249 proximally, which is accessible at proximal control device 200. FIG. 2J is a cross-section showing the retainer 242 and the inflation lumen that communicates with anchor 152. The inflated diameter of the anchor balloon can be between about 1 cm and 7 cm, alternatively between about 2 cm and 6 cm, alternatively between about 1 cm and 6 cm.

Figure 3A:
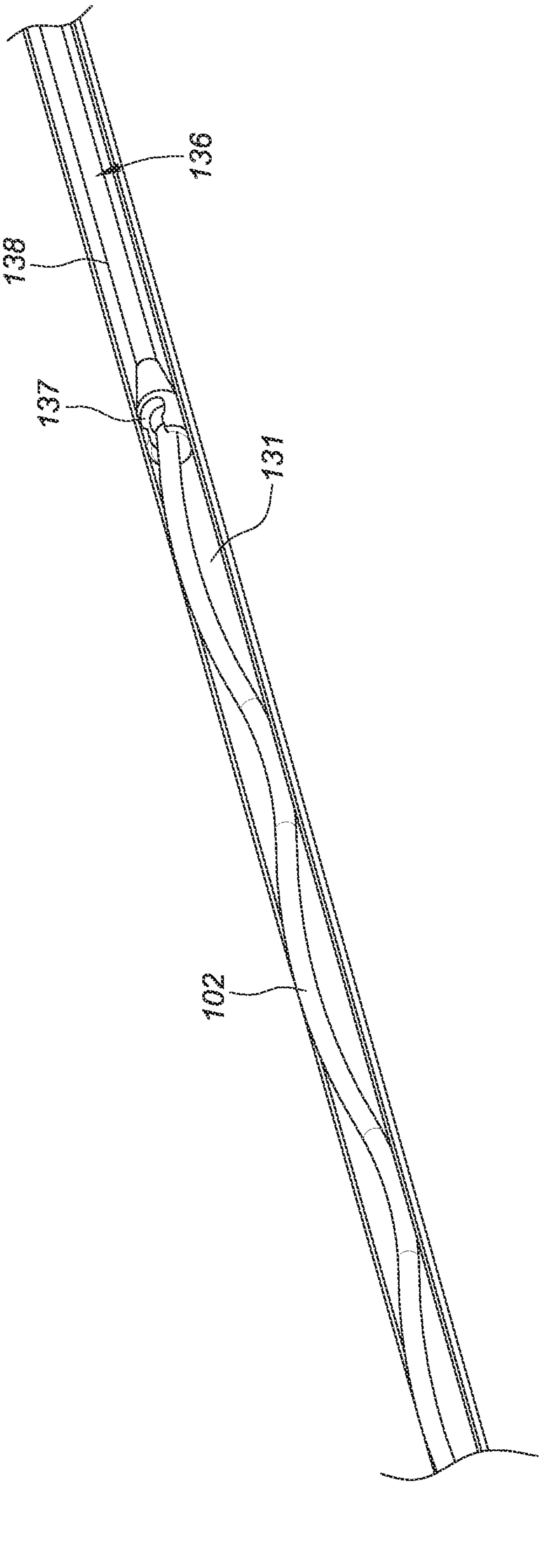
FIGS. 3A-3C are perspective views depicting example embodiments of a grasper component in use within a delivery system.

Release of the proximal end of implant 102 is also controllable. FIG. 3A is a partial cross-sectional view depicting an example embodiment of system 100 with a portion of implant 102 shown within inner lumen 131 of inner shaft 130. Here, implant 102 is in the lineated state prior to deployment with proximal engagement member 115 coupled with a grasper 136 that is slidable distally and/or proximally within lumen 131. Grasper 136 can include a distal end region 137 on or coupled with a shaft 138. Grasper 136 is preferably controllable to rotate and longitudinally translate (e.g., push and pull) implant 102 with respect to inner shaft 130.

Figure 3B:
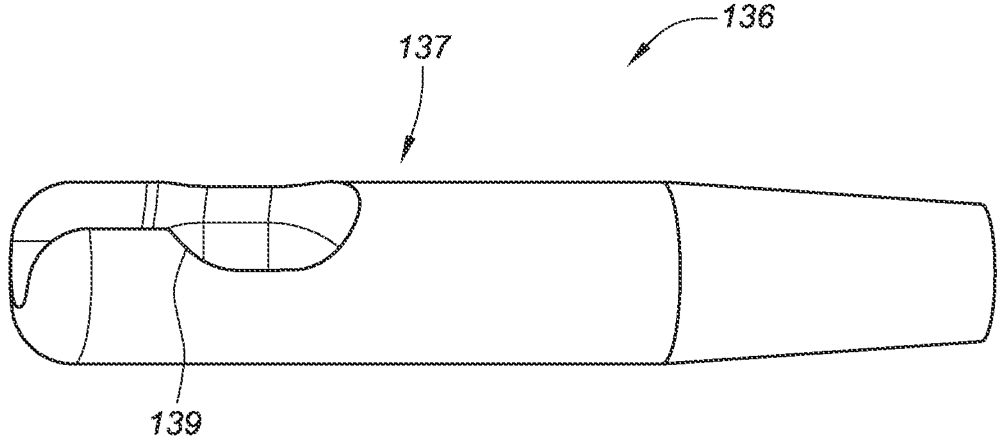
Figure 3C:
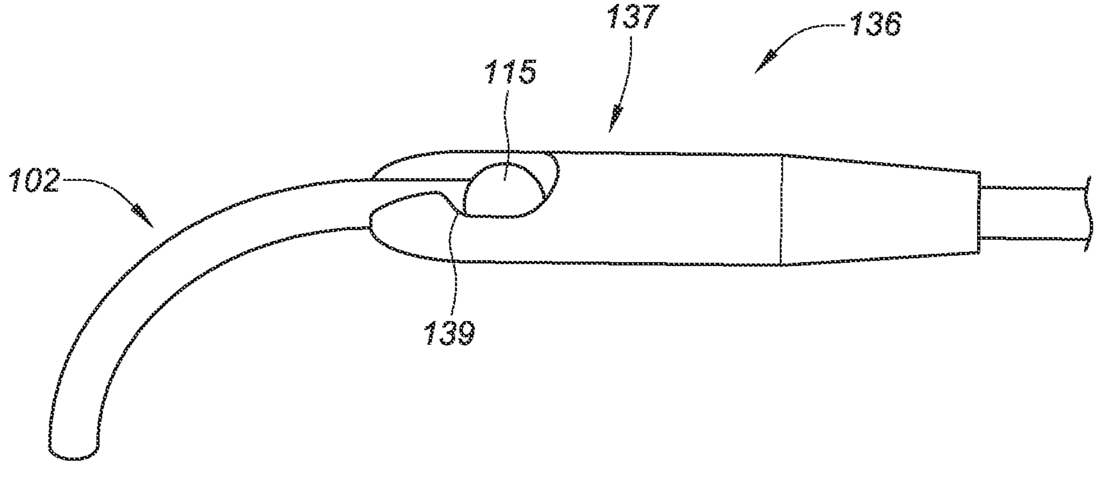

FIGS. 3B and 3C are perspective views depicting an example embodiment of distal end region 137 of grasper 136 without implant 102 and with implant 102, respectively. Grasper 136 includes a recess (also referred to as a cavity or pocket) 139 for receiving and holding proximal engagement member 115. Here, the enlarged portion 115 is retained within recess 139 by a distal necked down region having a relatively smaller width. While within inner lumen 131, the sidewalls of inner shaft 130 maintain proximal engagement member 115 within recess 139. When distal end region 137 exits inner lumen 131 (either by retracting inner shaft 130 with respect to grasper 136 or by advancing grasper 136 with respect to inner shaft 130), the restraint imparted by the inner shaft sidewalls is no longer present and engagement member 115 is free to release from grasper 136. Thus, when the physician is satisfied with placement of the deployed implant 102, distal engagement member 114 can be released by moving retainer 142 and permitting distal engagement member 114 to decouple from control member 140, and proximal engagement member 115 can be released by exposing grasper 136 from within inner shaft 130 and permitting proximal engagement member 115 to decouple from grasper 136.

Grasper 136 can also assist in loading implant 102. In some embodiments, application of a tensile force on implant 102 with grasper 136 (while the opposite end of implant 102 is secured, for example, by retainer 142) facilitates the transition of implant 102 from the at-rest configuration to a lineated configuration suitable for insertion of implant 102 into inner shaft 130.

Anchor delivery member 150 can have multiple different configurations and geometries (e.g., including those that extend in one direction across the bladder wall, two directions across the bladder wall (e.g., left and right), or three or more directions across the bladder wall). Additional examples of anchor delivery members and anchors are described in FIGS. 2B and 4A-4J of International Application No. PCT/US19/32637, filed May 16, 2019, which was previously incorporated by reference in its entirety for all purposes.

Upon completion of the implant deployment procedure, anchor 152 can be collapsed or retracted to permit removal of delivery device 103. For instance, in embodiments where anchor 152 is a balloon, that balloon is deflated and optionally retracted back into a lumen of device 103, and subsequently withdrawn from the bladder and urethra. In embodiments where anchor 152 is a wire form or other expandable member (such as those described with respect to FIGS. 4A-4G of International Application No. PCT/US19/32637, filed May 16, 2019, which was previously incorporated by reference in its entirety for all purposes), anchor 152 is retracted back into the lumen of device 103 from which it was deployed, and device 103 can subsequently be withdrawn from the bladder and urethra. Retraction can be accomplished using fluid or pneumatic actuation, a screw type mechanism, or others.

Example Embodiments of Proximal Control Devices and Related Methods

Figure 5A:
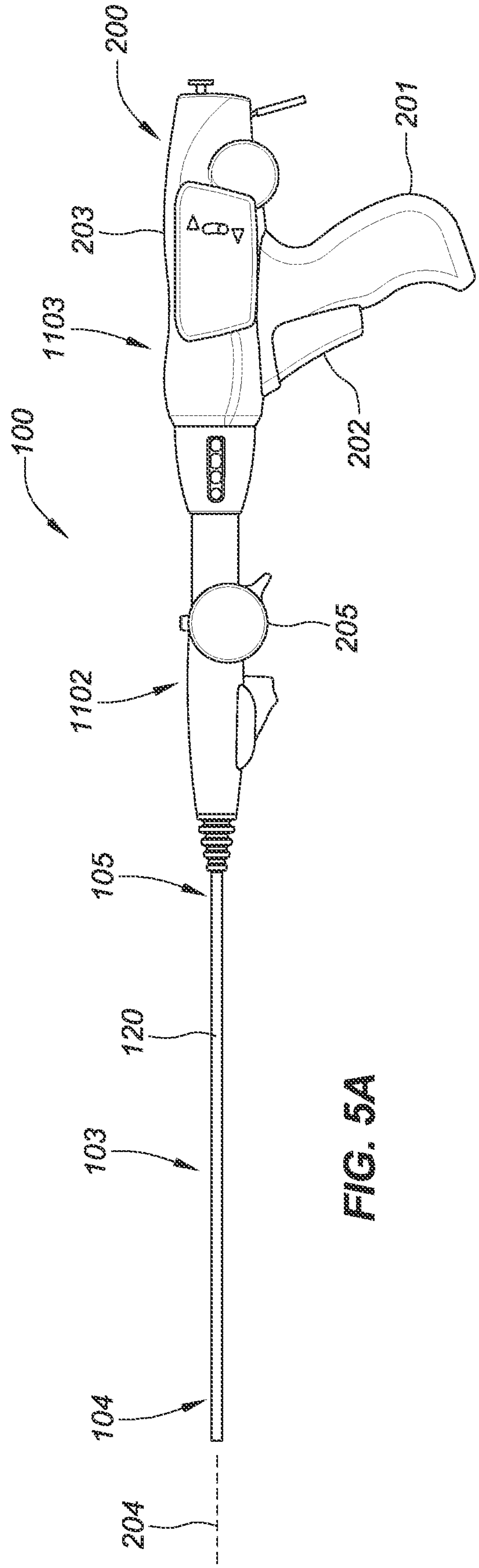
FIGS. 5A-5B are side views depicting an example embodiment of a delivery system in various stages of deployment of an implant.
Figure 5B:
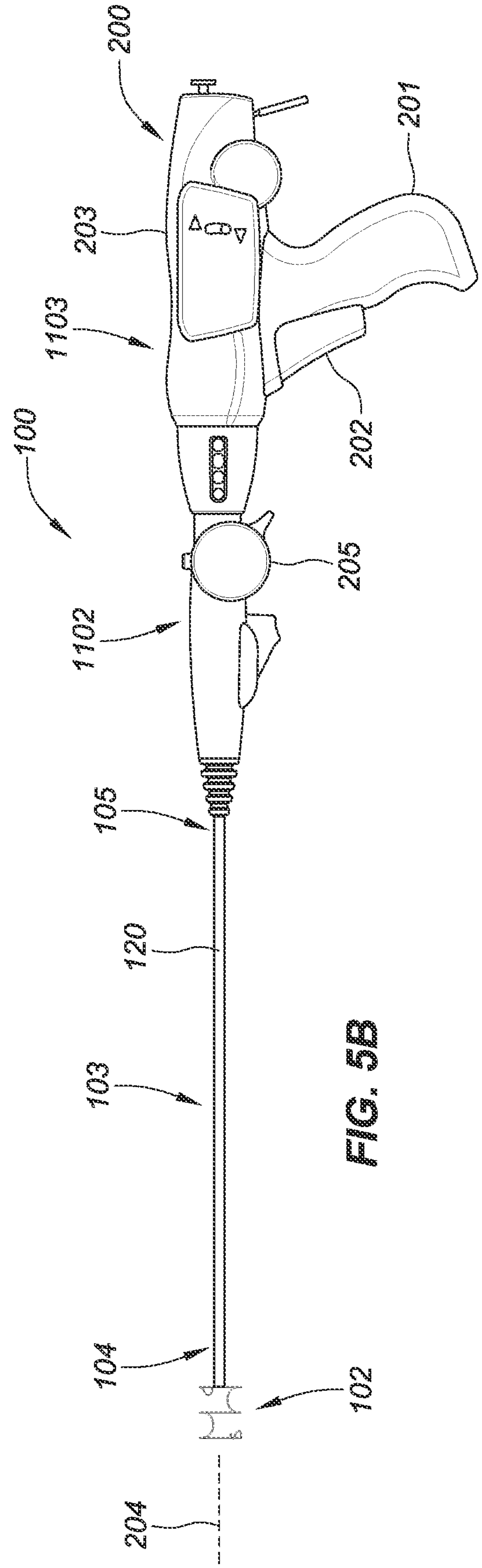
Figure 5C:
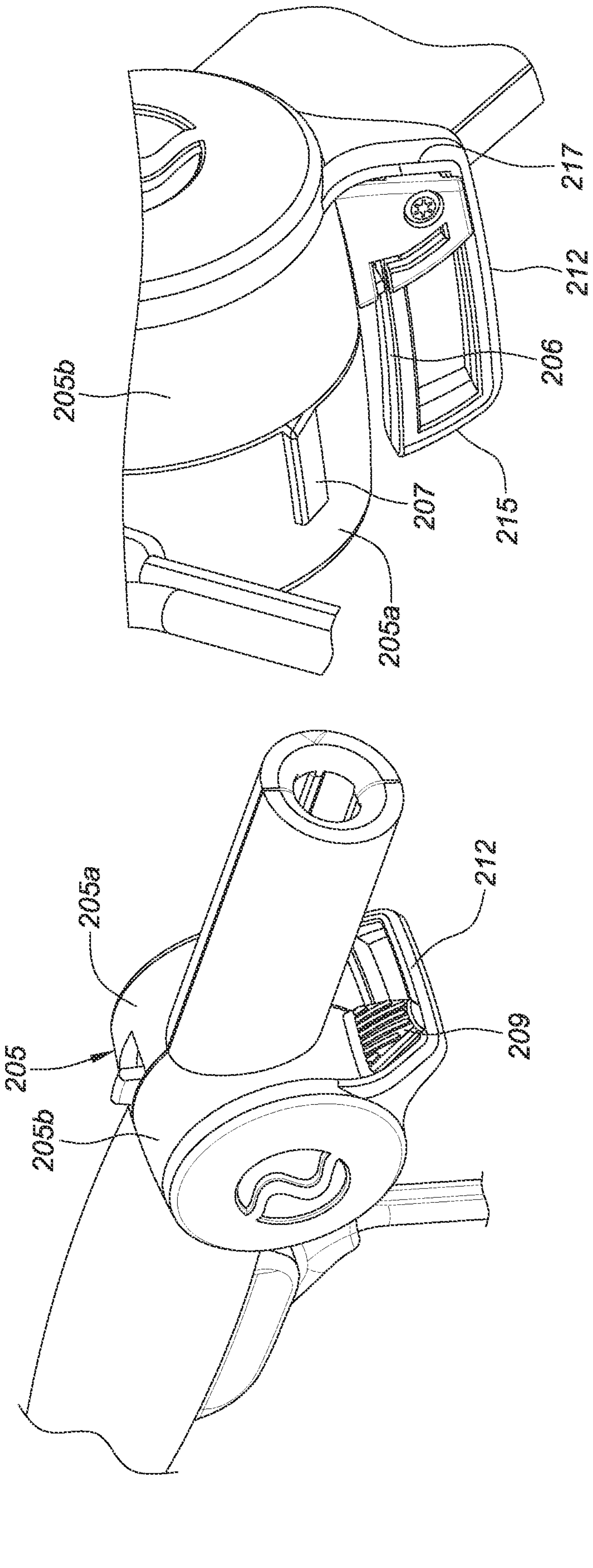
FIGS. 5C-5F are perspective views depicting an example embodiment of a steering lock device.
Figure 5D:
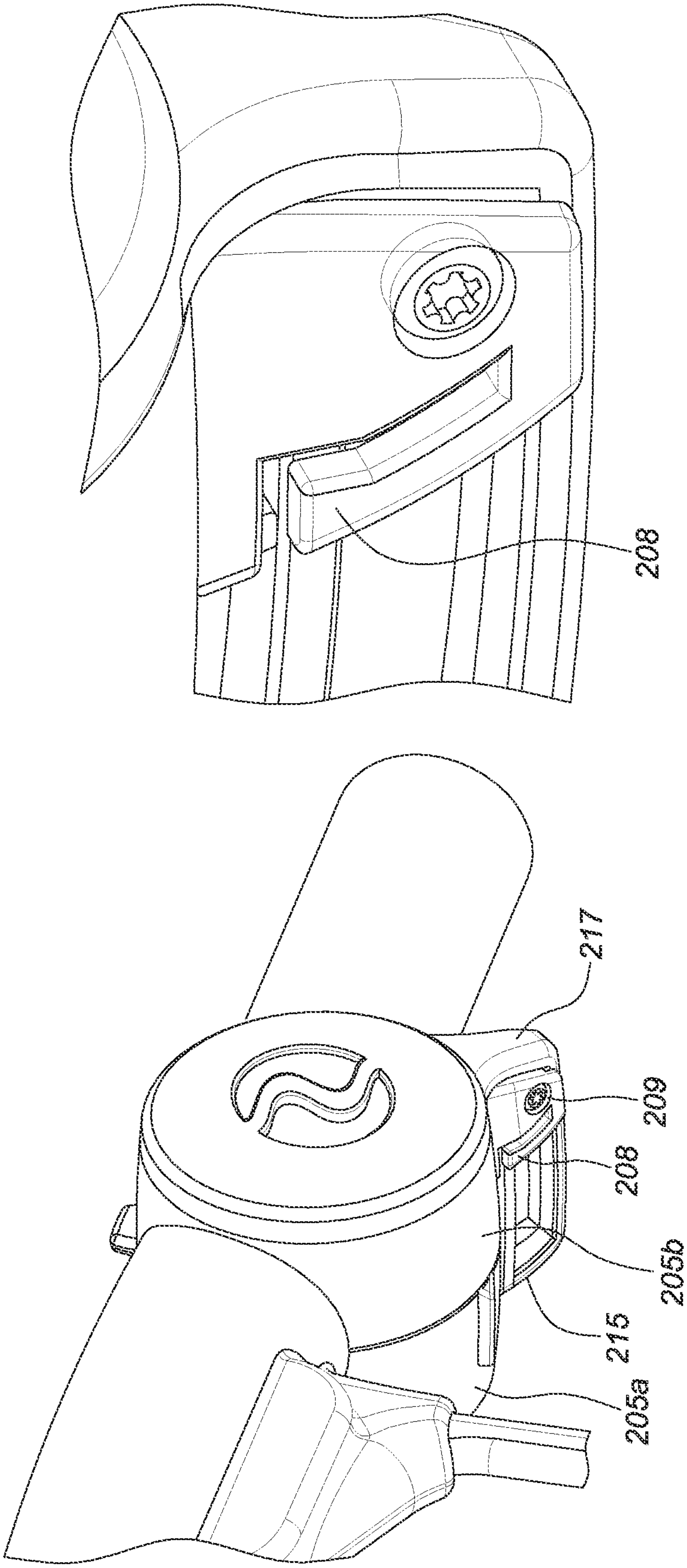

FIG. 5A is a side view depicting an example embodiment of delivery system 100 prior to deployment of implant 102, and FIG. 5B is a side view depicting this embodiment with implant 102 in a deployed configuration (anchor delivery member 150 and distal control member 140 are not shown). In this embodiment proximal control device 200 is a handheld device having a handle 201, a first user actuator 202 (configured in this example as a trigger), a main body 203, and a second user actuator 205. A longitudinal axis of delivery device 103 is indicated by dashed line 204. Proximal control device 200 can include mechanisms that are manually powered by actuation of actuator 202 to cause relative motions of the components of device 103. In other embodiments, proximal control device 200 can utilize electrically powered mechanisms instead. Second user actuator 205 can be configured to control steering of delivery device 103. Here, as seen in FIGS. 5G and 5H, actuator 205 is configured as a rotatable wheel 225 that can wind or unwind a pull wire 221 within delivery device 103 and cause deflection of device 103 upwards and downwards as depicted here. Second user actuator 205 includes an extension 212 having paddle 206 extending from a first end 215 of the extension 212. As seen in FIG. 5A, prior to deployment, the extension 212 is closer to handle 201, e.g., extension 212 is angled toward handle 201. As seen in FIG. 5B, after implant 102 has been at least partially deployed from distal end region 104, extension 212 is angled away from handle 201 and angled or pointed towards distal end region 104. The dotted lines in FIG. 5B also indicate that the distal end of the inner tubular member 120 can be deflected to enable placement of the implant further anteriorly. Proximal control device 200 can be configured so that, after all of ring-shaped structures 111 have been deployed from inner lumen 131 but prior to advancement of proximal engagement feature 115 and recess 139 from within lumen 131, further deployment of implant 102 is automatically prevented. This provides the physician with an opportunity to verify that implant 102 has been properly deployed and placed prior to releasing implant 102 from delivery device 103. A detailed description of the control device 200 and the parts and gear assemblies contained therein, can be found in, e.g., FIGS. 6A-9F, of International Application No. PCT/US19/32637, filed May 16, 2019, which was previously incorporated by reference in its entirety for all purposes.

The device may also include a steering lock that enables the user to lock the steering anteriorly to place the implant in a more anterior position. As discussed previously, the steerability of the device can include a pull wire 225 that extends from distal end region 104 of delivery device 103 (e.g., where the distal ends of the pull wires are secured to a plate or other structure within distal end region 104) to proximal control device 200, where they can be manipulated by the user to steer delivery device 103. The steering structures can be located in one or more lumens of outer shaft 120, or can be coupled to or embedded within a sidewall of outer shaft 120. Delivery device 103 can be biased to deflect in a particular lateral direction (e.g., bend) such that device 103 automatically deflects in that manner and forces imparted to steer delivery device 103 are in opposition to this biased deflection.

The steering lock is part of extension 212 attached to actuator 205. As seen in FIGS. 5C-5H, actuator 205 includes a rotatable wheel 225, an extension 212, a latch 209, and a ledge 207. The housing of actuator 205 may include two halves, a right handle half **205*a* and a left handle half 205*b*. The rotatable wheel 225 is adapted to wind and unwind the pull wire and is located in and coupled to the housing. Extension 212 includes latch 209 and paddle 206, which extends from a first end 215 and terminates in detent 208, such that a gap exists between detent 208 and a second end 217 of extension 212. The second end 217 of extension 212 is attached to left handle half 205*b* and the first end is adjacent a portion of the right handle half 205*a*. The second end 217 of extension 212 includes the detent 208 and gap. The steering lock also includes ledge 207 that extends from right handle half 205*a* of the housing in proximity to the first end 215 of extension 212. Latch 209 is adapted to actuate or slide along the paddle 206. When latch 209 is located on the second end 217, detent 208 frictionally engages latch 209, thereby restraining latch 209 to the second end 217**.

Figure 5E:
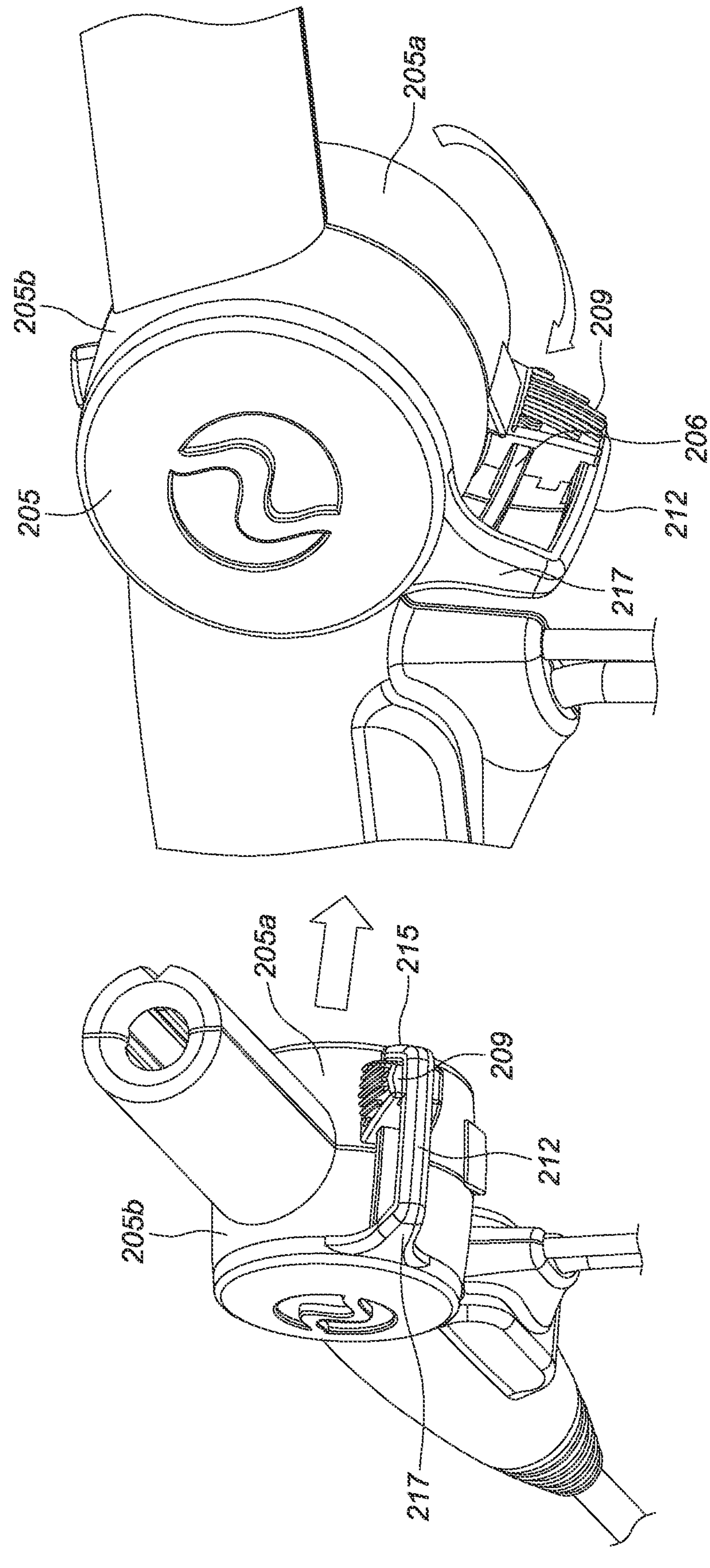
Figure 5F:
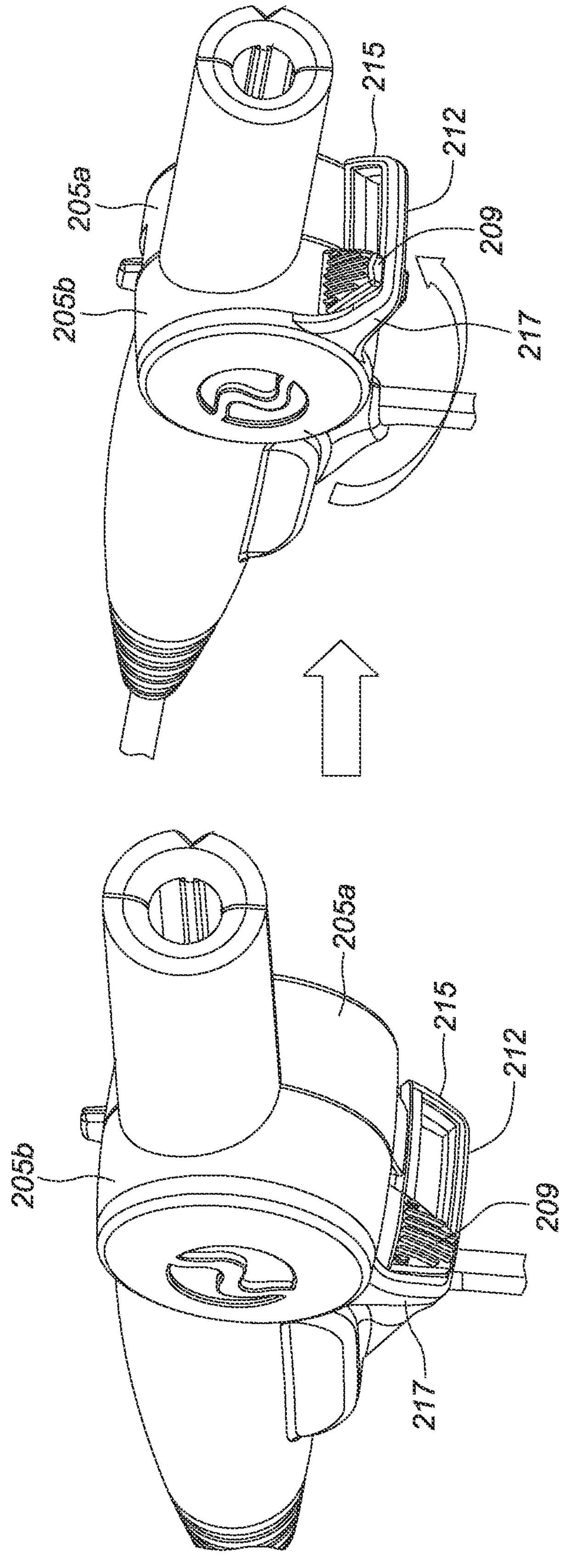
Figure 5G:
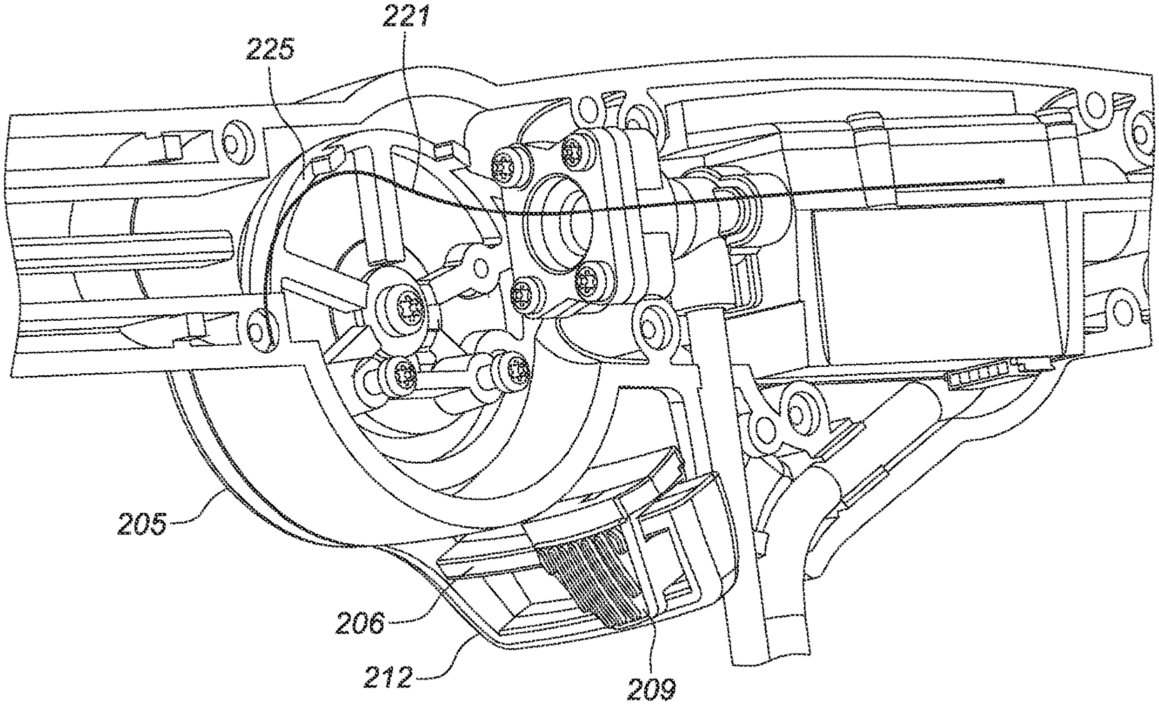
FIGS. 5G-5H are cross-sections depicting an example embodiment of a steering lock device.
Figure 5H:
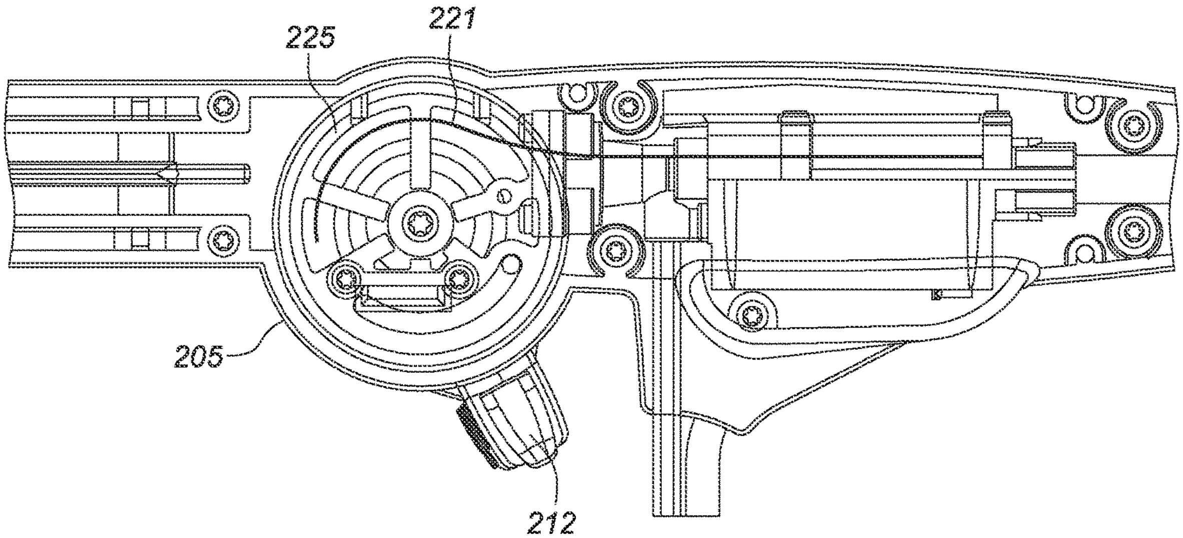

In use, as seen in FIG. 5E, the user can disengage latch 209 from detent 208 and move latch 209 along paddle 206 from the second end 217 to the first end 215 of extension 212. Once latch 209 is at the first end 215, extension 212 can be pushed in a direction towards distal end region 104 by the user until latch 209 comes into contact with ledge 207. Ledge 207 then frictionally engages latch 209 and holds extension 212 in a position angled toward distal end region 104 in a "locked" position. In the locked position, the rotatable wheel 225 cannot wind or unwind the pull wire 221 and the user cannot move (deflect or straighten) the distal end region 104 of the outer tubular member 103. As seen in FIG. 5F, to release paddle 206 from the "locked" position, the user can release latch 209 from ledge 207 and slide latch 209 along paddle 206 from the first end 215 to the second end 217 of extension 212. When latch 209 is no longer frictionally engaged by ledge 207, extension 212 can passively return to a rest position in which extension 212 is angled toward handle 201 (i.e., away from distal end region 104) due to spring-loading. In the unlocked position, the rotatable wheel 225 is capable of winding and unwinding the pull wire 221, thereby moving (deflecting or straightening) the distal end region 104 of the outer tubular member 103.

Example Embodiments of Delivery Methods

Figure 6A:
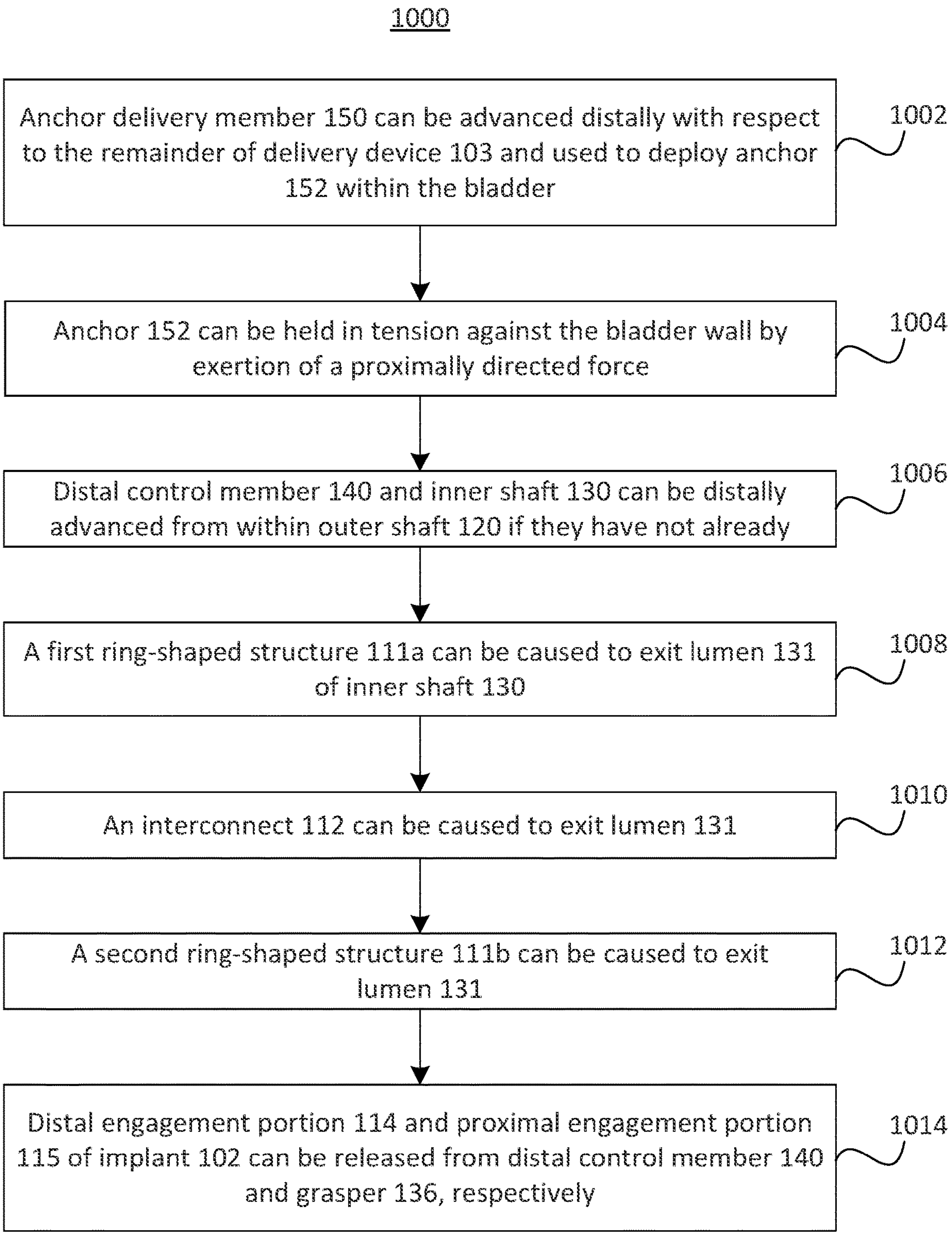
FIG. 6A is a flowchart depicting an example embodiment of a method for delivering an implant.

FIG. 6A is a flow diagram depicting an example embodiment of a method 1000 of delivering implant 102 using system 100. Distal end region of outer shaft 120 is inserted into the urethra, preferably with inner shaft 130, distal control member 140, and anchor delivery member 150 in retracted states fully contained within outer shaft 120 such that no part is extending from the open distal terminus of outer shaft 120. After advancement into the urethra, at step 1002 anchor delivery member 150 is advanced distally with respect to the remainder of delivery device 103 (e.g., members 120, 130, and 140) and used to deploy anchor 152 within the bladder. In some embodiments, deployment of anchor 152 can be the inflation of one or more balloons (e.g., as depicting in FIG. 2B) by the introduction of an inflation medium through an injection (e.g., luer taper) port. The longitudinal positioning (e.g., advancement and retraction) of anchor delivery member 150 and/or any wire-form members can be accomplished manually by the user manipulating a proximal end of anchor delivery member 150 and/or any wire-form members either directly or with proximal control device 200.

At step 1004, anchor 152 can be held in tension against the bladder wall by exertion of a proximally directed force on device 200. Anchor 152 can therefore provide an ordinate for system 100 from which to deploy implant 102 in an accurate location. This feature can ensure the implant is not placed too close to the bladder neck.

At 1006, distal control member 140 and inner shaft 130 can then be distally advanced from within outer shaft 120 if they have not already (for example, step 1006 can occur prior to steps 1002 and/or 1004). The user can manipulate the position of proximal control device 200 with the aid of imaging (as described herein) until implant 102 is in the desired position. Once implant 102 is in the desired position, the implant deployment procedure can begin. The steps for implant deployment can be performed automatically by user actuation of proximal control device 200 (e.g., actuation of trigger 202, selection of a position for switch 604, etc.), or the steps can be performed directly by hand manipulation of each component of delivery device 103, or by a combination of the two as desired for the particular implementation.

In some embodiments, deployment of implant 102 from within lumen 131 is fully accomplished by (1) distally advancing grasper 136 with respect to inner shaft 130, while inner shaft 130 is not moved, while in other embodiments, deployment of implant 102 from within inner lumen 131 is fully accomplished by (2) proximally retracting inner shaft 130 with respect to grasper 136 while grasper 136 is not moved. In some embodiments, deployment of implant 102 is fully accomplished by (3) a combination of both movements. In still other embodiments, deployment of implant 102 is fully accomplished by (1), (2), or (3) in combination with one or more rotations of inner shaft 130, in one or more directions (e.g., clockwise or counterclockwise) with respect to distal control member 140.

An example embodiment of a sequence of steps 1008, 1010, and 1012 for deploying implant 102 is described with reference to FIG. 6A and the timing diagram of FIG. 6B. First with reference to FIG. 6A, at step 1008 a first ring-shaped structure 111*a* is caused to exit lumen 131 of inner shaft 130, at step 1010 an interconnect 112 is caused to exit lumen 131, and at step 1012 a second ring-shaped structure 111*b* is caused to exit lumen 131. Steps 1010 and 1012 can be repeated for each additional interconnect 112 and ring-shaped structure 111 present on implant 102.

Figure 6B:
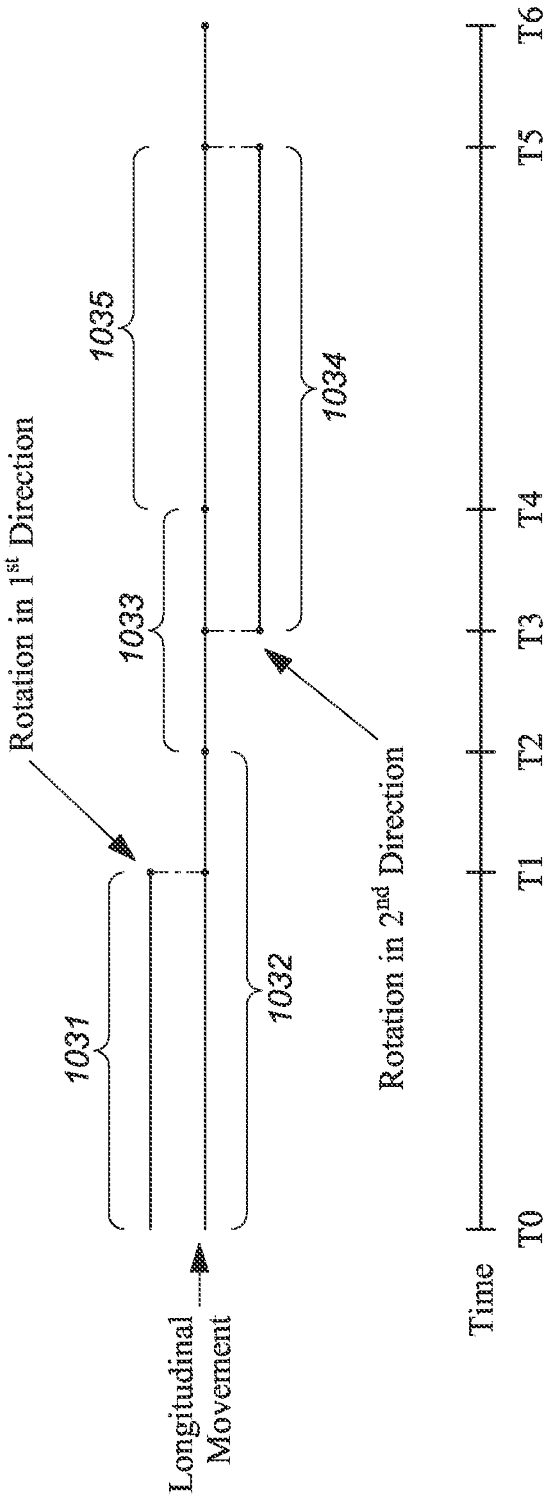
FIG. 6B is a timing diagram depicting an example embodiment of a sequence of steps for deploying an implant.

In FIG. 6B, step 1008 begins at the far left of the timing diagram at T0. Deployment of ring-shaped structure 111*a* corresponds to the duration of time marked 1008, deployment of interconnect 123 corresponds to time span 1010, and deployment of ring-shaped structure 111*b* corresponds to time span 1012. Those of ordinary skill in the art will recognize that the differentiations between deployment of a ring-shaped structure 111 and deployment of an interconnect 112 are approximations as the transitions between those portions of implant 102 can be gradual and do not have to have precise demarcations.

The embodiment described with respect to FIG. 6B is for an implant with ring-shaped structures 111 having opposite directions of winding (e.g., clockwise, then counterclockwise, then clockwise, etc.). Three different motions are indicated in FIG. 6B. At top is rotational motion of inner shaft 130 in one direction (e.g., clockwise), in the middle is longitudinal motion (e.g., proximal or distal) of one or more components of delivery device 103, and at bottom is rotational motion inner shaft 130 in the direction opposite (e.g., counterclockwise) that indicated at top. In embodiments where ring-shaped structures 111 of implant 102 are all wound in the same one direction, rotation of inner shaft 130 will also be in only one direction.

From time T0 to T1, deployment of implant 102 is accomplished by rotating inner shaft 130, as indicated in region 1031. At the same time, in region 1032, grasper 136, and thus implant 102, is distally advanced without moving outer shaft 120 longitudinally (neither distally nor proximally) nor rotationally, and also without longitudinally moving inner shaft 130 (neither distally nor proximally).

From time T1 to T2, rotation of inner shaft 130 is stopped but distal advancement of grasper 136 continues while shafts 120 and 130 do not move longitudinally.

From time T2 to T4, deployment of a first interconnect 112 takes place. In region 1033, from time T2 to T4, no distal advancement of grasper 136 (and implant 102) occurs. Deployment of interconnect 112 is accomplished by proximal retraction of both outer shaft 120 and inner shaft 130 while holding grasper 136 in place. This causes interconnect 112 to exit inner lumen 131 of shaft 130.

With respect to rotation of inner shaft 130, from time T2 to T3 no rotation of inner shaft 130 occurs. Within proximal control device 200 the interrupted portion of annular gear 802 continues and there is no rotation of shaft 130 by central gear 816.

In embodiments where interconnect 112 is straight, then it can be desirable to refrain from rotating shaft 130 while interconnect 112 is deployed from time T2 to T4. For embodiments where interconnect 112 is curved, such as the embodiment of FIGS. 1B-1D, it may be desirable to initiate rotation of inner shaft 130 during interconnect deployment. FIG. 6B depicts deployment for a curved interconnect 112, and from T3-T4 inner shaft 130 is rotated in the opposite direction as indicated by region 1034.

At T4, deployment of interconnect 112 is complete and deployment of second ring-shaped structure 111*b* begins. Proximal retraction of shafts 120 and 130 is stopped as indicated by the cessation of region 1033. Distal advancement of grasper shaft 138 is restarted in region 1035 at T4, while outer shaft 120 is not moved rotationally nor longitudinally. Rotation of inner shaft 130 continues as indicated in region 1034, but inner shaft 130 is not moved longitudinally These motions continue until time T5, at which point rotation of inner shaft 130 is stopped. Within proximal control device 200, an interrupted portion of annular gear 802 is reached and gear 802 disengages from the planetary gears and rotation of central gear 816 is stopped. User depression of trigger 202 continues from time T5-T6, the components operate with similar motions as described from time T1 to T2. If another interconnect 112 and ring-shaped structure 111 are present, then the sequence beginning at time T6 can be the same as that described beginning at time T2 and continuing to time T6.

In many embodiments described here, deployment of all of ring-shaped structures 111 can occur with a single continuous depression of trigger 202. In all of these embodiments, proximal control device 200 can instead be configured such that repeated pulls of trigger 202 are required to deploy all of ring-shaped structures 111 of implant 102.

During deployment, e.g., after time T0 up until completed deployment of the proximal-most ring-shaped structure 112, if the physician wishes to recapture implant 102, then depression of trigger 202 can be stopped. Trigger 202 can be spring-loaded or otherwise biased to return to the outermost position. See FIG. 6B.

If the physician is satisfied with deployment, then at 1014 distal engagement portion 114 and proximal engagement portion 115 of implant 102 can be released from distal control member 140 and grasper 136, respectively. By way of example, in proximal control device 200 the physician can pull tab 910 to permit trigger 202 to be depressed the rest of the way, which in turn can deploy proximal engagement portion 115 of implant 102, either by distal advancement of grasper 136, proximal retraction of shafts 120 and 130, or both. A tab can be coupled with control wire 146 and the pulling of the tab can pull wire 146 and remove retainer 142 from distal engagement portion 114.

Anchor 152 can then be recaptured (e.g., deflation of the balloon or retraction of the wire-form members) and withdrawn into anchor delivery member 150 if desired. Anchor delivery member 150, distal control member 140, and inner shaft 130 can be retracted into outer shaft 120 and then withdrawn from the urethra.

A more detailed description of the process by which the components in the control device accomplish the above steps is provided in International Application No. PCT/US19/32637, filed May 16, 2019, which was previously incorporated by reference in its entirety for all purposes.

Example Embodiments of User Assembly of Proximal Control Device

Referring back to FIG. 5A, proximal control device 200 can include a movable (e.g., retractable and/or advanceable) handle portion 1102 that can move with respect to the more proximally located handle portion 1103. FIG. 5A depicts movable handle portion 1102 in a distally advanced position prior to deployment of implant 102 and FIG. 5B depicts portion 1102 in a proximally retracted position after deployment of implant 102. Movable portion 1102 can be secured to and moved with outer shaft 120, and can also be moved independently of inner shaft 130, distal control member 140, and anchor delivery member 150 (not shown).

Figure 16A:
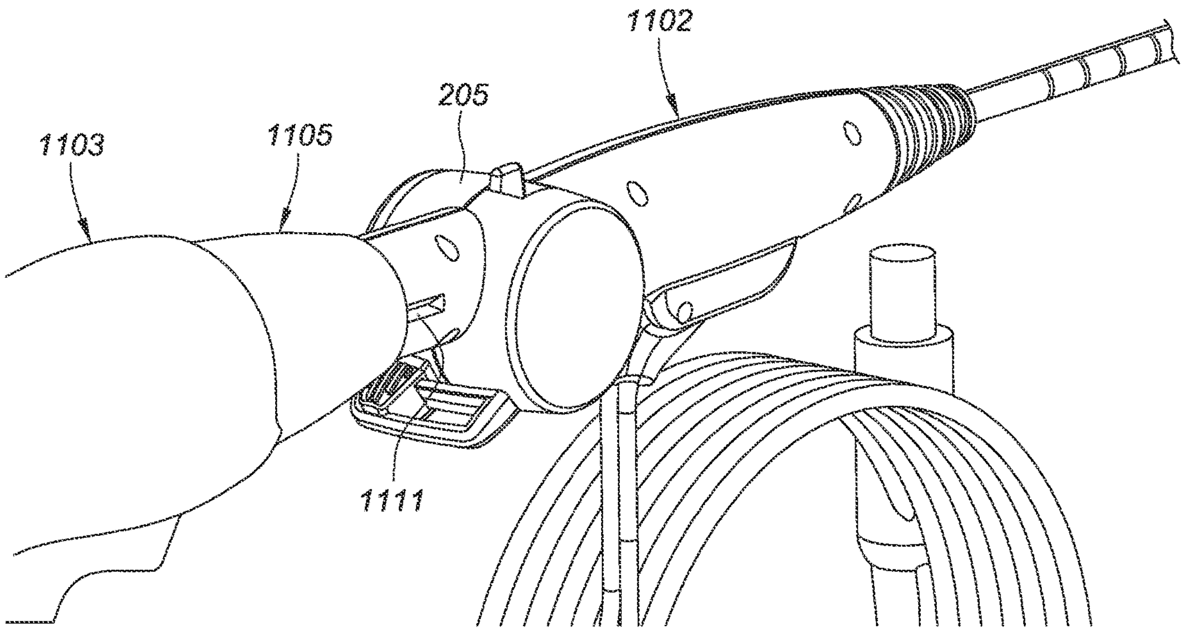
FIGS. 16A-16C are perspective views of an example embodiment of an anti-rotation mechanism.
Figure 16B:
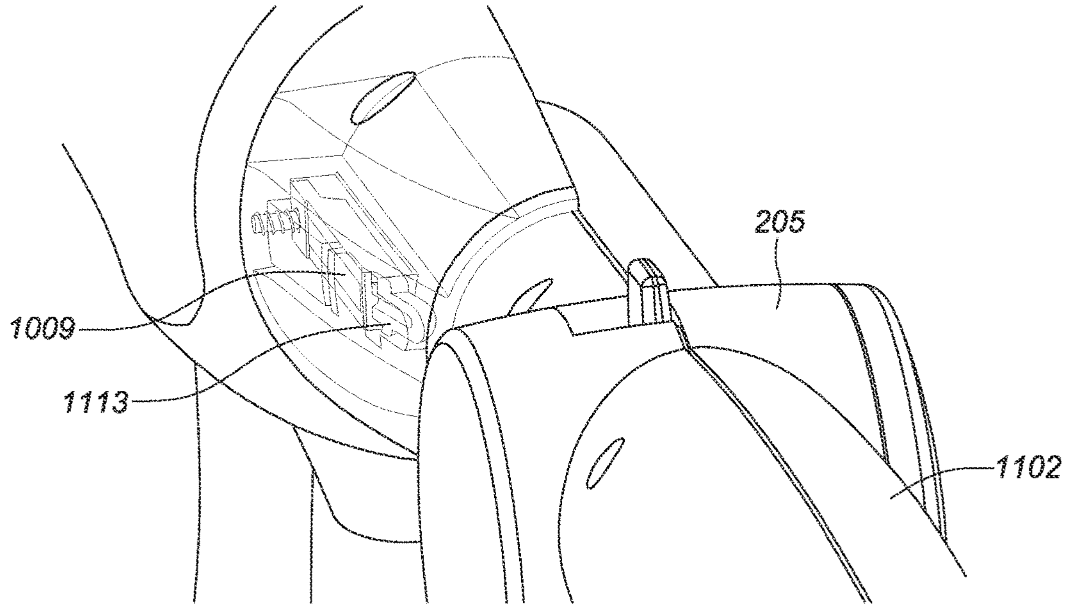
Figure 16C:
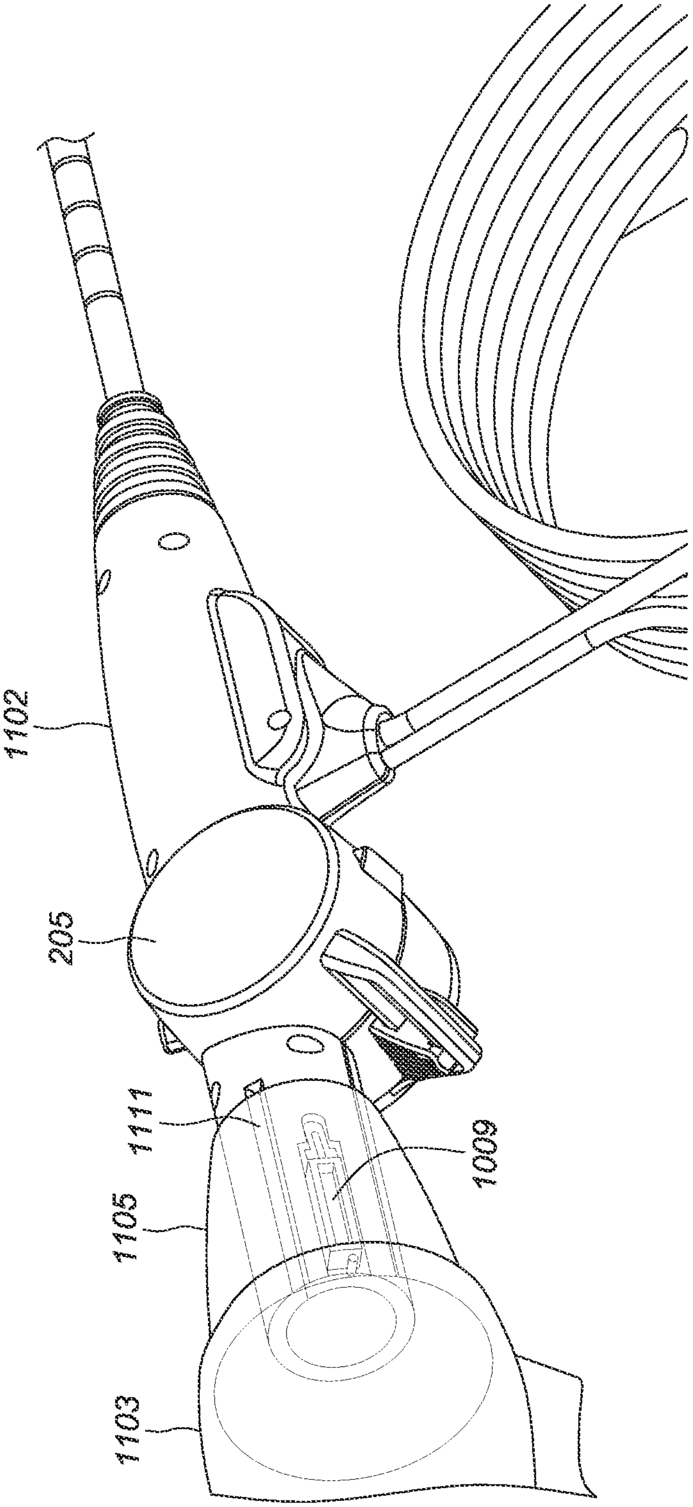
Figure 16D:
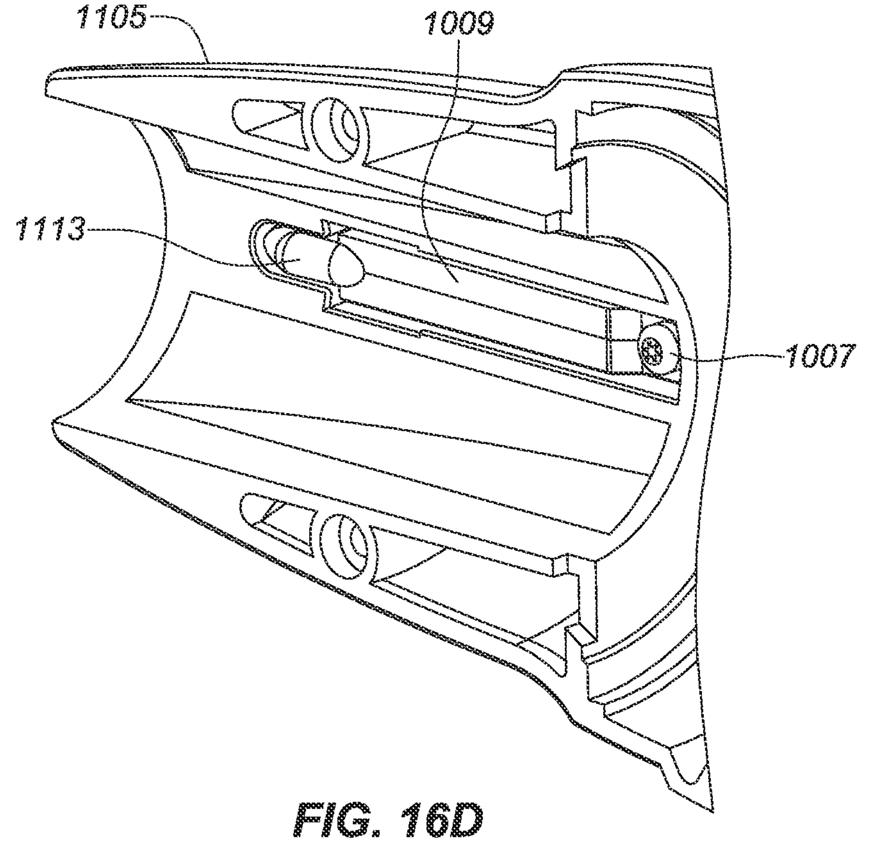
FIGS. 16D-16E are cross-sections of an embodiment of a handle portion of the present invention.
Figure 16E:
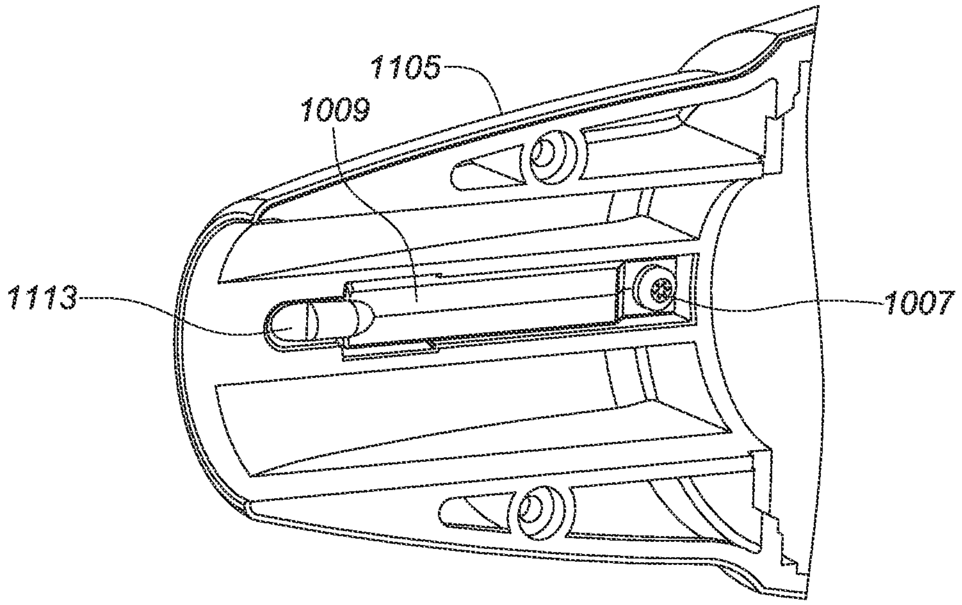
Figure 16F:
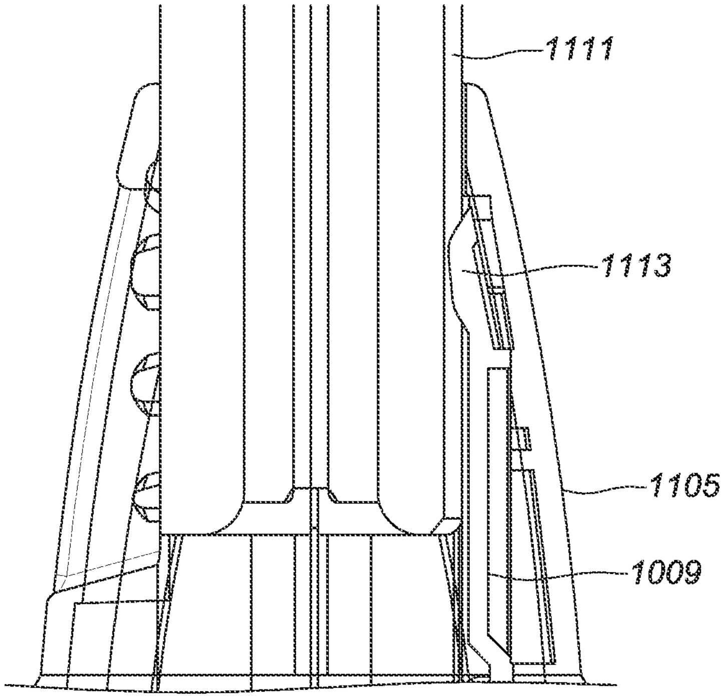
FIG. 16F is a coronal plane of an embodiment of a handle portion of the present invention.
Figure 16G:
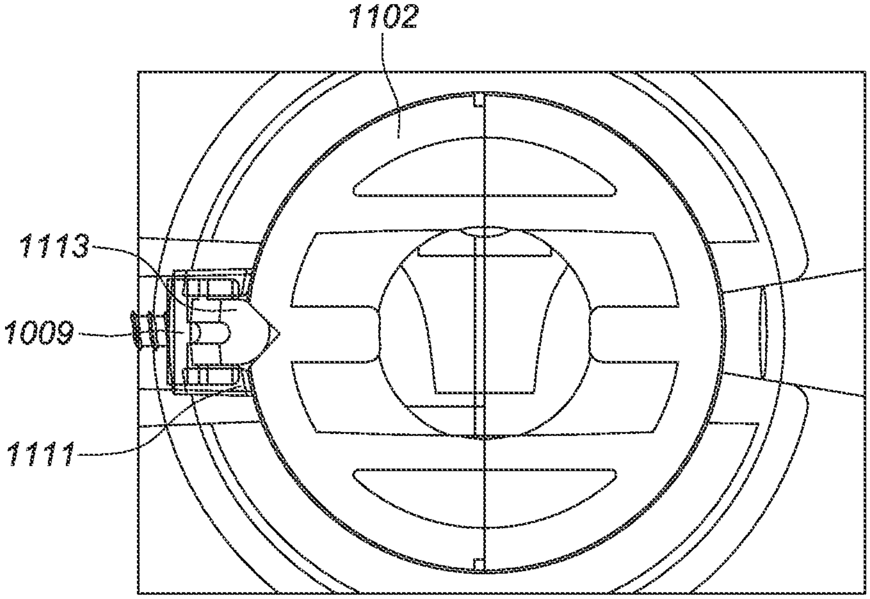
FIG. 16G is a transverse plane of an embodiment of a handle portion of the present invention.

Referring to FIGS. 16A-G, proximal control device 200 may include an anti-rotation mechanism that prevents outer shaft 120 from rotating with respect to inner shaft 130, if no rotation of outer shaft 130 is desired during implant delivery. Distal handle portion (or scope handle) 1102 may contain a groove 1111 that extends along a longitudinal axis of distal handle portion 1102 and is configured to receive a detent 1113 attached to a strut 1009 that is located on an inside surface of distal section 1105 of proximally located handle portion 1103. As seen in FIGS. 16D and 16E, strut 1009 is attached to the inside surface at a first end 1007 and extends laterally, terminating in detent 1113 at a second free end that is not attached to the inside surface. After distal handle portion 1102 and/or proximally located handle portion is rotated such that detent 1113 is housed within groove 1111, distal handle portion and proximally located handle portion 1103 are locked together. Distal handle portion 1102 cannot passively rotate relative to proximally located handle portion 1103 and proximally located handle portion 1103 cannot passively rotate relative to distal handle portion 1102, and thus, outer shaft 120 is not able to rotate passively relative to inner shaft 130 during implant delivery and/or deployment. Detent 1113 is deflectable. When it is desired to allow (passive or active) rotation of the outer shaft 120 relative to the inner shaft 130, as seen in FIG. 16C, additional force can be applied and distal handle portion 1102 can be rotated such that detent 1113 is deflected out of groove 1111 into body of distal handle portion 1102. For example, a user can overpower the anti-rotation mechanism by using their hands to rotate the scope handle 1102 free of detent 1113. When detent 1113 is not housed within groove 1111, distal handle portion 1102 and proximally located handle portion are able to rotate relative to one another and thus, outer shaft 120 is able to rotate relative to inner shaft 130.

Figure 7A:
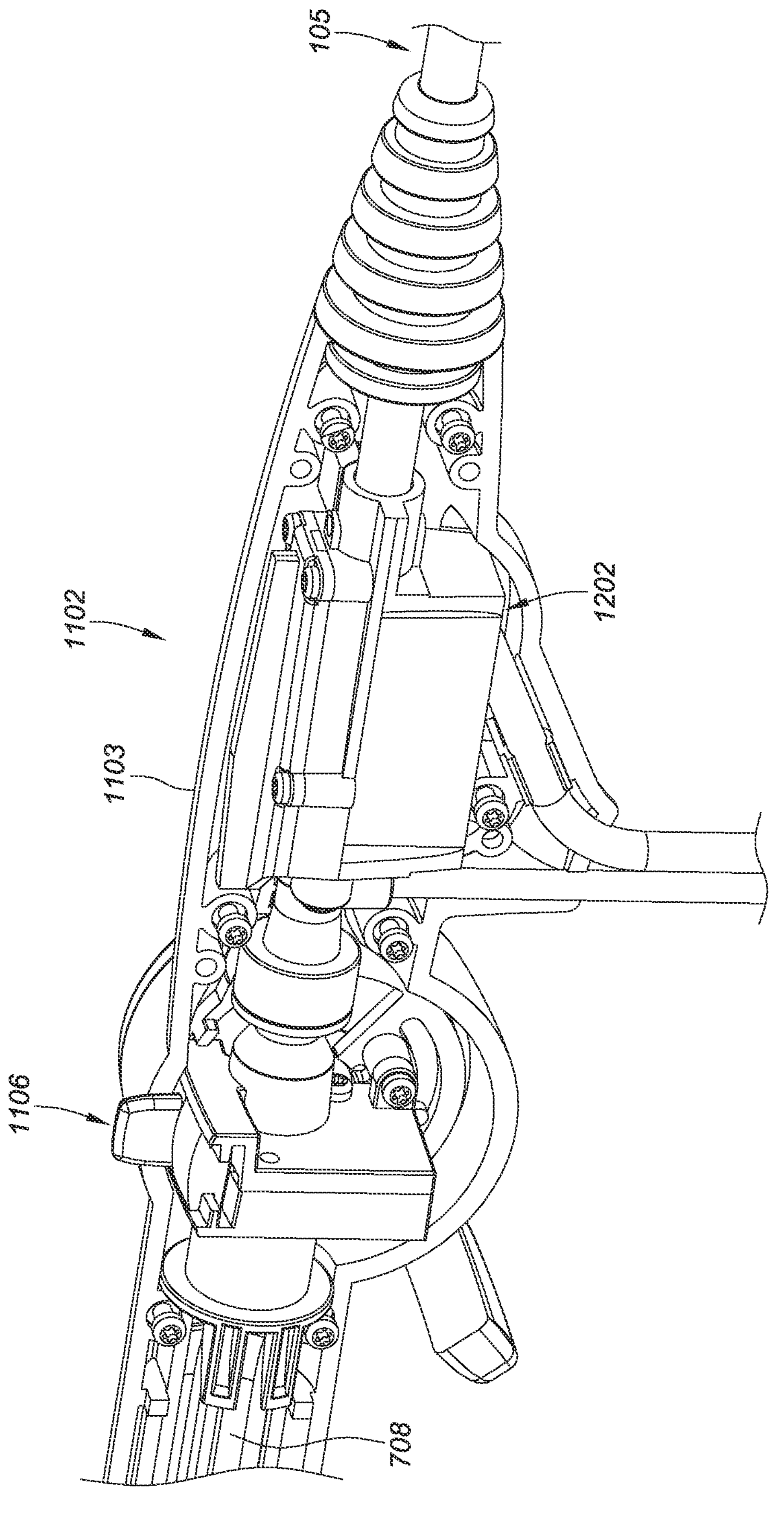
FIGS. 7A-8C are perspective views depicting example embodiments of components within a proximal control device.

FIG. 7A is an interior view of an example embodiment of movable portion 1102 of proximal control device 200 taken from a view that is reversed as compared to FIGS. 5A-5B. Proximal end region 105 of delivery device 103 is shown coupled with housing 1103 of movable portion 1102 at right, and multi-sided shaft 708 is shown at left. (Shaft 708 can be multi-sided to allow an interference fit with hub 707, although other configurations and securement techniques can be used such that shaft 708 is cylindrical (e.g., secured to hub 707 with adhesive). A coupling mechanism 1106 is mounted or formed within housing 1103 and will be described in more detail with respect to FIGS. 7B-7E. Also included within housing 1103 is imaging hardware 1202, which will be described in more detail with respect to FIGS. 9A-9B.

Figure 7B:
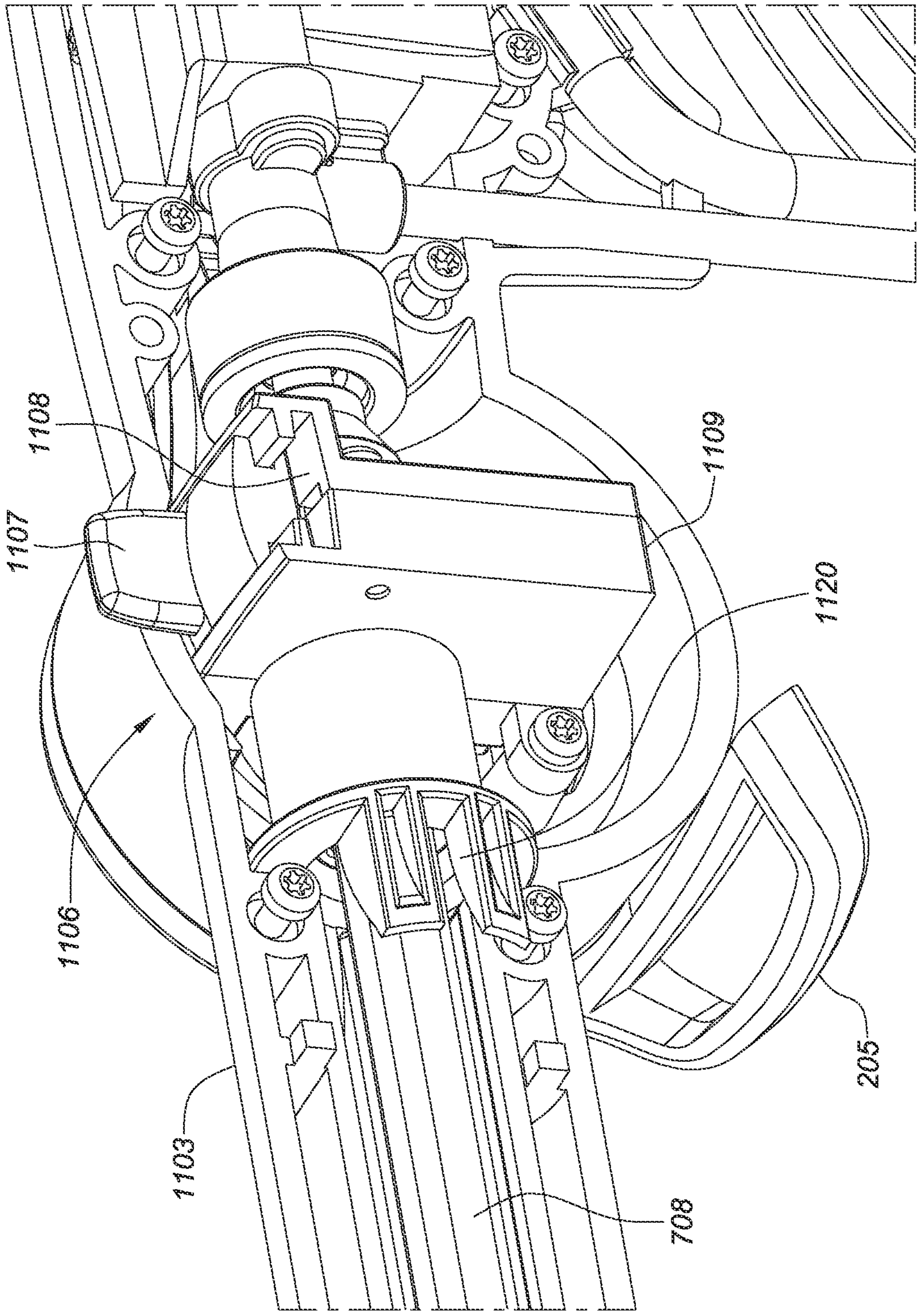
Figure 7C:
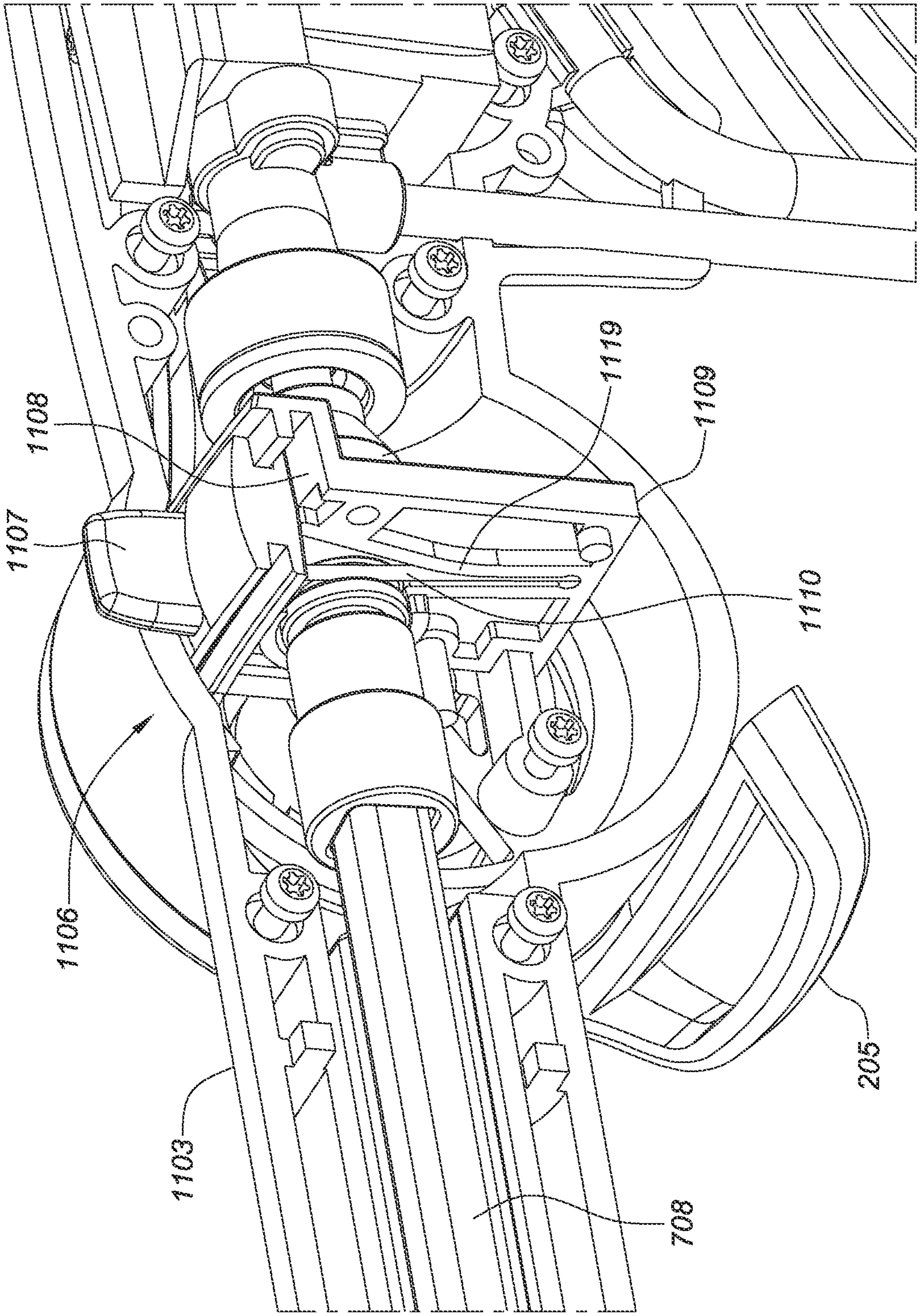
Figure 7D:
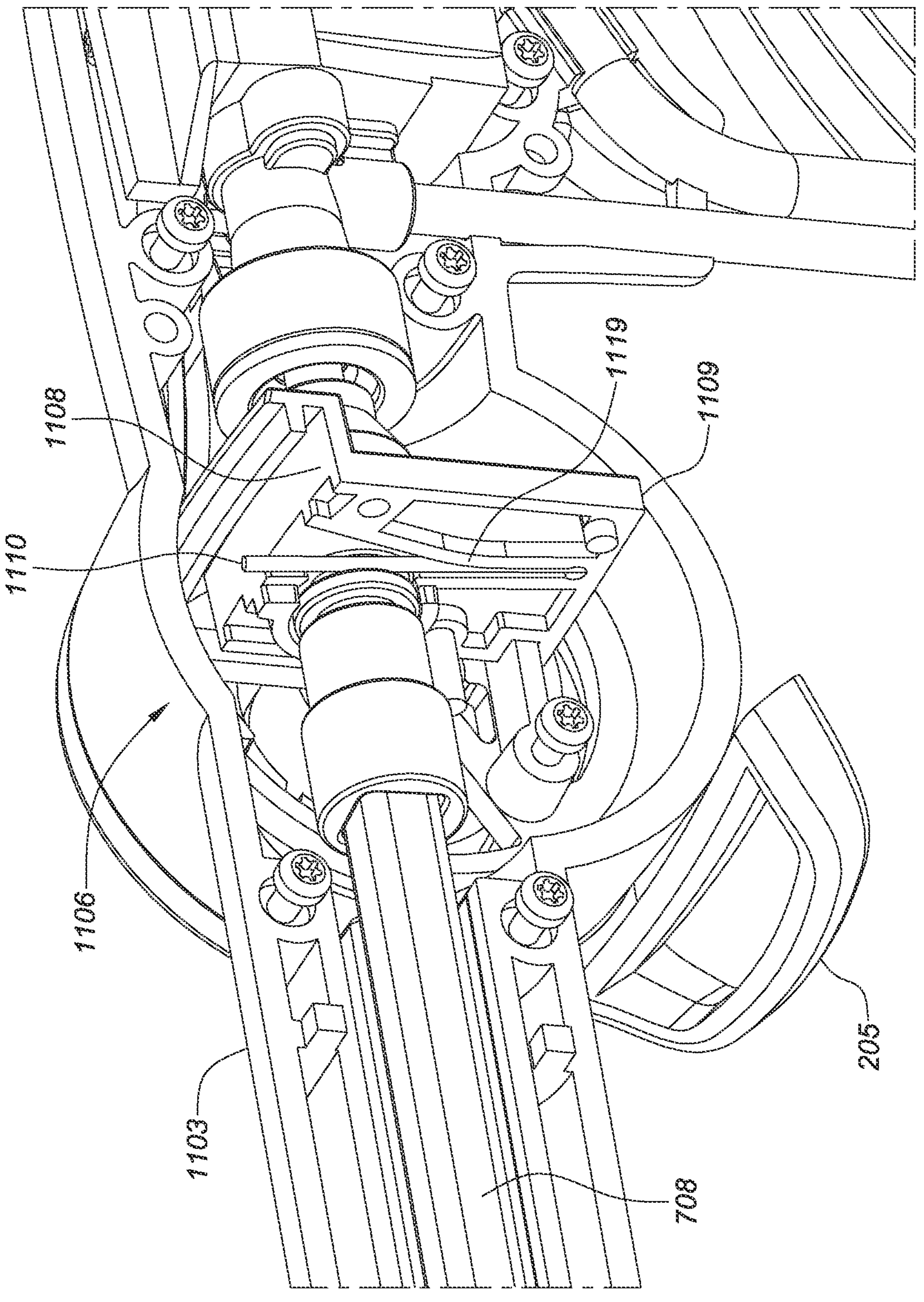
Figure 7E:
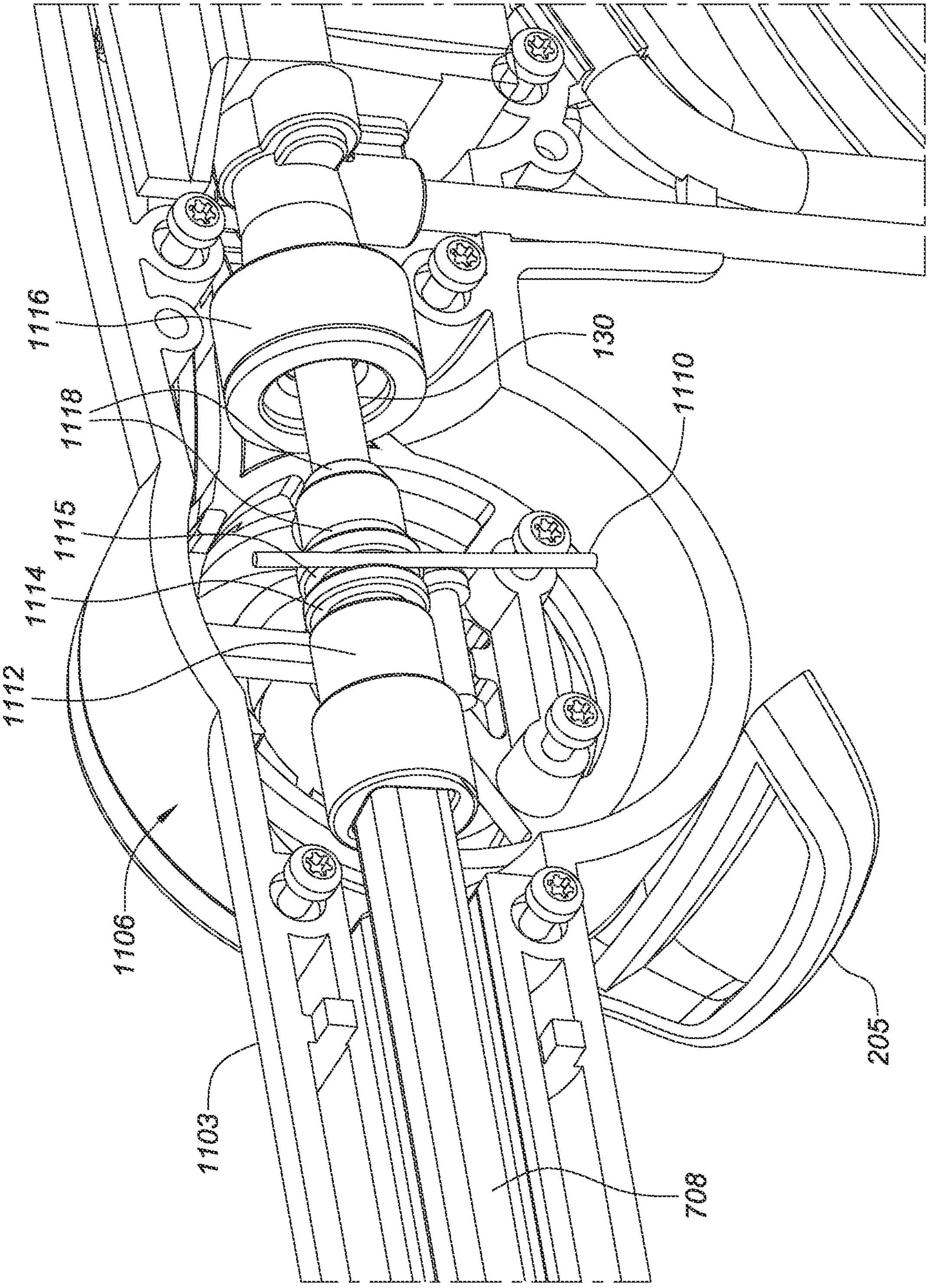

FIG. 7B is an interior view of coupling mechanism 1106 depicted from a closer perspective than FIG. 7A. Here, coupling mechanism 1106 includes a user actuator 1107 that is configured in this embodiment as a latch slidable within a track 1108 provided by housing 1109. FIG. 7C depicts coupling mechanism 1106 with a proximal side of housing 1109 removed to permit the interior components to be seen. FIG. 7D depicts the coupling mechanism 1106 of FIG. 7C also with latch 1107 removed, and FIG. 7E depicts the coupling mechanism 1106 of FIG. 7D with housing 1109 removed, to further case description.

Latch 1107 is coupled with an elastic, deflectable member 1110 that is seated within housing 1109. Movement of latch 1107 from a leftmost position to a rightmost position (as depicted here) causes member 1110 to bend against a sloped surface 1119. Member 1110 is biased towards a straight configuration (as shown in FIGS. 7C-7D) and release of latch 1107 in the rightmost position permits latch 1107 to return to the leftmost position by the elastic action of member 1110. Member 1110 can be configured as desired for the needs of the application. For example, in this embodiment member 1110 is a nitinol wire.

When in the leftmost position member 1110 can be received within one or more grooves in rotary adapter 1112. In the embodiment of FIG. 7E there are two grooves 1114 and 1115, each of which can receive member 1110 such that member 1110 can slide in grooves 1114 and 1115 as rotary adapter 1112 is rotated, but any longitudinal movement (advancement and/or retraction) of rotary adapter 1112 will cause likewise movement to member 1110.

Prior to use in the implantation procedure, the proximal end of inner shaft 130 is coupled with rotary adapter 1112, which in turn is coupled with multi-sided shaft 708, which is in turn coupled with the proximal portion 1103 of proximal control device 200. The outer shaft 120 is coupled with movable portion 1102, but portions 1103 and 1102 are separated and not coupled together. The medical professional or other user can advance the distal end of inner shaft 130 into movable portion 1102 of proximal control device 200 until a groove 1114 and/or 1115 of rotary adapter 1112 engages with deflectable member 1110. The insertion of inner shaft 130 through portion 1102 can be accomplished with the aid of one or more ramps 1120 depicted in FIG. 7B. The distal end 1118 of rotary adapter 1112 can be tapered or necked down in one or more regions to assist in this insertion by deflecting member 1110 until the first groove 1115 is located immediately adjacent thereto at which point member 1110 will snap into the groove. Upon engagement of wire 1110 with one of grooves 1114 or 1115, movable portion 1102 is coupled with proximal portion 1103 of proximal control device 200. In certain embodiments, at this point, proximal control device 200 is assembled and ready for use in the implantation procedure.

Example Embodiments of Imaging Devices and Use

In certain example embodiments, the coupling of movable portion 1102 (which is secured to outer shaft 120) to rotary adapter 1112 (which in turn is secured to multi-sided shaft 708, guide member 706, and inner shaft 130), causes outer shaft 120 to track the movements of inner shaft 130. As described with respect to FIG. 2A, an imaging device and illumination device (see FIGS. 9A-9B) can be placed in one or more of lumens 122-124 at the distal end of outer shaft 120. These devices can be mounted at the distal terminus of their respective lumens (or share a lumen), the locations of which are a small distance proximal to the distal terminus of inner shaft 130 from which implant 102 exits during delivery. As inner shaft 130 moves proximally in a longitudinal direction, outer shaft 120 also moves proximally in a longitudinal direction with the same spacing maintained between their relative distal terminuses. Conversely, as inner shaft 130 moves distally outer shaft 120 also moves distally with the same spacing maintained (i.e., at the same rate). As such, system 100 allows the delivery of implant 102 from inner shaft 130 to be imaged with a constant spacing from the distal terminus of inner shaft 130. Because grooves 1114 and 1115 are annular (e.g., ring-like extending about the periphery of rotary adapter 1112) inner shaft 130 is permitted to rotate without causing like rotation in outer shaft 120. Deflectable member 1110 simply slides along the respective groove 1114 or 1115.

If the user or medical professional desires the imaging device to be placed at a different spacing from the distal terminus of inner shaft 130, coupling mechanism 1106 can be used to release the coupling between movable portions 1102 and 1103, and movable portion 1102 can be moved such that a different groove engages with deflectable member 1110. For example, disengaging groove 1115 and engaging with groove 1114 will increase the spacing between the imaging device at the distal terminus of outer shaft 120 and the distal terminus of inner shaft 130, thus allowing the user to image with a relatively wider field of view. This feature provides the user with the ability to adjust the field of view. Coupling mechanism 1106 can be coupled in a first position corresponding to a first one of grooves 1114 and 1115, and if the imaging field of view is not optimal, the user can uncouple mechanism 1106 and switch to a second position corresponding to the other one of grooves 1114 and 1115. Although in the embodiments described herein only two grooves 1114 and 1115 are present, any number of one, two, three, four, or more grooves can be used, each being independently selectable from the others and each corresponding to a different position and field of view. The ability of the imaging and illumination devices to automatically move in lockstep with the longitudinal movement of inner shaft 130 during deployment can be used with any embodiment described herein.

Figure 8A:
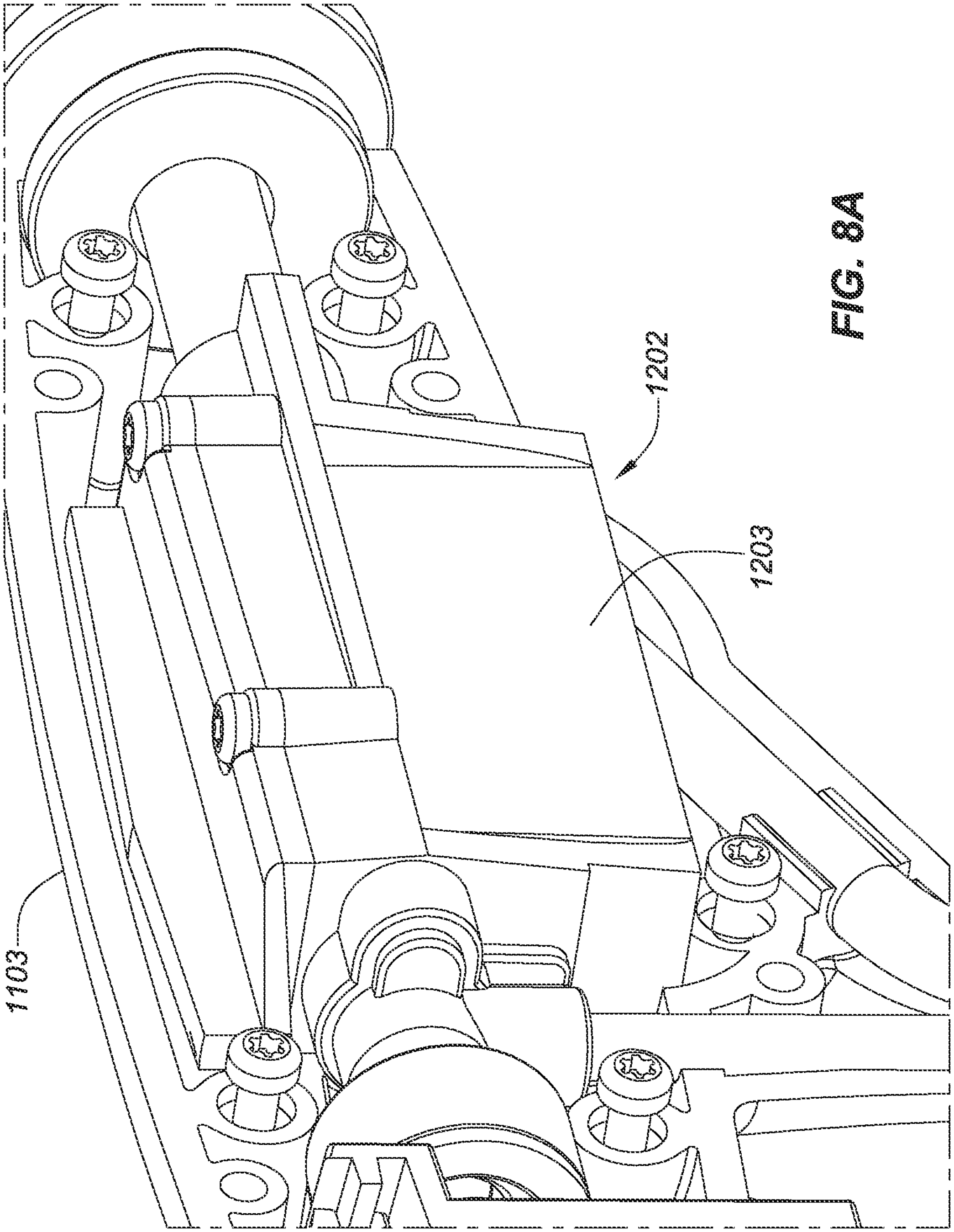
Figure 8B:
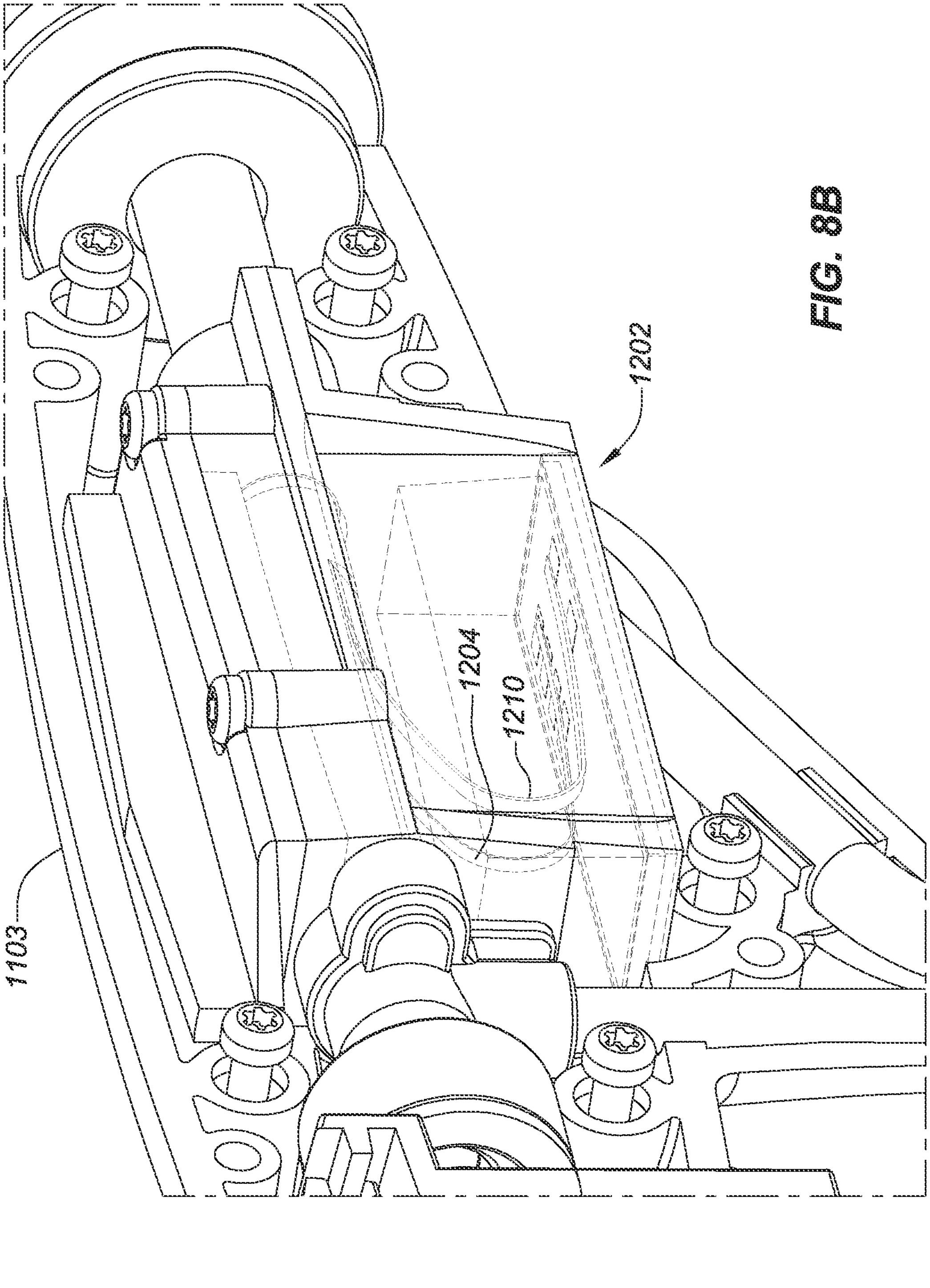
Figure 8C:
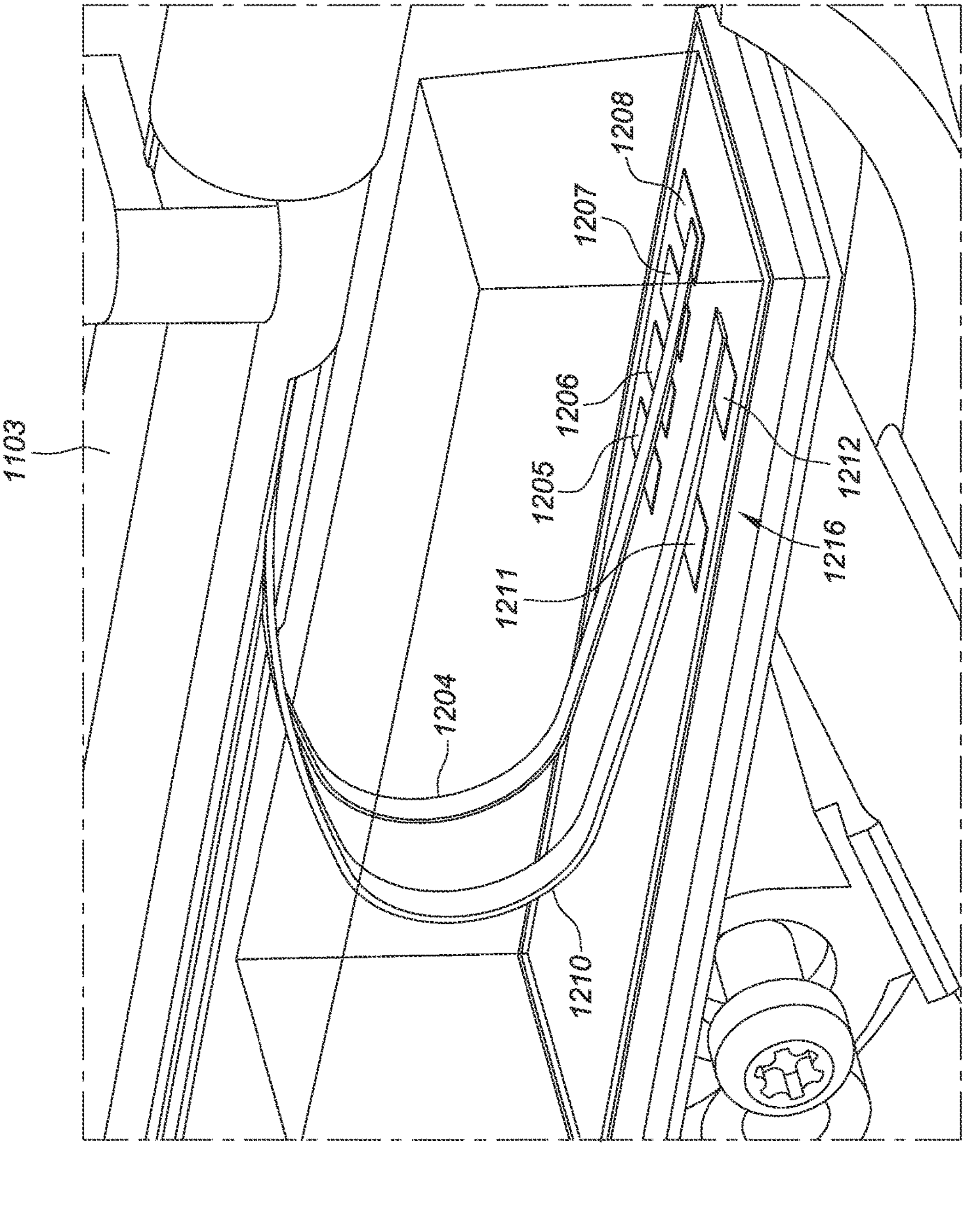
Figure 9A:
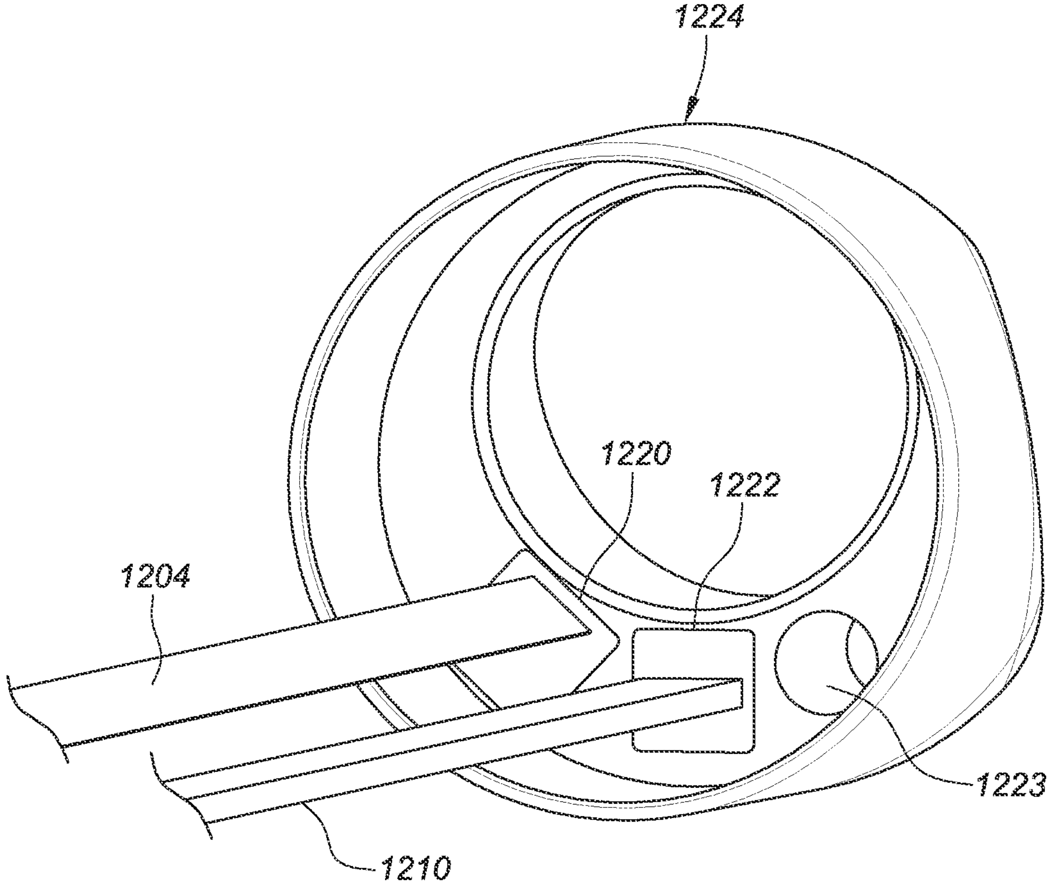
FIGS. 9A-9B are perspective views depicting an example embodiment of a distal end region of an outer tubular member.
Figure 9B:
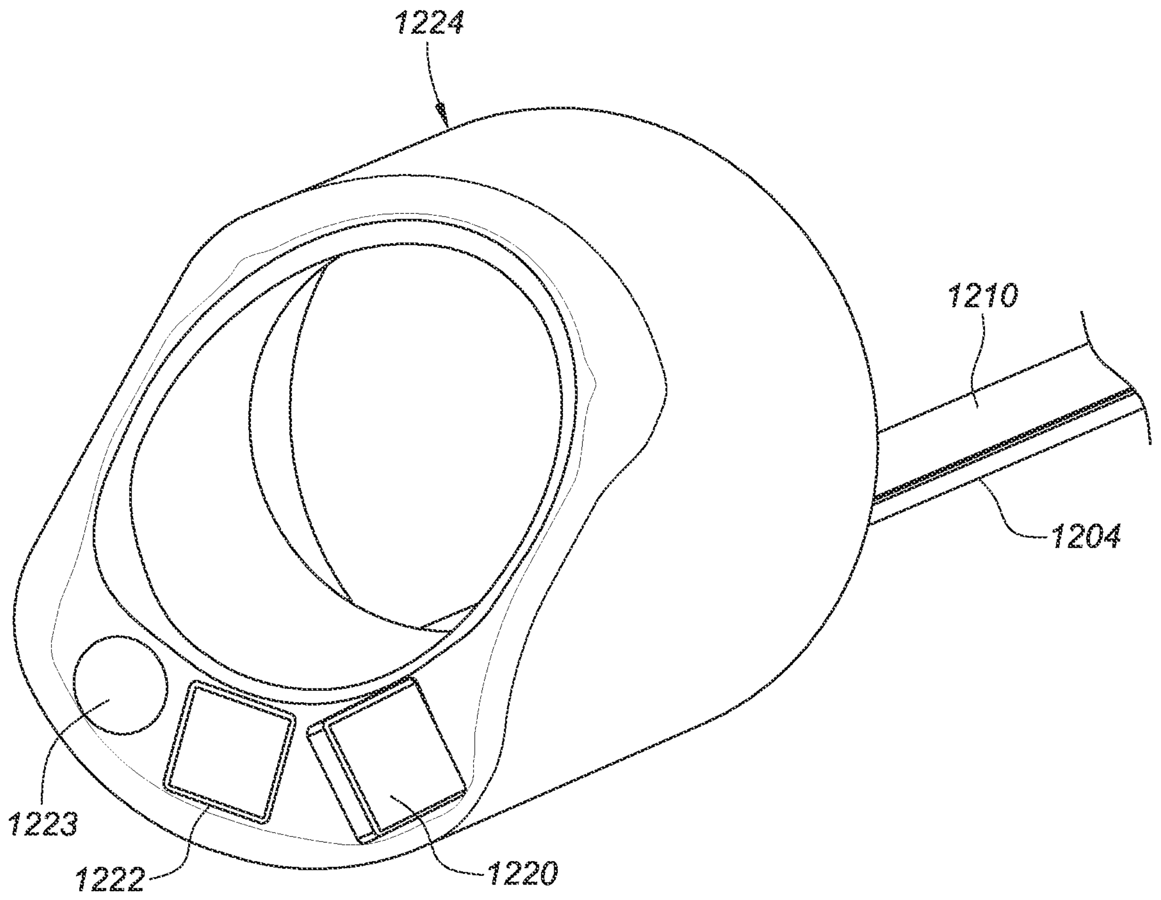

FIG. 8A depicts a housing 1203 for imaging hardware 1202. FIG. 8B depicts the components on the interior of housing 1203 and FIG. 8C depicts these components from a closer perspective. FIG. 9A is a perspective view depicting the proximal side of a distal end region of outer tubular member 120, and FIG. 9B is a perspective view depicting the distal side of the distal end region of outer tubular member 120. A first bus 1204, which in this embodiment is in the form of a ribbon cable, is connected at its distal end (FIG. 9A) to an imaging device 1220 in a distal end region tip 1224 of outer tubular member 120 (not shown). First bus 1204 can be routed through a lumen (e.g., one of lumens 122-124) of outer tubular member 120 and have its proximal end is connected to one or more contacts (FIG. 8C), in this example four contacts 1205-1208 for power, ground, the received signal, and a clock.

A second bus 1210, which in this embodiment is also in the form of a ribbon cable, is connected at its distal end (FIG. 9A) to an illumination device 1222 in distal end region tip 1224. Second bus 1210 can be routed through the same or a different lumen of outer tubular member 120 (e.g., one of lumens 122-124) and have its proximal end connected to one or more contacts (FIG. 8C), in this example two contacts 1211 and 1212 for power and ground. These contacts are located on a printed circuit board 1216 that can have additional imaging hardware (not shown) coupled thereto, including passive RLC components and active components (e.g., transistors, diodes, and/or semiconductor chips). The output circuitry to transmit the received images can be wireline circuitry that outputs the image via a cable to a display or wireless circuitry that transmits the images wirelessly to a local receiver with a display. A flush port lumen 1223 is also shown in FIGS. 9A-9B. The order of the positions of imaging device 1220, illumination device 1222, and flush port lumen 1223 can be rearranged from the positions described and shown here.

Figure 10A:
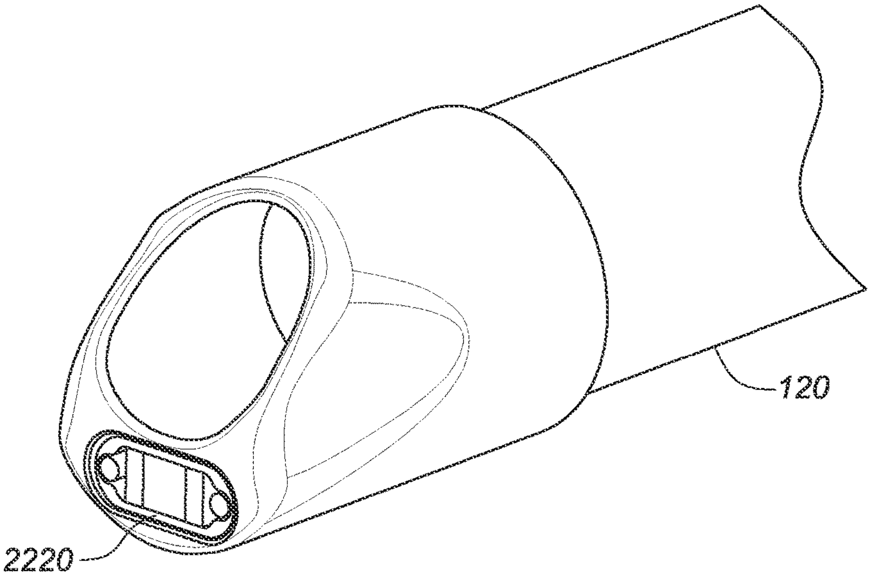
FIGS. 10A-10B are perspective views depicting an example of a telescoping imaging module.
Figure 10B:
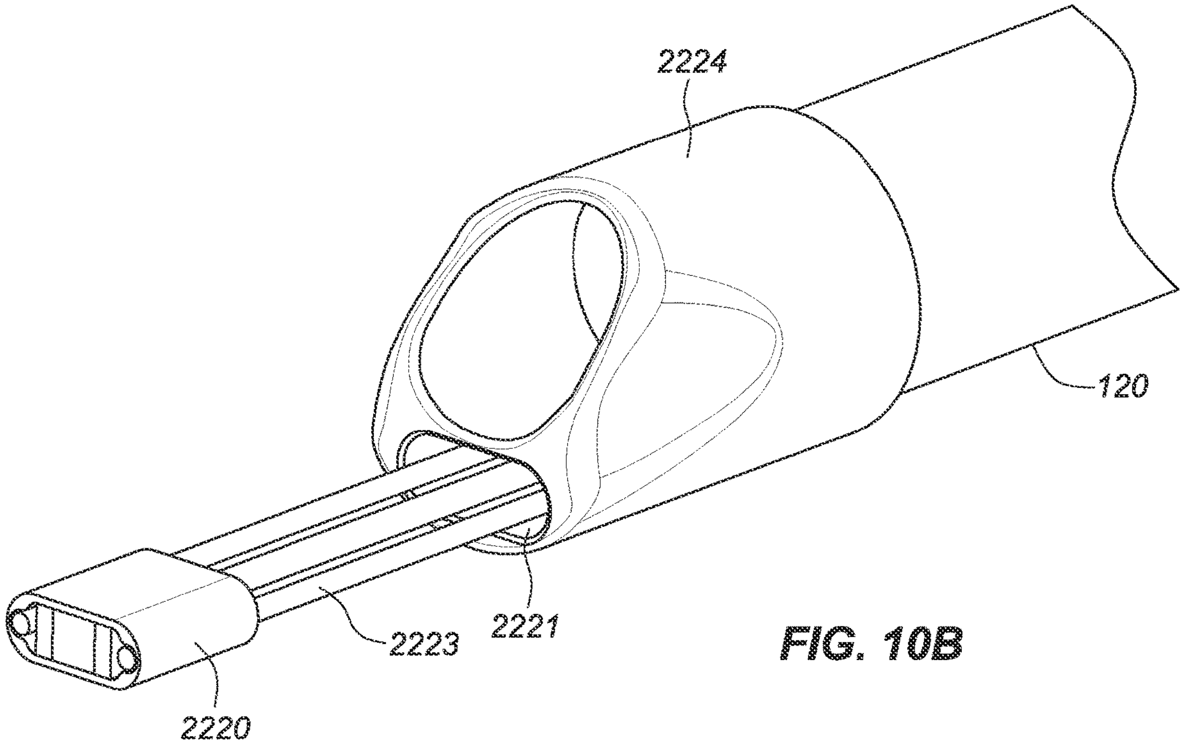
Figure 10C:
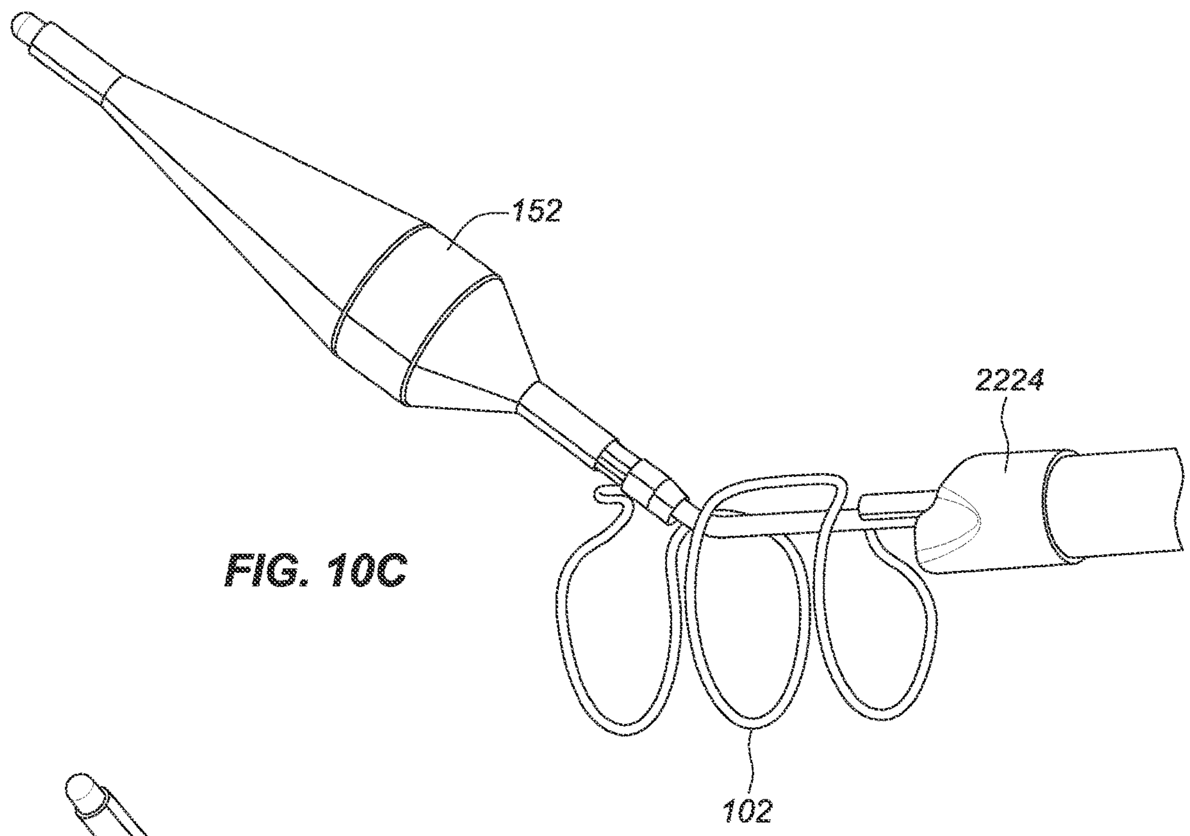
FIGS. 10C-10D are perspective views depicting examples of a delivery system with a telescoping imaging module.
Figure 10D:
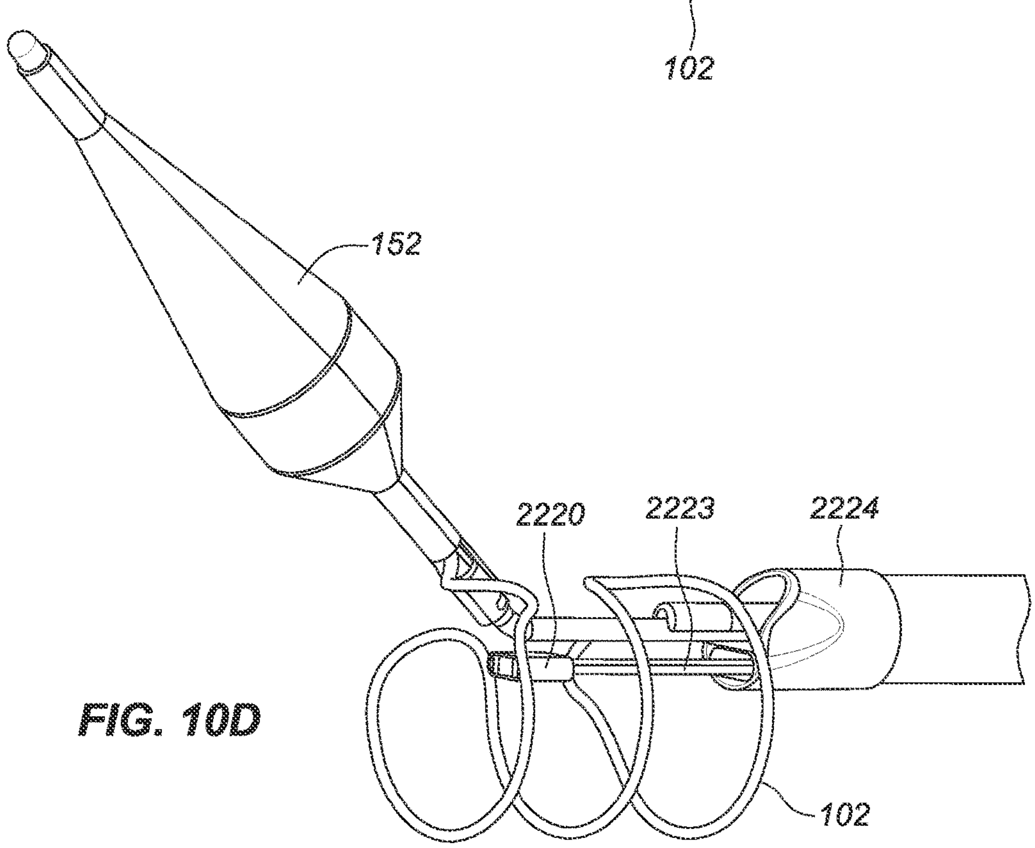

In an alternative embodiment, the imaging device may be part of a telescoping module. The user or medical professional may desire to move the imaging device because, e.g., the scope's view of all or part of the implant is obstructed by tissue. FIGS. 10A-10B are perspective views depicting the distal side of the distal end region of outer tubular member 120. The telescoping imaging module 2220 may include camera and a light source, such as LEDs, mounted to at least one, alternatively at least two, alternatively at least three elongate members 2223 that extend from lumen 2220 of outer tubular member 120. The telescoping imaging module may extend between about 0 to about 5.0 cm, alternatively between about 0.25 cm to about 5.0 cm, alternatively about 0.5 to about 4.0 cm from the distal end region tip 2224 of outer tubular member 120. As seen in FIGS. 10C-10D, telescoping imaging module 2220 may be advanced proximally through the implant without affecting the positions of the delivery system or implant 102. Thus, the final position of implant 102 can be evaluated prior to release of implant 102 from delivery device 103. Moreover, telescoping imaging module 2220 may be allow for further evaluation of the positioning of implant 102 relative to key anatomical landmarks, such as the external urethral sphincter and bladder neck, after it is released from delivery device 103 without the risk of passing the larger outer tubular member 120 through implant 120.

As described in other embodiments, one or more buses can be routed through a lumen of outer tubular member 120. The distal ends of the one or more buses are connected to the telescoping imaging module 2220. The proximal ends of the one or more buses are connected to one or more contacts, e.g., for power, ground, the received signal, and/or a clock. These contacts are located on a printed circuit board that can have additional imaging hardware (not shown) coupled thereto, including passive RLC components and active components (e.g., transistors, diodes, and/or semiconductor chips). The output circuitry to transmit the received images can be wireline circuitry that outputs the image via a cable to a display or wireless circuitry that transmits the images wirelessly to a local receiver with a display.

Figure 11A:
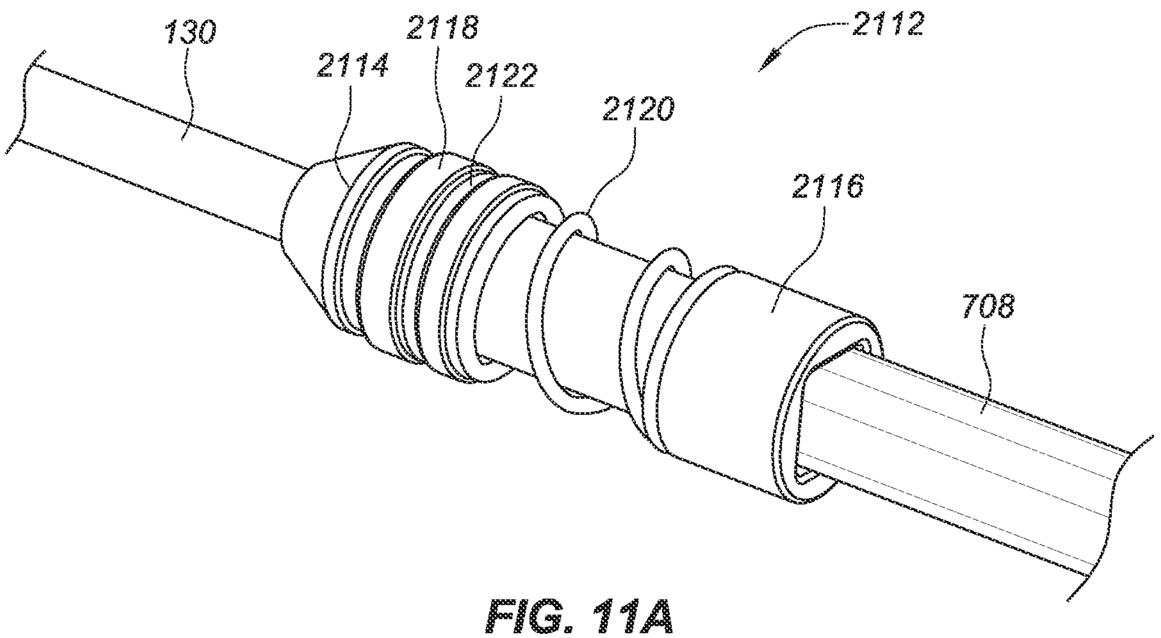
FIGS. 11A-11C are perspective views of an example embodiment of a rotary adapter.
Figure 11B:
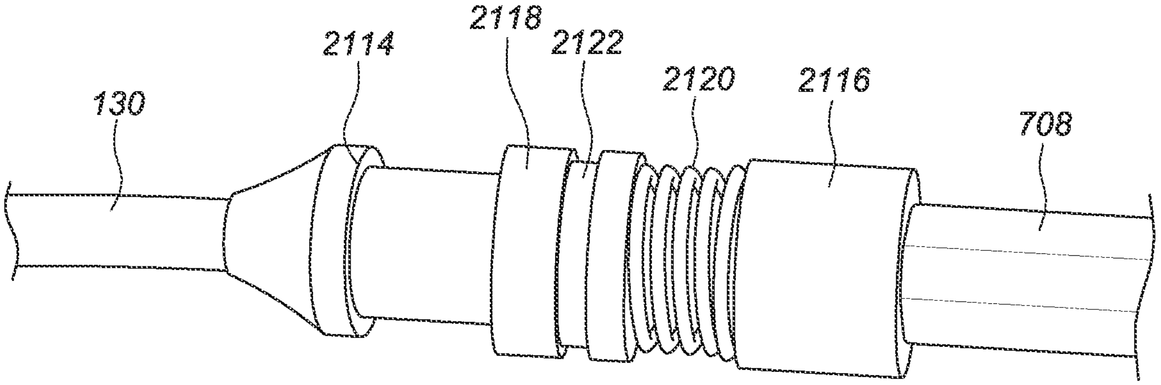
Figure 11C:
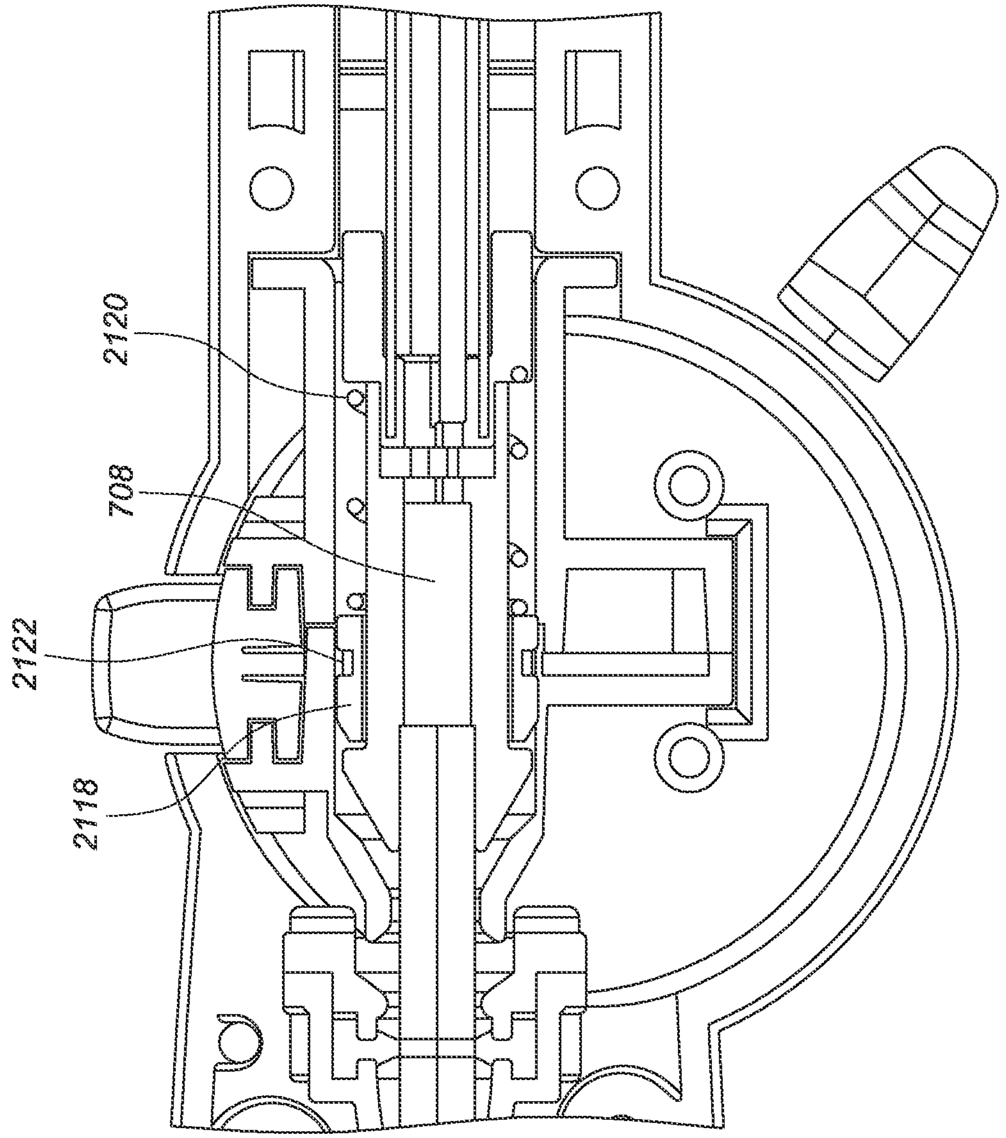

In an alternative embodiment, as seen in FIGS. 11A-11C, the imaging device may be adjustable in a proximal and distal direction with respect to the position of the implant 102 and/or delivery system in order to temporarily view a different portion of the implant 102. The imaging device and the delivery system may be connected through a spring-loaded connection, such as rotary adapter 2112. As previously explained with respect to FIG. 7E, the proximal end of inner shaft 130 is coupled with a rotary adapter, which in turn is coupled with multi-sided shaft 708, which is in turn coupled with the proximal portion 1103 of proximal control device 200. As seen in FIGS. 11A-11B, in an alternative embodiment, rotary adapter 2112 includes a distal component 2114, proximal component 2116, sliding component 2118, and spring 2120. Distal component 2114 is coupled to inner shaft 130 and may have a conical shape that tapers from the proximal to the distal end. Sliding component 2118, which is located adjacent to and proximal of distal component 2114, has an annular or ring shape. The imaging device (not shown) can be coupled to annular groove 2122 of sliding component 2118. Spring 2120 is located between sliding component 2118 and proximal component 2116, proximal of and adjacent to sliding component 2118. Proximal component 2116 is located proximal of and adjacent to spring 2120 and is coupled with multi-sided shaft 708.

Figure 12A:
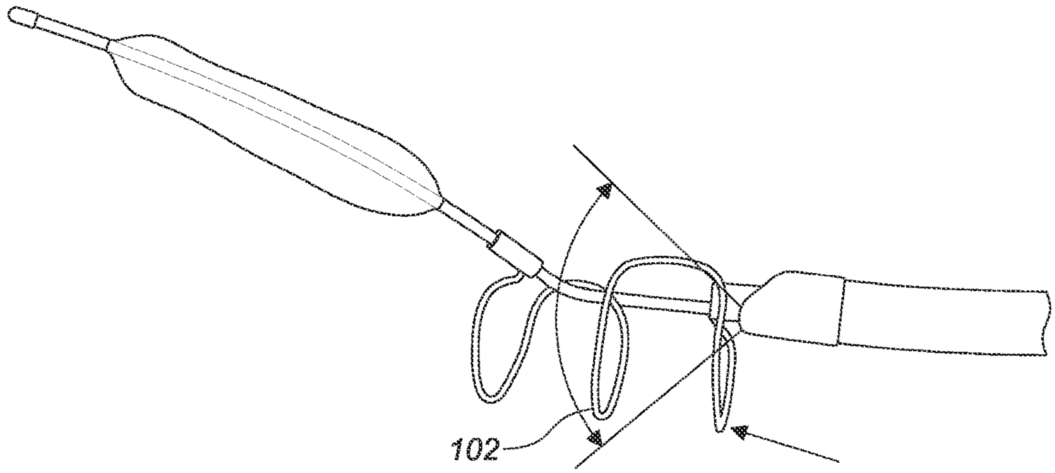
FIGS. 12A-12B are perspective views of example embodiments of delivery systems with the scope positioned at different locations.
Figure 12B:
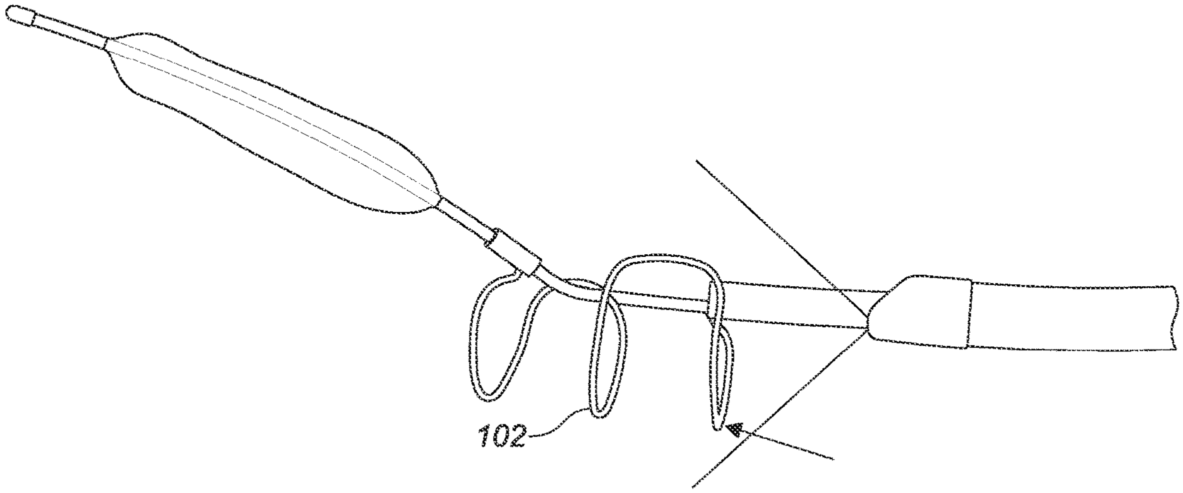

In use, the scope, which is connected to sliding component 2118, is pulled back in a proximal direction and spring 2120 is compressed manually by the user by holding the outside handle 1102 and pulling the handle backwards relative to the delivery system handle 1103. (See FIGS. 11A-11B). When the scope is released, spring 2120 will decompress and the scope will return to its rest position (where spring 2120 uncompressed). As seen in FIG. 12A, when the scope is in the default (at rest) position, the bottom of the last ring of implant 102 is not within the scope's view and the user is unable to visualize the bottom of the last ring relative to the anatomy. When the scope is positioned in a proximal direction relative to the delivery system using rotary adapter 2112, as seen in FIG. 12B, the field of view now includes the bottom of the last ring of implant 102 and the user is able to better assess the placement of implant 102 before releasing implant 102 from the delivery device.

In an alternative embodiment, spring 2120 is located between distal component 2114 and sliding component 2118. In use, the scope may be advanced forward in a distal direction by compressing spring 2120. When the scope is released, spring 2120 will decompress and the scope will return to its rest position (where spring 2120 uncompressed).

Figure 15:
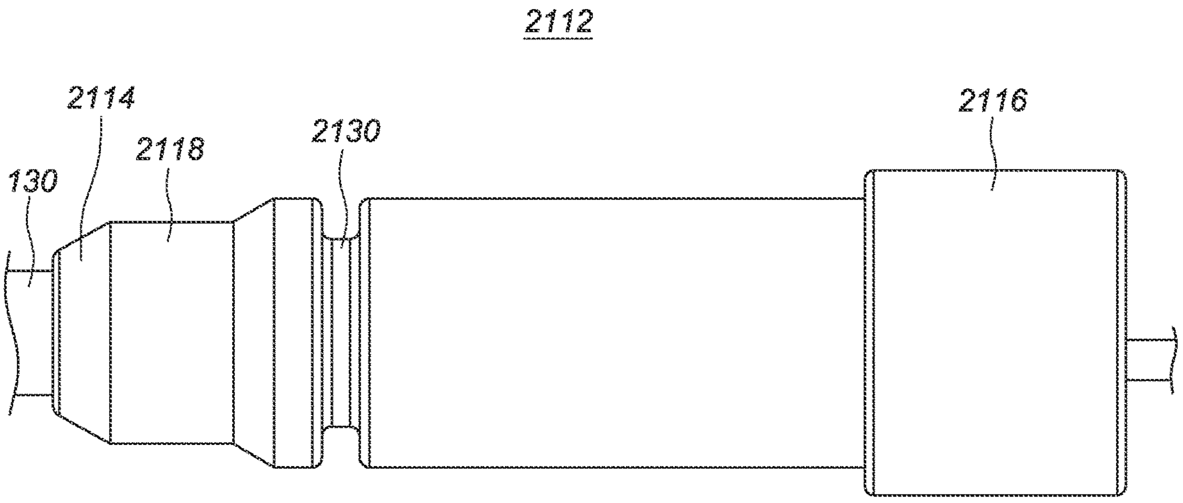
FIG. 15 is a side view of an example embodiment of a rotary adapter.

In an alternative embodiment, the rotary adapter may conduct electricity and be designed to connect receive power from an external source or connect with the imaging device's printed circuit board. As seen in FIG. 15, the rotary adapter may include an electrical contact plate or ring 2130. For example, an electrical contact plate or ring may be included in sliding component 2118. A bus, e.g., in the form of a ribbon cable, may be connected at its proximal end to the electrical contact plate or ring and at its distal end to a light source, e.g., LED, mounted onto the distal end of inner shaft 130 or distal control member or tether 140. Thus, electrical power is routed via inner shaft 130 or tether shaft 140. In an alternative embodiment, the electrical contact plate or ring may be included in rotary adapter 1112, as described with reference to FIG. 7E.

Example Embodiments of Implant Placement

Figure 13:
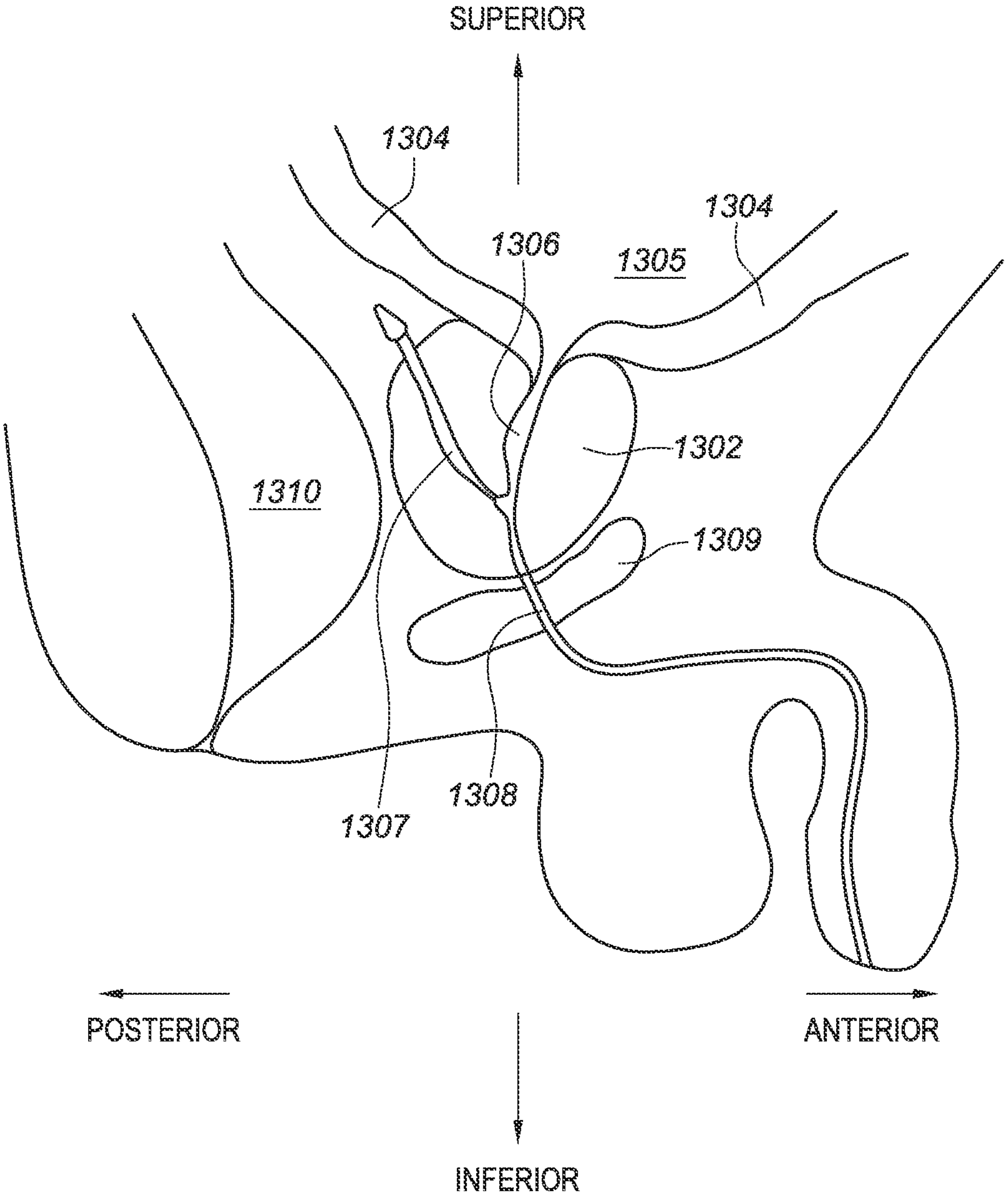
FIG. 13 as an example cross-section of the male anatomy.

All the embodiments of system 100 described herein can be used to deliver implant 102 to various locations in proximity to the prostate gland, or other locations within the human anatomy. FIG. 13 is a cross-section of the male anatomy that provides context for use in describing various examples of implantation locations within the prostatic urethra. Here, prostate gland 1302 is centrally located with bladder wall 1304 and bladder 1305 located superiorly. The prostatic urethra 1306 extends inferiorly from bladder 1305 past ejaculatory duct 1307 and through prostate gland 1302. The prostatic urethra 1306 becomes the membranous urethra 1308 at the general location of the external urethral sphincter 1309 and continues on to exit the body. The rectum is indicated by 1310.

Figure 14A:
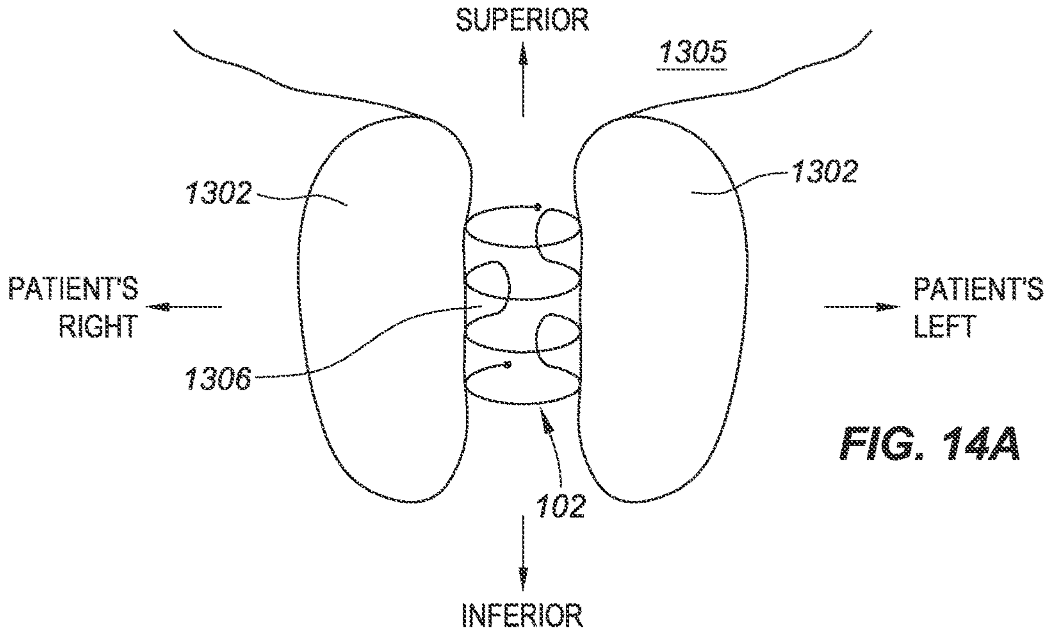
FIG. 14A is an example cross-section of the male anatomy having an example embodiment of an implant deployed therein.

FIG. 14A is a cross-section rotated from the viewpoint of FIG. 13 such that the posterior direction extends into the page in the anterior direction extends out of the page. Here an example embodiment of implant 102 is shown positioned within prostatic urethra 1306. Implant 102 is generally positioned centrally within prostatic urethra 1306 as viewed from this perspective, in other words, generally an equal distance from the superior and inferior edges of prostate gland 1302. Placement of implant 102 is generally at the discretion of the medical professional and can be offset either superiorly or inferiorly from the positions shown here, however a position within the prostatic urethra 1306 is generally preferred.

Figure 14B:
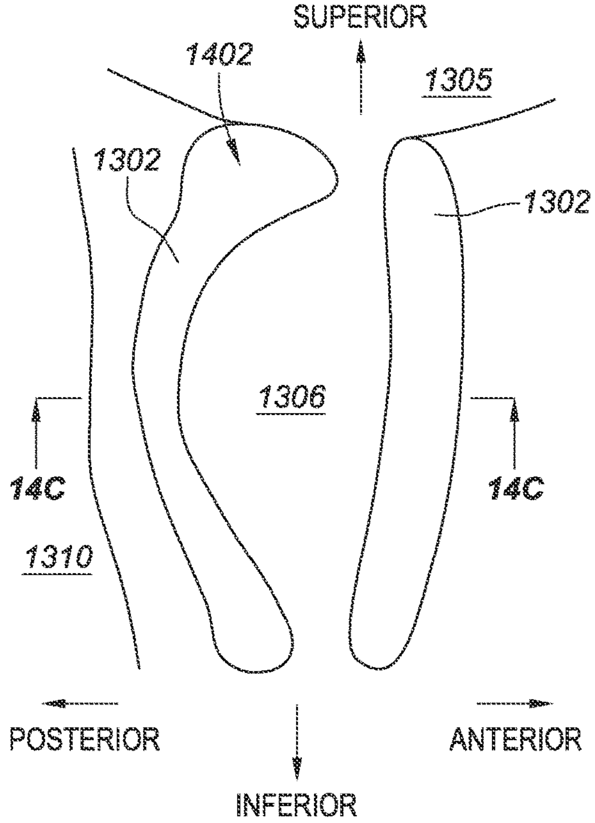
FIG. 14B is an example cross-section of the male anatomy and FIG. 14C is an example cross-section of the male anatomy taken along line 14C-14C of FIG. 14B.
Figure 14C:
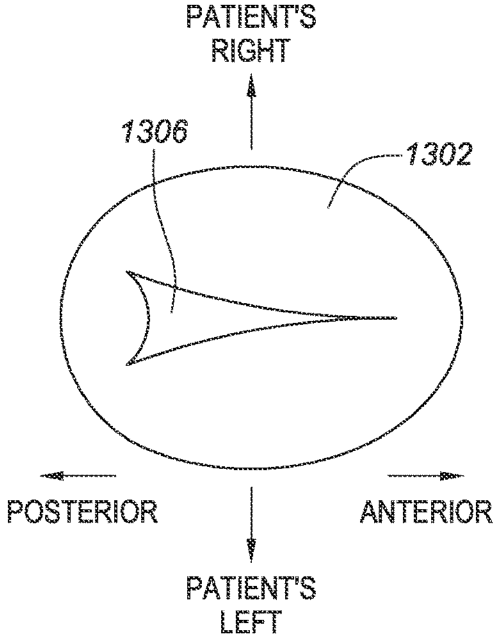

FIG. 14B depicts the area of prostate gland 1302 from generally the same perspective as that of FIG. 13, but with more detail. Here, prostate gland 1302 is in an enlarged state with a median lobe 1402 that protrudes into prostatic urethra 1306. FIG. 14C is a cross-section taken along line 14C-14C of FIG. 14B and shows the slit-like nature of prostatic urethra 1306 in this enlarged prostate gland 1302 where the width of urethra 1306 widens as it progresses from the anterior to the posterior side.

Figure 14D:
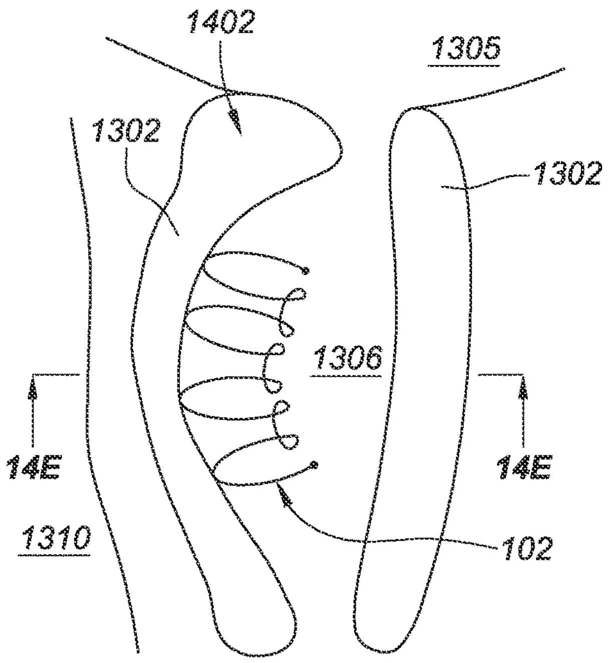
FIG. 14D is an example cross-section of the male anatomy having an example embodiment of an implant deployed therein and FIG. 14E is an example cross-section of the male anatomy taken along line 14E-14E of FIG. 14D.
Figure 14E:
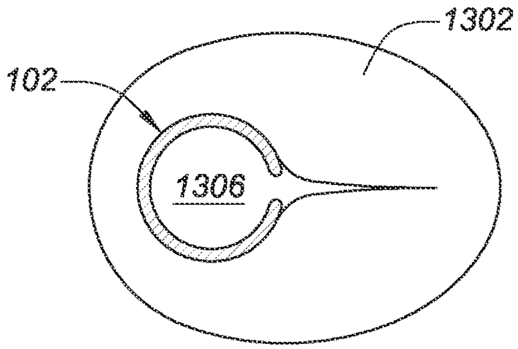

FIG. 14D depicts an example embodiment of a posteriorly placed implant 102 within the example anatomy described with respect to FIG. 14B and FIG. 14E is a cross-section taken along line 14E-14E of FIG. 14D. As can be seen here, implant 102 is placed generally along the posterior most surface of the prostatic urethra 1306. Implant 102 is sized to have a maximum diameter that is less than the width of prostatic urethra 1306 at its maximum central width (e.g., less than 50% of the width, less than 65% of the width, less than 80% of the width, etc.) such that implant 102 can be described as residing substantially on the posterior side of prostatic urethra 1306, and not in contact with the anterior most side of urethra 1306. The implications of this placement are shown in FIG. 14E where the opening through prostate gland 1302 that is created by implant 102 is positioned primarily on the posterior side of prostate gland 1302 and urethra 1306.

Figure 14F:
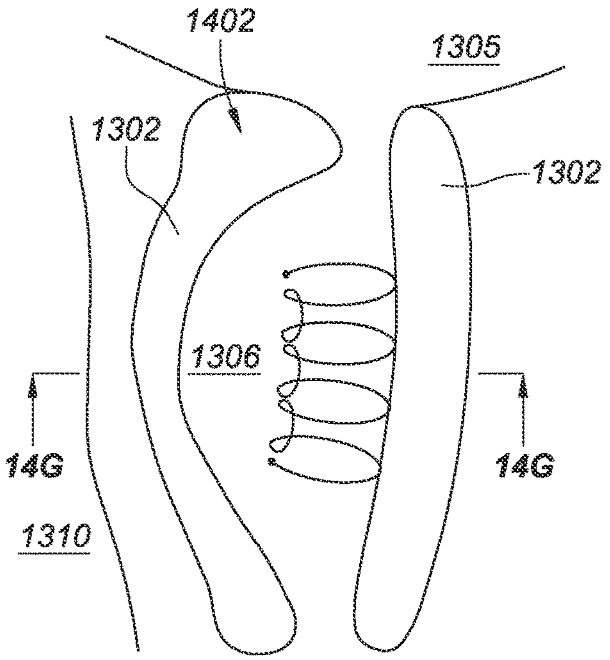
FIG. 14F is an example cross-section of the male anatomy having an example embodiment of an implant deployed therein and FIG. 14G is an example cross-section of the male anatomy taken along line 14F-14F of FIG. 14G.
Figure 14G:
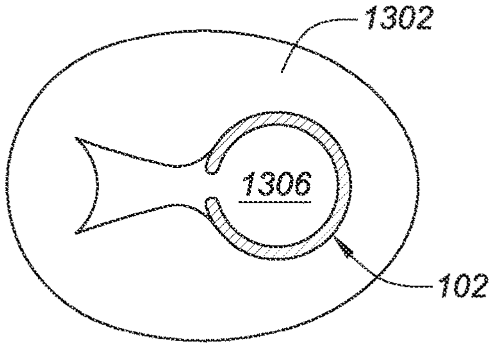

FIG. 14F depicts an example embodiment of an anteriorly placed implant 102 within the example anatomy described with respect to FIG. 14B and FIG. 14G is a cross-section taken along line 14G-14G of FIG. 14E. As can be seen here, implant 102 is placed generally along the anterior most surface of prostatic urethra 1306. Implant 102 can be sized to have a maximum diameter that is less than the width of prostatic urethra 1306 at its maximum central width (e.g., less than 50% of the width, less than 65% of the width, less than 80% of the width, etc.) such that implant 102 can be described as residing substantially on the anterior side of prostatic urethra 1306, and not in contact with the posterior most side of urethra 1306. The implications of this placement are shown in FIG. 14G where the opening through prostate gland 1302 that is created by implant 102 is positioned primarily on the anterior side of prostate gland 1302 and urethra 1306. With both the posterior placement and the anterior placement, implant 102 can still be placed generally centrally with respect to prostate gland 1302 as shown in FIG. 14A. Deployment of implant 102 in a posterior or anterior position is generally at the discretion of the medical professional. Other variations of placement can also be used including placements that are centrally located between the posterior most side and interior most side of urethra 1306, as well as variations in sizing such that implant 102 has a relatively larger or smaller diameter with respect to prostate 1302 than shown here.

The embodiments described herein are restated and expanded upon in the following paragraphs without explicit reference to the figures. In many example embodiments, a system for delivering an implantable device is provided, where the system includes a delivery device including: an outer tubular member; an inner tubular member having a first inner lumen and a second inner lumen, the inner tubular member being slidable within the outer tubular member, where the first inner lumen is adapted to house an elongate grasper member configured to releasably couple with a proximal portion of an implant; and a distal control member slidable within the second inner lumen, where the distal control member includes a retainer configured to releasably couple with a distal portion of the implant.

In some embodiments, the implant is configured to maintain a prostatic urethra in an at least partially open state. In some embodiments, the implant has a body including first and second ring-shaped structures and an interconnect that extends between the first and second ring-shaped structures. The body of the implant can be only a single wire. The implant can include a distal engagement member configured to releasably couple with the retainer and/or a proximal engagement member configured to releasably couple with the elongate grasper member. In some embodiments, the implant includes a wire-like distal engagement member that extends proximally away from a distal-most portion of the implant and/or a wire-like proximal engagement member. In some embodiments, the first ring-shaped structure can be the distal-most ring-shaped structure of the implant and has a relatively smaller width than the second ring-shaped structure.

In some embodiments, the inner tubular member is slidable and rotatable with respect to the distal control member while the retainer is releasably coupled with the distal portion of the implant. The system can further include an elongate member coupled with the retainer and having a proximal end that is manipulatable by a user to permit release of the distal portion of the implant from the retainer. In some embodiments, the retainer is tubular and adapted to slide along the distal control member. The distal control member can include a recess adapted to receive the distal portion of the implant and the retainer can be movable to uncover the recess while the distal portion of the implant is received within the recess. In some embodiments the retainer includes a slot through which the implant can pass.

In some embodiments, the system includes an elongate anchor member. The elongate anchor member can include an anchor configured to contact a bladder wall. The anchor can be an inflatable balloon or multiple inflatable balloons. In some embodiments, the elongate anchor member includes a wire-form member having a portion configured to automatically deflect when deployed.

In some embodiments, the elongate grasper member includes a recess configured to releasably couple with the proximal portion of an implant. In some embodiments, the system is configured such that the proximal portion of the implant is free to release from the recess of the elongate grasper member when the recess is unconstrained by the first inner lumen.

In some embodiments, a proximal control device is included and coupled with a proximal end region of the delivery device. The proximal control device can be manipulatable by a user to control deployment of the implant from the delivery device. In some embodiments, the proximal control device includes a housing and is configured to distally advance the elongate grasper member with respect to the housing and the inner tubular member, and/or is configured to proximally retract and rotate the inner tubular member with respect to the housing and the distal control member, and/or is configured to proximally retract the outer tubular member with respect to the housing.

In many embodiments, a system for delivering an implantable device is provided, where the system includes: a delivery device including a first elongate member having an inner lumen, an elongate grasper member slidable within the inner lumen and configured to hold a proximal portion of an implant, and a distal control member configured to hold a distal portion of the implant; and a proximal control device coupled with a proximal end region of the delivery device, the proximal control device including a user actuator and a housing.

In many embodiments, a method of delivering an implant is provided that includes: advancing a delivery device within a body lumen of a patient, where the delivery device includes as first tubular member housing an implant, a distal control member slidable within the first tubular member and releasably coupled with a distal portion of the implant, and an elongate grasper member slidable within the first tubular member and releasably coupled with a proximal portion of the implant; causing relative motion between the elongate grasper member and the first tubular member to expose at least a portion of the implant from within the first tubular member; and releasing the distal portion of the implant from the distal control member and the proximal portion of the implant from the elongate grasper member.

In some embodiments, the body lumen is a prostatic urethra of a human. In some embodiments, upon release of the distal portion and the proximal portion, the implant is released from the delivery device in a state adapted to maintain the prostatic urethra in an at least partially open state.

In some embodiments, the implant has a body including first and second ring-shaped structures and an interconnect that extends between the first and second ring-shaped structures and causing relative motion can include distally advancing the elongate grasper member. In some embodiments, the method further includes rotating the first tubular member in a first direction with respect to the distal control member during exposure of the first ring-shaped structure from the first tubular member. In some embodiments, the method further includes rotating the first tubular member in a second direction with respect to the distal control member during exposure of the second ring-shaped structure from the first tubular member, the second direction being opposite the first direction. Rotation of the first tubular member in the first and second directions can occur while the distal control member is releasably coupled with the distal portion of the implant.

In some embodiments, the method further includes proximally retracting the first tubular member with respect to the elongate grasper member and the distal control member to expose the interconnect from the first tubular member. In some embodiments, the method further includes rotating the first tubular member while proximally retracting the first tubular member. In these embodiments, the interconnect can be curved.

In some embodiments, a retainer couples the distal portion of the implant to the distal control member, and the method includes releasing the retainer to release the distal portion of the implant from the distal control member.

In some embodiments, a control wire is coupled to the retainer at its distal end and proximally extends within the length of the control member. The control wire passes out of and back into an opening located near the distal end of the distal control member, forming a loop. The loop, which is located adjacent to and proximal of the retainer, prevents the retainer from moving in a proximal direction over the distal control member.

In some embodiments, the retainer is coupled to an elongate tubular member that extends proximally to the proximal control device. The proximal control device is adapted to proximally withdraw the elongate tubular member such that the retainer can be withdrawn or moved proximally, thereby releasing the distal portion of the implant from the distal control member.

In some embodiments, the method further includes exposing the proximal portion of the implant from within the first tubular member to release the proximal portion of the implant from the elongate grasper member.

In some embodiments, the method further includes anchoring the delivery device against a wall of a bladder before causing relative motion between the elongate grasper member and the first tubular member. In some embodiments, anchoring the delivery device includes inflating a balloon in the bladder.

In some embodiments, the first tubular member is an inner tubular member slidably received within an outer tubular member of the delivery device.

In many embodiments, a system for delivering an implant is described. The system includes an outer tubular member comprising an imaging device located in a distal end region of the outer tubular member; an inner tubular member within the outer tubular member, wherein the inner tubular member comprises a first elongate tubular member having a lumen that is adapted to house at least a portion of an implant, a second elongate tubular member having a lumen, and at least one support defining a plane that is generally perpendicular to a longitudinal axis of the inner tubular member; and one or more structures slidably advanceable within the lumen of the second elongate tubular member to cause deployment of the implant from within the inner tubular member.

In some embodiments, the system also includes a proximal control device coupled with the inner tubular member and the one or more structures, and releasably coupled with the outer tubular member with a coupling mechanism, wherein the proximal control device is configured to longitudinally move the inner tubular member and the outer tubular member concurrently.

In some embodiments, the system includes the implant, wherein the implant is configured to maintain a prostatic urethra in an at least partially open state. In some embodiments, the implant has a body comprising first and second ring-shaped structures and an interconnect that extends between the first and second ring-shaped structures.

In some embodiments, the one or more structures include an elongate grasper member configured to releasably couple with a proximal portion of the implant; and a distal control member configured to releasably couple with a distal portion of the implant. In some embodiments, the distal control member comprises a retainer configured to releasably couple with the distal portion of the implant, wherein the implant comprises a distal engagement member configured to releasably couple with the retainer. In some embodiments, the system also includes an elongate member coupled with the retainer and having a proximal end that is manipulatable by a user to permit release of the distal portion of the implant from the retainer. In some embodiments, the retainer is tubular and adapted to slide along the distal control member.

In some embodiments, the system also includes an elongate anchor member. In some embodiments, the elongate anchor member comprises an anchor configured to contact a bladder wall.

In some embodiments, the inner tubular member includes at least two supports. In some embodiments, each of the at least two supports are separated by about 3 to about 6 inches.

In some embodiments, the at least one support is fixed attached to the inner tubular member.

In some embodiments, the at least one support is fixedly attached to the first elongate tubular member.

In some embodiments, the second elongate tubular member is movable relative to the at least one support.

In some embodiments, the first elongate tubular member further comprises a lubricious liner.

In some embodiments, the first elongate tubular member is made from a hypotube, a braided material, or a polymer extrusion.

In some embodiments, the inner tubular member is made from a hypotube, a braided material, or a polymer extrusion.

In some embodiments, the at least one support is a laser-cut metal plate, a molded plastic component, or an extruded material.

In many embodiments, a method of imaging delivery of an implant is described. The method includes the steps of: advancing a delivery device within a urethra of a patient, wherein the delivery device comprises an outer tubular member comprising an imaging device located in a distal end region of the outer tubular member, an inner tubular member within the outer tubular member, wherein the inner tubular member comprises a first elongate tubular member having a lumen that is adapted to house at least a portion of an implant, a second elongate tubular member having a lumen, and at least one support defining a plane that is generally perpendicular to a longitudinal axis of the inner tubular member, and one or more structures slidably advanceable within the lumen of the second elongate tubular member to cause deployment of the implant from within the inner tubular member, wherein the outer tubular member, inner tubular member, and one or more structures are each coupled with a proximal control device outside of the patient; and longitudinally retracting the inner tubular member with respect to the proximal control device and the one or more structures to at least partially deploy the implant from the inner tubular member.

In some embodiments, the urethra is the prostatic urethra, and the method further includes the steps of, while the inner tubular member is being longitudinally retracted, concurrently (a) longitudinally retracting the outer tubular member with respect to the proximal control device and (b) imaging the at least partially deployed implant with an imaging device associated with a distal end region of the outer tubular member. In some embodiments, the outer tubular member is longitudinally retracted at the same rate as the inner tubular member. In some embodiments, the method further includes the steps of rotating the inner tubular member with respect to the proximal control device to at least partially deploy the implant from the inner tubular member; and while the inner tubular member is being rotated, concurrently (a) maintaining the outer tubular member in a rotationally fixed position with respect to the proximal control device and (b) imaging the at least partially deployed implant with the imaging device.

In some embodiments, the method further includes the step of releasing the implant from the delivery device.

In some embodiments, the method further includes the step of illuminating the implant with an illumination device at the distal end region of the outer tubular member.

In some embodiments, the inner tubular member includes at least two supports. In some embodiments, each of the at least two supports are separated by about 3 to about 6 inches.

In some embodiments, the at least one support is fixedly attached to the inner tubular member.

In some embodiments, the at least one support is fixedly attached to the first elongate tubular member.

In some embodiments, the second elongate tubular member is movable relative to the at least one support.

In some embodiments, the first elongate tubular member further comprises a lubricious liner.

In some embodiments, the first elongate tubular member is made from a hypotube, a braided material, or a polymer extrusion.

In some embodiments, the inner tubular member is made from a hypotube, a braided material, or a polymer extrusion.

In many embodiments, a system for delivering an implant, the system comprising a delivery device is described. The system may include an outer tubular member comprising an imaging device associated with a distal end region of the outer tubular member; an inner tubular member being within the outer tubular member, wherein the inner tubular member comprises a first elongate tubular member having a lumen that is adapted to house at least a portion of an implant and a second elongate tubular member having an opening in a distal end region communicating with a lumen; and one or more structures slidably advanceable within the lumen of the second elongate tubular member to cause deployment of the implant, the one or more structures comprising a retainer configured to releasably couple with a distal portion of the implant, wherein the retainer is coupled to an elongate member that extends proximally within the lumen of the second elongate tubular member, wherein the elongate member passes out of and back into the opening forming a loop that prevents the retainer from moving in a proximal direction.

In some embodiments, the system further includes a proximal control device coupled with the inner tubular member and the one or more structures, and releasably coupled with the outer tubular member with a coupling mechanism, wherein the proximal control device is configured to longitudinally move the inner tubular member and the outer tubular member concurrently.

In some embodiments, the imaging device is located in the distal end region of the outer tubular member.

In some embodiments, the one or more structures includes an elongate grasper member configured to releasably couple with a proximal portion of the implant; and a distal control member configured to releasably couple with a distal portion of the implant. In some embodiments, the elongate grasper member comprises a recess configured to releasably couple with the proximal portion of an implant. In some embodiments, the system is configured such that the proximal portion of the implant is free to release from the recess of the elongate grasper member when the recess is unconstrained by the first inner lumen.

In some embodiments, the retainer is configured to releasably couple with a distal portion of the implant, wherein the implant comprises a distal engagement member configured to releasably couple with the retainer. In some embodiments, the elongate member has a proximal end that is manipulatable by a user to permit release of the distal portion of the implant from the retainer. In some embodiments, the distal control member comprises a recess adapted to receive the distal portion of the implant. In some embodiments, the retainer is movable to uncover the recess while the distal portion of the implant is received within the recess. In some embodiments, the retainer comprises a slot.

In some embodiments, the implant comprises a proximal engagement member configured to releasably couple with the elongate grasper member. In some embodiments, the proximal control device is configured to rotate and longitudinally move the inner tubular member with respect to the distal control member while the distal control member is releasably coupled with the distal portion of the implant. In some embodiments, the proximal control device is configured to rotate the inner tubular member without rotating the outer tubular member. In some embodiments, the retainer is tubular and adapted to slide along the distal control member.

In some embodiments, the elongate member has a proximal end that is manipulatable by a user to pull the loop into the lumen of the second elongate tubular member and permit release of the distal portion of the implant from the retainer.

In some embodiments, the elongate member is made from a material selected from the group consisting of nitinol, Kevlar, stainless steel, suture, and liquid crystal polymer. In some embodiments, the elongate member is made from a tensionable material.

In many embodiments, a method of imaging delivery of an implant is described. The method includes the steps of: advancing a delivery device within a urethra of a patient, wherein the delivery device comprises an outer tubular member comprising an imaging device associated with a distal end region of the outer tubular member, an inner tubular member within the outer tubular member, wherein the inner tubular member comprises a first elongate tubular member having a lumen that is adapted to house at least a portion of an implant and a second elongate tubular member an opening in a distal end region communicating with a lumen, and one or more structures slidably advanceable within the lumen of the second elongate tubular member to cause deployment of the implant, the one or more structures comprising a retainer configured to releasably couple with a distal portion of an implant, wherein the retainer is coupled to an elongate member that extends proximally within the lumen of the second elongate tubular member, wherein the elongate member passes out of and back into the opening forming a loop that prevents the retainer from moving in a proximal direction, wherein the outer tubular member, inner tubular member, and one or more structures are each coupled with a proximal control device outside of the patient; longitudinally retracting the inner tubular member with respect to the proximal control device and the one or more structures to at least partially deploy the implant from the inner tubular member; and releasing the implant from the delivery device by pulling the elongate member in a proximal direction, wherein the loop is withdrawn into the lumen of the second elongate tubular member and the retainer is moved in a proximal direction.

In some embodiments, the urethra is the prostatic urethra, and the method further includes the step of, while the inner tubular member is being longitudinally retracted, concurrently (a) longitudinally retracting the outer tubular member with respect to the proximal control device and (b) imaging the at least partially deployed implant with an imaging device associated with a distal end region of the outer tubular member. In some embodiments, the outer tubular member is longitudinally retracted at the same rate as the inner tubular member. In some embodiments, the method further includes the steps of rotating the inner tubular member with respect to the proximal control device to at least partially deploy the implant from the inner tubular member; and while the inner tubular member is being rotated, concurrently (a) maintaining the outer tubular member in a rotationally fixed position with respect to the proximal control device and (b) imaging the at least partially deployed implant with the imaging device.

In some embodiments, the imaging device is located in the distal end region of the outer tubular member.

In some embodiments, the method further includes the step of illuminating the implant with an illumination device at the distal end region of the outer tubular member.

In some embodiments, the retainer is tubular and adapted to slide along the second elongate tubular member.

In some embodiments, the second elongate tubular member comprises a recess adapted to receive a distal portion of the implant.

In some embodiments, the retainer is movable to uncover the recess while the distal portion of the implant is received within the recess.

In some embodiments, the retainer comprises a slot.

In many embodiments, a system for delivering an implant is described. The system includes an outer tubular member comprising first and second lumens and a distal end; an imaging module mounted to at least one elongate member that extends through the second lumen, wherein the imaging module is configured to be positioned distal of the distal end of the outer tubular member upon distal advancement of the at least one elongate member; and an inner tubular member being within the first lumen of outer tubular member, wherein the inner tubular member is adapted to house at least a portion of an implant.

In some embodiments, the system further includes one or more structures slidably advanceable within the inner tubular member to cause deployment of the implant from within the inner tubular member; and a proximal control device coupled with the inner tubular member and the one or more structures, and releasably coupled with the outer tubular member with a coupling mechanism, wherein the proximal control device is configured to longitudinally move the inner tubular member and the outer tubular member concurrently. In some embodiments, the one or more structures comprise an elongate grasper member configured to releasably couple with a proximal portion of the implant; and a distal control member configured to releasably couple with a distal portion of the implant. In some embodiments, the distal control member comprises a retainer configured to releasably couple with the distal portion of the implant, wherein the implant comprises a distal engagement member configured to releasably couple with the retainer. In some embodiments, the implant comprises a proximal engagement member configured to releasably couple with the elongate grasper member.

In some embodiments, the implant is configured to maintain a prostatic urethra in an at least partially open state. In some embodiments, the implant has a body comprising first and second ring-shaped structures and an interconnect that extends between the first and second ring-shaped structures.

In some embodiments, the distal end region of the outer tubular member further comprises an illumination device.

In some embodiments, the imaging module comprises a camera and a light source. In some embodiments, the light source is at least one LED.

In some embodiments, the imaging module is mounted to at least two elongate members.

In some embodiments, the imaging module is mounted to at least three elongate members.

In some embodiments, the imaging module is configured to be positioned between about 0 cm to about 5 cm distal of the distal end of the outer tubular member.

In many embodiments, a method of imaging delivery of an implant is described. The method includes the steps of: advancing a delivery device within a urethra of a patient, wherein the delivery device comprises an outer tubular member comprising first and second lumens and a distal end, an imaging module mounted to at least one elongate member extending through the second lumen, an inner tubular member extending through the first lumen and housing at least a portion of an implant, and one or more structures slidably advanceable within the inner tubular member to cause deployment of the implant from within the inner tubular member, wherein the outer tubular member, inner tubular member, and one or more structures are each coupled with a proximal control device outside of the patient; longitudinally retracting the inner tubular member with respect to the proximal control device and the one or more structures to at least partially deploy the implant from the inner tubular member; extending the imaging module distally beyond the distal end of the outer tubular member; and imaging the at least partially deployed implant.

In some embodiments, the urethra is the prostatic urethra.

In some embodiments, the method further includes the step of releasing the implant from the delivery device.

In some embodiments, the outer tubular member is longitudinally retracted at the same rate as the inner tubular member.

In some embodiments, the method further includes the steps of rotating the inner tubular member with respect to the proximal control device to at least partially deploy the implant from the inner tubular member; and while the inner tubular member is being rotated, concurrently (a) maintaining the outer tubular member in a rotationally fixed position with respect to the proximal control device and (b) imaging the at least partially deployed implant with the imaging device.

In some embodiments, the implant has a body comprising first and second ring-shaped structures and an interconnect that extends between the first and second ring-shaped structures, wherein the second ring-shaped structure is proximal the first ring-shaped structure.

In some embodiments, the imaging module can visualize placement of the second ring-shaped structure after being extended distal of the distal end of the outer tubular member. In some embodiments, the method further includes the step of releasing the implant from the delivery device after imaging.

In some embodiments, the imaging module is extended between about 0 cm to about 5 cm distally the distal end of the outer tubular member.

In many embodiments, a system for delivering an implant is described. The system includes an outer tubular member; an inner tubular member being within the outer tubular member, wherein the inner tubular member is adapted to house at least a portion of an implant; one or more structures slidably advanceable within the inner tubular member to cause deployment of the implant from within the inner tubular member; a proximal control device comprising a rotary adapter, the proximal control device coupled with the inner tubular member and the one or more structures, and releasably coupled with the outer tubular member with a coupling mechanism; and an imaging device coupled to the rotary adapter, wherein the proximal control device is configured to longitudinally move the inner tubular member and the outer tubular member concurrently.

In some embodiments, the system further includes an implant. In some embodiments, the implant has a body comprising first and second ring-shaped structures and an interconnect that extends between the first and second ring-shaped structures. In some embodiments, the one or more structures comprise: an elongate grasper member configured to releasably couple with a proximal portion of the implant; and a distal control member configured to releasably couple with a distal portion of the implant. In some embodiments, the distal control member comprises a retainer configured to releasably couple with the distal portion of the implant, wherein the implant comprises a distal engagement member configured to releasably couple with the retainer. In some embodiments, the implant comprises a proximal engagement member configured to releasably couple with the elongate grasper member. In some embodiments, the proximal control device is configured to rotate and longitudinally move the inner tubular member with respect to the distal control member while the distal control member is releasably coupled with the distal portion of the implant. In some embodiments, the proximal control device is configured to rotate the inner tubular member without rotating the outer tubular member. In some embodiments, the system further includes an elongate member coupled with the retainer and having a proximal end that is manipulatable by a user to permit release of the distal portion of the implant from the retainer. In some embodiments, the retainer is tubular and adapted to slide along the distal control member. In some embodiments, the distal control member comprises a recess adapted to receive the distal portion of the implant. In some embodiments, the retainer is movable to uncover the recess while the distal portion of the implant is received within the recess.

In some embodiments, the distal end region of the outer tubular member further comprises an illumination device.

In some embodiments, a distal end region of the inner tubular member is distal to the distal end region of the outer tubular member by a separation distance, and wherein the proximal control device is configured to longitudinally move the outer tubular member and inner tubular member concurrently without changing the separation distance.

In some embodiments, a proximal end of the inner tubular member is coupled with the rotary adapter.

In some embodiments, the rotary adapter comprises a distal component, a sliding component, a spring and a proximal component, and wherein the imaging device is coupled to the sliding component. In some embodiments, the sliding component comprises an annular groove and wherein the imaging device is coupled to the annular groove. In some embodiments, the spring is located between the distal component and the sliding component. In some embodiments, the spring is located between the sliding component and the proximal component. In some embodiments, the sliding component includes an electrical plate or ring that conducts electricity.

In some embodiments, the rotary adapter conducts electricity.

In some embodiments, the rotary adapter further comprises an electrical plate or ring that conducts electricity.

In some embodiments, the rotary adapter is electrically connected to a light source. In some embodiments, the light source is mounted on a distal end of the inner tubular member or a distal end of the one or more structures slidably advanceable within the inner tubular member.

In some embodiments, the rotary adapter is electrically connected to the imaging device.

In some embodiments, the imaging device is capable of longitudinally advancing with respect to a distal end of the inner tubular member.

In some embodiments, the imaging device is capable of longitudinally retracting with respect to a distal end of the inner tubular member.

In many embodiments, a method of imaging delivery of an implant is described. The method includes the steps of: advancing a delivery device within a urethra of a patient, wherein the delivery device comprises an outer tubular member, an inner tubular member within the outer tubular member and housing at least a portion of an implant, one or more structures slidably advanceable within the inner tubular member to cause deployment of the implant from within the inner tubular member, and an imaging device, wherein the outer tubular member, inner tubular member, one or more structures, and imaging device are each coupled with a proximal control device outside of the patient, and wherein the proximal control device comprises a rotary adapter that is coupled to the imaging device; longitudinally retracting the inner tubular member with respect to the proximal control device and the one or more structures to at least partially deploy the implant from the inner tubular member; longitudinally moving the imaging device with respect to a distal end of the inner tubular member; and imaging the at least partially deployed implant with the imaging device.

In some embodiments, the urethra is the prostatic urethra.

In some embodiments, the method further includes the step of releasing the implant from the delivery device.

In some embodiments, the outer tubular member is longitudinally retracted at the same rate as the inner tubular member.

In some embodiments, the method further includes the steps of rotating the inner tubular member with respect to the proximal control device to at least partially deploy the implant from the inner tubular member; and while the inner tubular member is being rotated, concurrently (a) maintaining the outer tubular member in a rotationally fixed position with respect to the proximal control device and (b) imaging the at least partially deployed implant with the imaging device.

In some embodiments, the method further includes the step of illuminating the implant with an illumination device at the distal end region of the outer tubular member.

In some embodiments, the implant has a body comprising first and second ring-shaped structures and an interconnect that extends between the first and second ring-shaped structures, wherein the second ring-shaped structure is proximal the first ring-shaped structure. In some embodiments, the imaging device can visualize placement of the second ring-shaped structure after partial deployment. In some embodiments, the imaging device is proximally withdrawn with respect to the second ring-shaped structure after partial deployment of the implant. In some embodiments, the imaging device is distally advanced with respect to the second ring-shaped structure after partial deployment of the implant. In some embodiments, the imaging device is longitudinally advanced with respect to the distal end of the inner tubular member. In some embodiments, the imaging device is longitudinally retracted with respect to the distal end of the inner tubular member.

In some embodiments, the method further includes the step of releasing the implant from the delivery device after imaging.

In many embodiments, a system for delivering an implant is described. The system includes an outer tubular member; an inner tubular member being within the outer tubular member, wherein the inner tubular member is adapted to house at least a portion of an implant; one or more structures slidably advanceable within a lumen of the inner tubular member to cause deployment of the implant from within the inner tubular member; and a proximal control device coupled with the inner tubular member and the one or more structures, and releasably coupled with the outer tubular member through a coupling mechanism, wherein the proximal control device comprises a pull wire and an actuator, the actuator comprising a rotatable wheel, an extension, a latch, and a ledge, wherein the pull wire extends through at least a portion of the outer tubular member, wherein the rotatable wheel is adapted to wind and unwind the pull wire and is located within a housing, wherein the extension has first and second sides and extends from the housing, and wherein the latch is housed within the extension and is slidable from the first side to the second side of the extension, and wherein the ledge is disposed on the housing and is adapted to frictionally engage the latch.

In some embodiments, winding the pull wire around the rotatable wheel results in deflection of the outer tubular member.

In some embodiments, unwinding the pull wire from the rotatable wheel results in straightening of the outer tubular member.

In some embodiments, the extension is movable from a first position to a second position by rotating at least a portion of the housing. In some embodiments, when the extension is in the first position, the rotatable wheel is capable of winding or unwinding the pull wire. In some embodiments, in the first position, the extension is angled away from a distal end of the outer tubular member. In some embodiments, when the extension is in the second position, the rotatable wheel is not capable of winding or unwinding the pull wire. In some embodiments, the latch is frictionally engaged by the ledge when the extension is in the second position. In some embodiments, in the second position, the extension is angled towards a distal end of the outer tubular member.

In some embodiments, the extension further comprises a paddle terminating in a detent. In some embodiments, the latch is slidable along the paddle.

In some embodiments, the ledge is located on a right-hand side of the housing.

In some embodiments, the extension is attached to a left-hand side of the housing.

In some embodiments, the pull wire extends through a lumen of the outer tubular member.

In some embodiments, the pull wire is coupled to or embedded in a sidewall of the outer tubular member.

In some embodiments, a distal end of the pull wire is secured to the outer tubular member in a distal end region of the outer tubular member.

In many embodiments, a method of delivering of an implant is described. The method includes the steps of: (a) advancing a delivery device within a urethra of a patient, wherein the delivery device comprises an outer tubular member, an inner tubular member being within the outer tubular member, wherein the inner tubular member is adapted to house at least a portion of an implant, one or more structures slidably advanceable within a lumen of the inner tubular member to cause deployment of the implant from within the inner tubular member; and a proximal control device coupled with the inner tubular member and the one or more structures, and releasably coupled with the outer tubular member through a coupling mechanism, wherein the proximal control device comprises a pull wire and an actuator, the actuator comprising a rotatable wheel, an extension, a latch, and a ledge, wherein the pull wire extends through at least a portion of the outer tubular member, wherein the rotatable wheel is adapted to wind and unwind the pull wire and is located within a housing, wherein the extension has first and second sides and extends from the housing, and wherein the latch is housed within the extension and is slidable from the first side to the second side of the extension, and wherein the ledge is disposed on the housing and is adapted to frictionally engage the latch; (b) longitudinally retracting the inner tubular member with respect to the proximal control device and the one or more structures to at least partially deploy the implant from the inner tubular member; and (c) releasing the implant from the delivery device, wherein the outer tubular member is deflected by winding the pull wire around the rotatable wheel during at least one of steps (a), (b), or (c) or between steps (a) and (b) or (b) and (c), and wherein the outer tubular member is locked in a deflected position by frictionally engaging the latch with the ledge after the outer tubular member is deflected.

In some embodiments, the outer tubular member is deflected and locked in the deflected position during the advancing step (a).

In some embodiments, the outer tubular member is deflected and locked in the deflected position between steps (a) and (b).

In some embodiments, the outer tubular member is deflected and locked in the deflected position during the retracting step (b).

In some embodiments, the outer tubular member is deflected and locked in the deflected position between steps (b) and (c).

In some embodiments, the outer tubular member is deflected and locked in the deflected position during the releasing step (c).

In some embodiments, the extension is movable from a first position to a second position by rotating at least a portion of the housing. In some embodiments, when the extension is in the first position, the rotatable wheel is unlocked and capable of winding or unwinding the pull wire. In some embodiments, when the extension is in the second position, the rotatable wheel is locked and not capable of winding or unwinding the pull wire. In some embodiments, the latch is frictionally engaged by the ledge when the extension is in the second position. In some embodiments, the method further includes the step of unlocking the outer tubular member from the deflected position by disengaging the latch from the ledge, wherein the extension returns to the first position.

In some embodiments, the pull wire extends through a lumen of the outer tubular member.

In some embodiments, the pull wire is coupled to or embedded in a sidewall of the outer tubular member.

In some embodiments, a distal end of the pull wire is secured to the outer tubular member in a distal end region of the outer tubular member.

In many embodiments, a system for delivering an implant is described. The system includes an outer tubular member comprising an imaging device associated with a distal end region of the outer tubular member; an inner tubular member being within the outer tubular member, wherein the inner tubular member comprises a first elongate tubular member having a lumen that is adapted to house at least a portion of an implant and a second elongate tubular member having an opening in a distal end region communicating with a lumen; and one or more structures slidably advanceable within the lumen of the second elongate tubular member to cause deployment of the implant, the one or more structures comprising a retainer configured to releasably couple with a distal portion of the implant, wherein the retainer is coupled to a third elongate tubular member that extends proximally to a proximal control device.

In some embodiments, the proximal control device is adapted to proximally withdraw the third elongate tubular member.

In some embodiments, the retainer is configured to releasably couple with a distal portion of the implant, wherein the implant comprises a distal engagement member configured to releasably couple with the retainer.

In some embodiments, the proximal control device is coupled with the inner tubular member and the one or more structures, and releasably coupled with the outer tubular member through a coupling mechanism, wherein the proximal control device is configured to longitudinally move the inner tubular member and the outer tubular member concurrently.

In some embodiments, the one or more structures include an elongate grasper member configured to releasably couple with a proximal portion of the implant; and a distal control member configured to releasably couple with a distal portion of the implant.

In some embodiments, the elongate member has a proximal end that is manipulatable by a user to permit release of the distal portion of the implant from the retainer.

In many embodiments, a method of delivering an implant is described. The method includes the steps of: advancing a delivery device within a urethra of a patient, wherein the delivery device comprises an outer tubular member comprising an imaging device associated with a distal end region of the outer tubular member, an inner tubular member being within the outer tubular member, wherein the inner tubular member comprises a first elongate tubular member having a lumen that is adapted to house at least a portion of an implant and a second elongate tubular member having an opening in a distal end region communicating with a lumen; and one or more structures slidably advanceable within the lumen of the second elongate tubular member to cause deployment of the implant, the one or more structures comprising a retainer configured to releasably couple with a distal portion of the implant, wherein the retainer is coupled to a third elongate tubular member that extends proximally to a proximal control device; longitudinally retracting the inner tubular member with respect to the proximal control device and the one or more structures to at least partially deploy the implant from the inner tubular member; and releasing the implant from the delivery device by withdrawing the third elongate tubular member in a proximal direction, wherein the retainer is moved in a proximal direction.

In some embodiments, the retainer is adapted to slide along the second elongate tubular member.

In some embodiments, the second elongate tubular member comprises a recess adapted to receive a distal portion of the implant.

In some embodiments, the retainer is movable to uncover the recess while the distal portion of the implant is received within the recess.

In many embodiments, a system for delivering an implant is described. The system includes an outer tubular member; an inner tubular member being within the outer tubular member, wherein the inner tubular member is adapted to house at least a portion of an implant; one or more structures slidably advanceable within the inner tubular member to cause deployment of the implant from within the inner tubular member; and a proximal control device coupled with the inner tubular member and the one or more structures, and releasably coupled with the outer tubular member through a coupling mechanism, wherein the proximal control device is configured to longitudinally move the inner tubular member and the outer tubular member concurrently, wherein the proximal control device comprises a movable handle portion that is movable with respect to a proximal handle portion, and wherein the movable handle portion comprises a groove that is configured to receive a detent coupled to an inside surface of the proximal handle portion.

In some embodiments, the detent is located on the inside surface of a distal section of the proximal handle portion.

In some embodiments, the detent is deflectable.

In some embodiments, the proximal handle portion further comprises a stent having a first end and a second end, wherein the first end of the stent is attached to the inside surface of the proximal handle portion, and wherein the stent terminates in the detent at the second end.

In some embodiments, the proximal handle portion is rotatable around the movable handle portion.

In some embodiments, rotation of the proximal handle can dislodge the detent from the groove.

In some embodiments, the system further includes an implant.

In many embodiments, a method of delivering an implant is described. The method includes the steps of: advancing a delivery device within a urethra of a patient, wherein the delivery device comprises an outer tubular member, an inner tubular member being within the outer tubular member, wherein the inner tubular member is adapted to house at least a portion of an implant; one or more structures slidably advanceable within the inner tubular member to cause deployment of the implant from within the inner tubular member; and a proximal control device coupled with the inner tubular member and the one or more structures, and releasably coupled with the outer tubular member through a coupling mechanism, wherein the proximal control device is configured to longitudinally move the inner tubular member and the outer tubular member concurrently, wherein a mechanism in the proximal control device prevents the outer tubular member from rotating with respect to the inner tubular member; longitudinally retracting the inner tubular member with respect to the proximal control device and the one or more structures to at least partially deploy the implant from the inner tubular member; and releasing the implant from the delivery device.

In some embodiments, the proximal control device comprises a movable handle portion that is movable with respect to a proximal handle portion, and wherein the mechanism comprises a groove on the movable handle portion that is configured to receive a detent coupled to an inside surface of the proximal handle portion. In some embodiments, the detent is deflectable. In some embodiments, the detent is located on the inside surface of a distal section of the proximal handle portion. In some embodiments, the proximal handle portion further comprises a stent having a first end and a second end, wherein the first end of the stent is attached to the inside surface of the proximal handle portion, and wherein the stent terminates in the detent at the second end. In some embodiments, the proximal handle portion is rotatable around the movable handle portion. In some embodiments, rotation of the proximal handle can dislodge the detent from the groove. In some embodiments, the method further includes the step of releasing the mechanism to allow the outer tubular member to rotate with respect to the inner tubular member. In some embodiments, releasing the mechanism includes removing the detent from the groove. In some embodiments, the detent is removed from the groove by rotation of the proximal handle portion around the movable handle portion.

In many embodiments, a system for delivering an implant is provided, where the system includes a delivery device including: an outer tubular member including an imaging device located in a distal end region of the outer tubular member; an inner tubular member being within the outer tubular member, where the inner tubular member is adapted to house at least a portion of an implant; one or more structures slidably advanceable within the inner tubular member to cause deployment of the implant from within the inner tubular member; and a proximal control device coupled with the inner tubular member and the one or more structures, and releasably coupled with the outer tubular member with a coupling mechanism, where the proximal control device is configured to longitudinally move the inner tubular member and the outer tubular member concurrently.

In some embodiments, the inner tubular member includes a first elongate tubular member having a lumen that is adapted to house at least a portion of an implant, a second elongate tubular member having a lumen, and at least one support defining a plane that is generally perpendicular to a longitudinal axis of the inner tubular member. The inner tubular member may contain two, alternatively three, alternatively four, alternatively five, alternatively six, alternatively seven, alternatively eight or more supports. The supports may be fixedly attached to the inner tubular member. The supports may also be fixedly attached to the first elongate tubular member. The second elongate tubular member may be movable with respect to the supports. The supports may be separated by about 3 to about 6 inches.

In some embodiments, the system further includes the implant. The implant can be configured to maintain a prostatic urethra in an at least partially open state. In some embodiments, the implant has a body including first and second ring-shaped structures and an interconnect that extends between the first and second ring-shaped structures.

In some embodiments, the one or more structures include: an elongate grasper member configured to releasably couple with a proximal portion of the implant; and a distal control member configured to releasably couple with a distal portion of the implant. In some embodiments, the distal control member includes a retainer configured to releasably couple with the distal portion of the implant, where the implant includes a distal engagement member configured to releasably couple with the retainer. In some embodiments, the implant includes a proximal engagement member configured to releasably couple with the elongate grasper member. In some embodiments, the implant includes a wire-like distal engagement member that extends proximally away from a distal-most portion of the implant. In some embodiments, the implant includes a wire-like proximal engagement member.

In some embodiments, the proximal control device is configured to rotate and longitudinally move the inner tubular member with respect to the distal control member while the distal control member is releasably coupled with the distal portion of the implant. In some embodiments, the proximal control device is configured to rotate the inner tubular member without rotating the outer tubular member.

In some embodiments, the system may include an anti-rotation mechanism that prevents the outer tubular member from rotating. The system may include a delivery device comprising an outer tubular member; an inner tubular member being within the outer tubular member, wherein the inner tubular member is adapted to house at least a portion of an implant; one or more structures slidably advanceable within the inner tubular member to cause deployment of the implant from within the inner tubular member; and a proximal control device coupled with the inner tubular member and the one or more structures, and releasably coupled with the outer tubular member through a coupling mechanism, wherein the proximal control device is configured to longitudinally move the inner tubular member and the outer tubular member concurrently, wherein the proximal control device comprises a movable handle portion that is movable with respect to a proximal handle portion, and wherein the movable handle portion comprises a groove that is configured to receive a detent coupled to an inside surface of the proximal handle portion. The proximal handle portion may further include a stent having a first end and a second end, wherein the first end of the stent is attached to the inside surface of the proximal handle portion, and wherein the stent terminates in the detent at the second end. The detent is deflectable. The proximal handle portion is rotatable around the movable handle portion and additional rotational force applied to the proximal handle portion or movable handle portion can dislodge the detent from the groove.

In some embodiments, the method includes advancing a delivery device within a urethra of a patient, wherein the delivery device comprises an outer tubular member, an inner tubular member being within the outer tubular member, wherein the inner tubular member is adapted to house at least a portion of an implant; one or more structures slidably advanceable within the inner tubular member to cause deployment of the implant from within the inner tubular member; and a proximal control device coupled with the inner tubular member and the one or more structures, and releasably coupled with the outer tubular member through a coupling mechanism, wherein the proximal control device is configured to longitudinally move the inner tubular member and the outer tubular member concurrently, wherein a mechanism in the proximal control device prevents the outer tubular member from rotating with respect to the inner tubular member; longitudinally retracting the inner tubular member with respect to the proximal control device and the one or more structures to at least partially deploy the implant from the inner tubular member; and releasing the implant from the delivery device. The proximal control device includes a movable handle portion that is movable with respect to a proximal handle portion, and wherein the mechanism comprises a groove on the movable handle portion that is configured to receive a detent coupled to an inside surface of the proximal handle portion. The proximal handle portion may further include a stent having a first end and a second end, wherein the first end of the stent is attached to the inside surface of the proximal handle portion, and wherein the stent terminates in the detent at the second end. The detent is deflectable. The proximal handle portion is rotatable around the movable handle portion and rotation of the proximal handle can dislodge the detent from the groove. The method may further include the step of releasing the mechanism to allow the outer tubular member to rotate with respect to the inner tubular member. Releasing the mechanism includes removing the detent from the groove by rotating the proximal handle portion or the movable handle portion around the other of the movable handle portion and proximal handle portion.

In some embodiments, the system further includes a steering lock. The system includes a delivery device comprising an outer tubular member; an inner tubular member being within the outer tubular member, wherein the inner tubular member is adapted to house at least a portion of an implant; one or more structures slidably advanceable within a lumen of the inner tubular member to cause deployment of the implant from within the inner tubular member; and a proximal control device coupled with the inner tubular member and the one or more structures, and releasably coupled with the outer tubular member with a coupling mechanism, wherein the proximal control device comprises a pull wire and an actuator, the actuator comprising a rotatable wheel, an extension, a latch, and a ledge, wherein the pull wire extends through at least a portion of the outer tubular member, wherein the rotatable wheel is adapted to wind and unwind the pull wire and is located within a housing, wherein the extension has first and second sides and extends from the housing, and wherein the latch is housed within the extension and is slidable from the first side to the second side of the extension, and wherein the ledge is disposed on the housing and is adapted to frictionally engage the latch. Winding of the pull wire around the rotatable wheel results in deflection of the outer tubular member and unwinding of the pull wire from the rotatable wheel results in straightening of the outer tubular member. The extension is movable from a first position to a second position by rotating at least a portion of the housing. When the extension is in the first position, the rotatable wheel is capable of winding or unwinding the pull wire. When the extension is in the second position, the rotatable wheel is not capable of winding or unwinding the pull wire. In the first position, the extension is angled away from a distal end of the outer tubular member. In the second position, the extension is angled towards a distal end of the outer tubular member and the latch is frictionally engaged by the ledge when the extension is in the second position.

In some embodiments, the method includes steering and locking the outer tubular member during delivery of the implant. The method includes the steps of (a) advancing a delivery device within a urethra of a patient, wherein the delivery device comprises an outer tubular member, an inner tubular member being within the outer tubular member, wherein the inner tubular member is adapted to house at least a portion of an implant, one or more structures slidably advanceable within a lumen of the inner tubular member to cause deployment of the implant from within the inner tubular member; and a proximal control device coupled with the inner tubular member and the one or more structures, and releasably coupled with the outer tubular member through a coupling mechanism, wherein the proximal control device comprises a pull wire and an actuator, the actuator comprising a rotatable wheel, an extension, a latch, and a ledge, wherein the pull wire extends through at least a portion of the outer tubular member, wherein the rotatable wheel is adapted to wind and unwind the pull wire and is located within a housing, wherein the extension has first and second sides and extends from the housing, and wherein the latch is housed within the extension and is slidable from the first side to the second side of the extension, and wherein the ledge is disposed on the housing and is adapted to frictionally engage the latch; (b) longitudinally retracting the inner tubular member with respect to the proximal control device and the one or more structures to at least partially deploy the implant from the inner tubular member; and (c) releasing the implant from the delivery device, wherein the outer tubular member is deflected by winding the pull wire around the rotatable wheel during at least one of steps (a), (b), or (c) or between steps (a) and (b) or (b) and (c), and wherein the outer tubular member is locked in a deflected position by frictionally engaging the latch with the ledge after the outer tubular member is deflected. Winding of the pull wire around the rotatable wheel results in deflection of the outer tubular member and unwinding of the pull wire from the rotatable wheel results in straightening of the outer tubular member. The extension is movable from a first position to a second position by rotating at least a portion of the housing. When the extension is in the first position, the rotatable wheel is capable of winding or unwinding the pull wire. When the extension is in the second position, the rotatable wheel is not capable of winding or unwinding the pull wire. In the first position, the extension is angled away from a distal end of the outer tubular member. In the second position, the extension is angled towards a distal end of the outer tubular member and the latch is frictionally engaged by the ledge when the extension is in the second position. The method may further include the step of unlocking the outer tubular member from the deflected position by disengaging the latch from the ledge, wherein the extension returns to the first position.

In some embodiments, the method includes steering and locking the outer tubular member during delivery of the implant during or after advancement of the delivery device. The method includes the steps of (a) advancing a delivery device within a urethra of a patient, wherein the delivery device comprises an outer tubular member, an inner tubular member being within the outer tubular member, wherein the inner tubular member is adapted to house at least a portion of an implant, one or more structures slidably advanceable within a lumen of the inner tubular member to cause deployment of the implant from within the inner tubular member; and a proximal control device coupled with the inner tubular member and the one or more structures, and releasably coupled with the outer tubular member through a coupling mechanism, wherein the proximal control device comprises a pull wire and an actuator, the actuator comprising a rotatable wheel, an extension, a latch, and a ledge, wherein the pull wire extends through at least a portion of the outer tubular member, wherein the rotatable wheel is adapted to wind and unwind the pull wire and is located within a housing, wherein the extension has first and second sides and extends from the housing, and wherein the latch is housed within the extension and is slidable from the first side to the second side of the extension, and wherein the ledge is disposed on the housing and is adapted to frictionally engage the latch; (b) longitudinally retracting the inner tubular member with respect to the proximal control device and the one or more structures to at least partially deploy the implant from the inner tubular member; and (c) releasing the implant from the delivery device, wherein the outer tubular member is deflected by winding the pull wire around the rotatable wheel during or after the advancing step (a), e.g., before retracting the inner tubular member, and wherein the outer tubular member is locked in a deflected position by frictionally engaging the latch with the ledge after the outer tubular member is deflected. Winding of the pull wire around the rotatable wheel results in deflection of the outer tubular member and unwinding of the pull wire from the rotatable wheel results in straightening of the outer tubular member. The extension is movable from a first position to a second position by rotating at least a portion of the housing. When the extension is in the first position, the rotatable wheel is capable of winding or unwinding the pull wire. When the extension is in the second position, the rotatable wheel is not capable of winding or unwinding the pull wire. In the first position, the extension is angled away from a distal end of the outer tubular member. In the second position, the extension is angled towards a distal end of the outer tubular member and the latch is frictionally engaged by the ledge when the extension is in the second position. The method may further include the step of unlocking the outer tubular member from the deflected position by disengaging the latch from the ledge, wherein the extension returns to the first position.

In some embodiments, the method includes steering and locking the outer tubular member during delivery of the implant during or after partially deploying the implant. The method includes the steps of (a) advancing a delivery device within a urethra of a patient, wherein the delivery device comprises an outer tubular member, an inner tubular member being within the outer tubular member, wherein the inner tubular member is adapted to house at least a portion of an implant, one or more structures slidably advanceable within a lumen of the inner tubular member to cause deployment of the implant from within the inner tubular member; and a proximal control device coupled with the inner tubular member and the one or more structures, and releasably coupled with the outer tubular member with a coupling mechanism, wherein the proximal control device comprises a pull wire and an actuator, the actuator comprising a rotatable wheel, an extension, a latch, and a ledge, wherein the pull wire extends through at least a portion of the outer tubular member, wherein the rotatable wheel is adapted to wind and unwind the pull wire and is located within a housing, wherein the extension has first and second sides and extends from the housing, and wherein the latch is housed within the extension and is slidable from the first side to the second side of the extension, and wherein the ledge is disposed on the housing and is adapted to frictionally engage the latch; (b) longitudinally retracting the inner tubular member with respect to the proximal control device and the one or more structures to at least partially deploy the implant from the inner tubular member; and (c) releasing the implant from the delivery device, wherein the outer tubular member is deflected by winding the pull wire around the rotatable wheel during or after retracting the inner tubular member and the one or more structures to at least partially deploy the implant in step (b), e.g., before releasing the implant, and wherein the outer tubular member is locked in a deflected position by frictionally engaging the latch with the ledge after the outer tubular member is deflected. Winding of the pull wire around the rotatable wheel results in deflection of the outer tubular member and unwinding of the pull wire from the rotatable wheel results in straightening of the outer tubular member. The extension is movable from a first position to a second position by rotating at least a portion of the housing. When the extension is in the first position, the rotatable wheel is capable of winding or unwinding the pull wire. When the extension is in the second position, the rotatable wheel is not capable of winding or unwinding the pull wire. In the first position, the extension is angled away from a distal end of the outer tubular member. In the second position, the extension is angled towards a distal end of the outer tubular member and the latch is frictionally engaged by the ledge when the extension is in the second position. The method may further include the step of unlocking the outer tubular member from the deflected position by disengaging the latch from the ledge, wherein the extension returns to the first position.

In some embodiments, the method includes steering and locking the outer tubular member during release of the implant. The method includes the steps of (a) advancing a delivery device within a urethra of a patient, wherein the delivery device comprises an outer tubular member, an inner tubular member being within the outer tubular member, wherein the inner tubular member is adapted to house at least a portion of an implant, one or more structures slidably advanceable within a lumen of the inner tubular member to cause deployment of the implant from within the inner tubular member; and a proximal control device coupled with the inner tubular member and the one or more structures, and releasably coupled with the outer tubular member with a coupling mechanism, wherein the proximal control device comprises a pull wire and an actuator, the actuator comprising a rotatable wheel, an extension, a latch, and a ledge, wherein the pull wire extends through at least a portion of the outer tubular member, wherein the rotatable wheel is adapted to wind and unwind the pull wire and is located within a housing, wherein the extension has first and second sides and extends from the housing, and wherein the latch is housed within the extension and is slidable from the first side to the second side of the extension, and wherein the ledge is disposed on the housing and is adapted to frictionally engage the latch; (b) longitudinally retracting the outer tubular member with respect to the proximal control device and the one or more structures to at least partially deploy the implant from the inner tubular member; and (c) releasing the implant from the delivery device, wherein the outer tubular member is deflected by winding the pull wire around the rotatable wheel during the step of releasing the implant in step (c), and wherein the outer tubular member is locked in a deflected position by frictionally engaging the latch with the ledge after the outer tubular member is deflected. Winding of the pull wire around the rotatable wheel results in deflection of the outer tubular member and unwinding of the pull wire from the rotatable wheel results in straightening of the outer tubular member. The extension is movable from a first position to a second position by rotating at least a portion of the housing. When the extension is in the first position, the rotatable wheel is capable of winding or unwinding the pull wire. When the extension is in the second position, the rotatable wheel is not capable of winding or unwinding the pull wire. In the first position, the extension is angled away from a distal end of the outer tubular member. In the second position, the extension is angled towards a distal end of the outer tubular member and the latch is frictionally engaged by the ledge when the extension is in the second position. The method may further include the step of unlocking the outer tubular member from the deflected position by disengaging the latch from the ledge, wherein the extension returns to the first position.

In some embodiments, the system further includes an elongate member coupled with the retainer and having a proximal end that is manipulatable by a user to permit release of the distal portion of the implant from the retainer. In some embodiments, the retainer is tubular and adapted to slide along the distal control member. In some embodiments, the distal control member includes a recess adapted to receive the distal portion of the implant. In some embodiments, the retainer is movable to uncover the recess while the distal portion of the implant is received within the recess. In some embodiments, the retainer includes a slot.

In some embodiments, the system further includes an elongate anchor member. In some embodiments, the elongate anchor member includes an anchor configured to contact a bladder wall. In some embodiments, the anchor is an inflatable balloon. In some embodiments, the elongate anchor member includes multiple balloons. In some embodiments, the elongate anchor member includes a wire-form member having a portion configured to automatically deflect when deployed. The inflated diameter of the anchor balloon can be between about 1 cm and 7 cm, alternatively between about 2 cm and 6 cm, alternatively between about 1 cm and 6 cm.

In some embodiments, the elongate grasper member includes a recess configured to releasably couple with the proximal portion of an implant. In some embodiments, the system is configured such that the proximal portion of the implant is free to release from the recess of the elongate grasper member when the recess is unconstrained by the first inner lumen.

In some embodiments, the distal end region of the outer tubular member further includes an illumination device.

In some embodiments, the second portion includes: a first flexible bus having a first end electrically connected to a printed circuit board within the second portion and a second end electrically connected to the imaging device; and a second flexible bus having a first end electrically connected to the printed circuit board within the second portion and a second end electrically connected to the illumination device.

In some embodiments, the imaging module is mounted to at least one elongate member that extends through a lumen of the outer tubular member. The imaging module is configured to be positioned distal of the distal end of the outer tubular member upon distal advancement of the at least one elongate member. The imaging module may include a camera and a light source. The imaging module may be mounted to at least one, two, three, or more elongate members. The imaging module may be configured to be positioned between about 0 cm to about 5 cm distal of the distal end of the outer tubular member.

In some embodiments, the proximal control device includes a rotary adapter, which is coupled to an imaging device. The proximal control device is coupled with the inner tubular member and the one or more structures, and releasably coupled with the outer tubular member with a coupling mechanism. The rotary adapter can include a distal component, a sliding component, a spring and a proximal component. The imaging device can be coupled to the sliding component of the rotary adapter. The spring may be located between the distal component and the sliding component, enabling the imaging device to be advanced in a distal direction when the spring is compressed. Alternatively, the spring may be located between the sliding component and the proximal component, enabling the imaging device to be advanced in a proximal direction when the spring is compressed.

In some embodiments, the rotary adapter may also conduct electricity. The rotary adapter may comprise an electrical plate or ring that conducts electricity. In some embodiments, the sliding component may include the electrical plate or ring. The rotary adapter may also be connected to a light source or an imaging device.

In some embodiments, a distal end region of the inner tubular member is distal to the distal end region of the outer tubular member by a separation distance, and where the proximal control device is configured to longitudinally move the outer tubular member and inner tubular member concurrently without changing the separation distance.

In some embodiments, the implant is sized to fit entirely within a prostatic urethra. In some embodiments, the delivery system is usable to deliver the implant to an anterior position within the prostatic urethra. In some embodiments, the delivery system is usable to deliver the implant to a posterior position within the prostatic urethra.

In many embodiments, a method of imaging delivery of an implant is provided, the method including: advancing a delivery device within a urethra of a patient, where the delivery device includes an outer tubular member including an imaging device located in a distal end region of the outer tubular member, an inner tubular member within the outer tubular member and housing at least a portion of an implant, and one or more structures slidably advanceable within the inner tubular member to cause deployment of the implant from within the inner tubular member, where the outer tubular member, inner tubular member, and one or more structures are each coupled with a proximal control device outside of the patient; longitudinally retracting the inner tubular member with respect to the proximal control device and the one or more structures to at least partially deploy the implant from the inner tubular member; and while the inner tubular member is being longitudinally retracted, concurrently (a) longitudinally retracting the outer tubular member with respect to the proximal control device and (b) imaging the at least partially deployed implant with an imaging device located at a distal end region of the outer tubular member. In some embodiments, the urethra is the prostatic urethra.

In some embodiments, a method of imaging delivery of an implant is provide, the method including: advancing a delivery device within a urethra of a patient, wherein the delivery device comprises an outer tubular member comprising an imaging device associated with a distal end region of the outer tubular member, an inner tubular member within the outer tubular member, the inner tubular member including a first elongate tubular member having a lumen that is adapted to house at least a portion of an implant, a second elongate tubular member having a lumen, and at least one support defining a plane that is generally perpendicular to a longitudinal axis of the inner tubular member, and one or more structures slidably advanceable within the lumen of the second elongate tubular member to cause deployment of the implant from within the inner tubular member, wherein the outer tubular member, inner tubular member, and one or more structures are each coupled with a proximal control device outside of the patient; and longitudinally retracting the inner tubular member with respect to the proximal control device and the one or more structures to at least partially deploy the implant from the inner tubular member. The method may further include the steps of concurrently (a) longitudinally retracting the outer tubular member with respect to the proximal control device and (b) imaging the at least partially deployed implant with an imaging device, while the inner tubular member is being longitudinally retracted.

In some embodiments, a method of imaging delivery of an implant is provide, the method including: advancing a delivery device within a urethra of a patient, wherein the delivery device comprises an outer tubular member comprising first and second lumens and a distal end, an imaging module mounted to at least one elongate member that extends through the second lumen, an inner tubular member within the first lumen and housing at least a portion of an implant, and one or more structures slidably advanceable within the inner tubular member to cause deployment of the implant from within the inner tubular member, wherein the outer tubular member, inner tubular member, and one or more structures are each coupled with a proximal control device outside of the patient; longitudinally retracting the inner tubular member with respect to the proximal control device and the one or more structures to at least partially deploy the implant from the inner tubular member; extending the imaging module distally beyond the distal end of the outer tubular member; and imaging the at least partially deployed implant.

In some embodiments, a method of imaging delivery of an implant is provide, the method including: advancing a delivery device within a urethra of a patient, wherein the delivery device comprises an outer tubular member comprising an imaging device associated with a distal end region of the outer tubular member, an inner tubular member within the outer tubular member, wherein the inner tubular member comprises a first elongate tubular member having a lumen that is adapted to house at least a portion of an implant and a second elongate tubular member comprising an opening in a distal end region communicating with a lumen, and one or more structures slidably advanceable within the lumen of the second elongate tubular member to cause deployment of the implant, the one or more structures comprising a retainer configured to releasably couple with a distal portion of an implant, wherein the retainer is coupled to an elongate member that extends proximally within the lumen of the second elongate tubular member, wherein the elongate member passes out of and back into the opening forming a loop that prevents the retainer from moving in a proximal direction, wherein the outer tubular member, inner tubular member, and one or more structures are each coupled with a proximal control device outside of the patient; longitudinally retracting the inner tubular member with respect to the proximal control device and the one or more structures to at least partially deploy the implant from the inner tubular member; and releasing the implant from the delivery device by pulling the elongate member in a proximal direction, wherein the loop is withdrawn into the lumen of the second elongate tubular member and the retainer is moved in a proximal direction. The method may further include the steps of concurrently (a) longitudinally retracting the outer tubular member with respect to the proximal control device and (b) imaging the at least partially deployed implant with an imaging device associated with a distal end region of the outer tubular member, while the inner tubular member is being longitudinally retracted.

In some embodiments, a method of imaging delivery of an implant is provide, the method including: advancing a delivery device within a urethra of a patient, wherein the delivery device comprises an outer tubular member, an inner tubular member within the outer tubular member and housing at least a portion of an implant, one or more structures slidably advanceable within the inner tubular member to cause deployment of the implant from within the inner tubular member, and an imaging device, wherein the outer tubular member, inner tubular member, one or more structures, and imaging device are each coupled with a proximal control device outside of the patient, and wherein the proximal control device comprises a rotary adapter that is coupled to the imaging device; longitudinally retracting the inner tubular member with respect to the proximal control device and the one or more structures to at least partially deploy the implant from the inner tubular member; longitudinally moving (e.g., retracting or advancing) the imaging device with respect to a distal end of the inner tubular member; and imaging the at least partially deployed implant with the imaging device.

In some embodiments, the method further includes releasing the implant from the delivery device. In some embodiments, the method further includes releasing the implant from the delivery device such that the implant is entirely within the prostatic urethra.

In some embodiments, the implant is released while in an expanded state, the diameter of the implant in the expanded state being less than the smallest width of the prostatic urethra where the implant is released.

In some embodiments, the implant is released such that the implant contacts the posterior most tissue surface of the prostatic urethra. In some embodiments, the implant is released such that the implant does not contact the anterior most tissue surface of the prostatic urethra.

In some embodiments, the implant is released such that the implant contacts the anterior most tissue surface of the prostatic urethra. In some embodiments, the implant is released such that the implant does not contact the posterior most tissue surface of the prostatic urethra.

In some embodiments, a method of imaging delivery of an implant is provide, the method including: advancing a delivery device within a urethra of a patient, wherein the delivery device comprises an outer tubular member comprising an imaging device located in a distal end region of the outer tubular member, an inner tubular member within the outer tubular member, wherein the inner tubular member comprises a first elongate tubular member having a lumen that is adapted to house at least a portion of an implant and a second elongate tubular member an opening in a distal end region communicating with a lumen, and one or more structures slidably advanceable within the lumen of the second elongate tubular member to cause deployment of the implant, the one or more structures comprising a retainer configured to releasably couple with a distal portion of an implant, wherein the retainer is coupled to an elongate member extending within the lumen of the second elongate tubular member, wherein the elongate member passes out of and back into the opening forming a loop that prevents the retainer from moving in a proximal direction, wherein the outer tubular member, inner tubular member, and one or more structures are each coupled with a proximal control device outside of the patient; longitudinally retracting the inner tubular member with respect to the proximal control device and the one or more structures to at least partially deploy the implant from the inner tubular member; while the inner tubular member is being longitudinally retracted, concurrently (a) longitudinally retracting the outer tubular member with respect to the proximal control device and (b) imaging the at least partially deployed implant with an imaging device located at a distal end region of the outer tubular member; and releasing the implant from the delivery device by pulling the elongate member in a proximal direction, wherein the loop is withdrawn into the lumen of the second elongate tubular member and the retainer is moved in a proximal direction.

In some embodiments, the outer tubular member is longitudinally retracted at the same rate as the inner tubular member.

In some embodiments, the method further includes: rotating the inner tubular member with respect to the proximal control device to at least partially deploy the implant from the inner tubular member; and while the inner tubular member is being rotated, concurrently (a) maintaining the outer tubular member in a rotationally fixed position with respect to the proximal control device and (b) imaging the at least partially deployed implant with the imaging device.

In some embodiments, the method further includes the following steps performed prior to advancing the delivery device within the urethra of the patient: inserting the inner tubular member into the outer tubular member, where the inner tubular member is coupled with a first portion of the proximal control device and the outer tubular member is coupled with a second portion of the proximal control device; and coupling the first portion of the proximal control device to the second portion of the proximal control device. In some embodiments, coupling the first portion of the proximal control device to the second portion of the proximal control device includes coupling a deflectable member of the second portion to a groove of the first portion.

In some embodiments, the method further includes illuminating the implant with an illumination device at the distal end region of the outer tubular member.

In many embodiments, a method of user assembly of a proximal control device is provided, the method including: inserting an inner tubular member into an outer tubular member, where the inner tubular member is coupled with a first portion of a proximal control device and the outer tubular member is coupled with a second portion of the proximal control device; and coupling the first portion of the proximal control device to the second portion of the proximal control device with a coupling mechanism, where the inner tubular member is longitudinally and rotationally movable with respect to the first portion of the proximal control device, where the first portion is coupled to the second portion such that longitudinal movement of the inner tubular member causes longitudinal movement of the second portion and outer tubular member, and where the first portion is coupled to the second portion such that rotational movement of the inner tubular member does not cause rotational movement of the second portion and outer tubular member.

In some embodiments, the first portion can couple to the second portion in more than one position, and the method includes: coupling the first portion of the proximal control device to the second portion of the proximal control device with the coupling mechanism in a first position; uncoupling the first portion of the proximal control device from the second portion of the proximal control device; and coupling the first portion of the proximal control device to the second portion of the proximal control device with the coupling mechanism in a second position.

In some embodiments, the first position corresponds to a first distance between a distal terminus of the inner tubular member and a distal terminus of the outer tubular member, and the second position corresponds to a second distance between the distal terminus of the inner tubular member and the distal terminus of the outer tubular member, where the first and second distances are different. In some embodiments, the second distance is greater than the first distance and corresponds to a relatively wider field of imaging for the second position as compared to the first position.

In many embodiments, a method of delivering an implant is provided, the method including: advancing a delivery device within a urethra of a patient; deploying an implant from the delivery device to a position entirely within a prostatic urethra of the patient, where the implant transitions from a unexpanded state to an expanded state upon deployment; and removing the delivery device from the patient while the implant remains in the prostatic urethra in the expanded state that maintains a pathway through the prostatic urethra, the diameter of the implant in the expanded state being less than the smallest width of the prostatic urethra adjacent the implant, where, after removal of the delivery device, the implant contacts the posterior most tissue surface of the prostatic urethra.

In some embodiments, after removal of the delivery device, the implant contacts the posterior most tissue surface of the prostatic urethra and does not contact the anterior most tissue surface of the prostatic urethra.

In many embodiments, a method of delivering an implant is provided, the method including: advancing a delivery device within a urethra of a patient; deploying an implant from the delivery device to a position entirely within a prostatic urethra of the patient, where the implant transitions from a unexpanded state to an expanded state upon deployment; and removing the delivery device from the patient while the implant remains in the prostatic urethra in the expanded state that maintains a pathway through the prostatic urethra, the diameter of the implant in the expanded state being less than the smallest width of the prostatic urethra adjacent the implant, where, after removal of the delivery device, the implant contacts the anterior most tissue surface of the prostatic urethra.

In some embodiments, after removal of the delivery device, the implant contacts the anterior most tissue surface of the prostatic urethra and does not contact the posterior most tissue surface of the prostatic urethra.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

As used herein and in the appended claims, the singular forms “a,” “an,” and “the” include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A method of imaging delivery of an implant, the method comprising:

advancing a delivery device within a urethra of a patient, wherein the delivery device comprises an outer tubular member comprising first and second lumens and a distal end, an imaging module mounted to at least one elongate member extending through the second lumen, an inner tubular member extending through the first lumen and housing at least a portion of the implant, and one or more structures slidably advanceable within the inner tubular member to cause deployment of the implant from within the inner tubular member, wherein the outer tubular member, inner tubular member, and one or more structures are each coupled with a proximal control device outside of the patient;

longitudinally retracting the inner tubular member with respect to the proximal control device and the one or more structures to at least partially deploy the implant from the inner tubular member;

extending the imaging module distally beyond the distal end of the outer tubular member; and imaging the at least partially deployed implant.

2. The method of claim 1, wherein the urethra is a prostatic urethra.

3. The method of claim 1, further comprising releasing the implant from the delivery device.

4. The method of claim 1, wherein the outer tubular member is longitudinally retracted at the same rate as the inner tubular member.

5. The method of claim 1, further comprising:

rotating the inner tubular member with respect to the proximal control device to at least partially deploy the implant from the inner tubular member; and while the inner tubular member is being rotated, concurrently (a) maintaining the outer tubular member in a rotationally fixed position with respect to the proximal control device and (b) imaging the at least partially deployed implant with the imaging device.

6. The method of claim 1, wherein the implant has a body comprising first and second ring-shaped structures and an interconnect that extends between the first and second ring-shaped structures, wherein the second ring-shaped structure is proximal the first ring-shaped structure.

7. The method of claim 1, wherein the imaging module can visualize placement of the second ring-shaped structure after being extended distal of the distal end of the outer tubular member.

8. The method of claim 7, further comprising the step of releasing the implant from the delivery device after imaging.

9. The method of claim 1, wherein the extending the imaging module includes extending the imaging module to or beyond a distal end of the at least partially deployed implant.

* * * * *